United States Patent
Abiad et al.

(10) Patent No.: US 12,144,847 B2
(45) Date of Patent: *Nov. 19, 2024

(54) NON-PROTEIN CLOSTRIDIAL TOXIN COMPOSITIONS

(71) Applicant: Allergan, Inc., Irvine, CA (US)

(72) Inventors: Maurice Abiad, Anaheim, CA (US); Bhas Dani, San Diego, CA (US); Evgenyi Shalaev, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/136,048

(22) Filed: Apr. 18, 2023

(65) Prior Publication Data

US 2023/0355723 A1 Nov. 9, 2023

Related U.S. Application Data

(60) Division of application No. 17/185,312, filed on Feb. 25, 2021, now abandoned, which is a continuation of application No. 16/531,800, filed on Aug. 5, 2019, now Pat. No. 10,973,890, which is a division of application No. 15/703,527, filed on Sep. 13, 2017, now Pat. No. 10,369,190.

(60) Provisional application No. 62/394,009, filed on Sep. 13, 2016.

(51) Int. Cl.
| | |
|---|---|
| *A61K 39/02* | (2006.01) |
| *A61K 9/00* | (2006.01) |
| *A61K 9/19* | (2006.01) |
| *A61K 38/16* | (2006.01) |
| *A61K 38/48* | (2006.01) |
| *A61K 47/10* | (2017.01) |
| *A61K 47/18* | (2017.01) |
| *A61K 47/26* | (2006.01) |
| *A61P 9/06* | (2006.01) |
| *A61P 13/00* | (2006.01) |
| *A61P 21/00* | (2006.01) |
| *A61P 25/24* | (2006.01) |
| *A61P 29/00* | (2006.01) |

(52) U.S. Cl.
CPC ........ *A61K 38/4893* (2013.01); *A61K 9/0019* (2013.01); *A61K 9/19* (2013.01); *A61K 38/164* (2013.01); *A61K 38/48* (2013.01); *A61K 47/10* (2013.01); *A61K 47/183* (2013.01); *A61K 47/26* (2013.01); *A61P 9/06* (2018.01); *A61P 13/00* (2018.01); *A61P 21/00* (2018.01); *A61P 25/24* (2018.01); *A61P 29/00* (2018.01)

(58) Field of Classification Search
CPC .............................................. A61K 38/4893
See application file for complete search history.

(56) References Cited

U.S. PATENT DOCUMENTS

| | | |
|---|---|---|
| 4,891,319 A | 1/1990 | Roser |
| 5,472,706 A | 12/1995 | Friedman et al. |
| 5,512,547 A | 4/1996 | Johnson et al. |
| 5,556,771 A | 9/1996 | Shen et al. |
| 5,616,554 A | 4/1997 | Beardsley |
| 5,696,077 A | 12/1997 | Johnson et al. |
| 5,714,468 A | 2/1998 | Binder |
| 5,756,468 A | 5/1998 | Johnson et al. |
| 5,945,098 A | 8/1999 | Sarno et al. |
| 5,962,637 A | 10/1999 | Shone et al. |
| 5,989,545 A | 11/1999 | Foster et al. |
| 6,043,042 A | 3/2000 | Shone et al. |
| 6,087,327 A | 7/2000 | Pearce et al. |
| 6,203,794 B1 | 3/2001 | Dolly et al. |
| 6,306,423 B1 | 10/2001 | Donovan et al. |
| 6,337,386 B1 | 1/2002 | Shone et al. |
| 6,461,617 B1 | 10/2002 | Shone et al. |
| 6,506,399 B2 | 1/2003 | Donovan |
| 6,555,558 B2 | 4/2003 | Chen et al. |
| 6,599,504 B1 | 7/2003 | Wadstrom et al. |
| 6,632,440 B1 | 10/2003 | Quinn et al. |
| 6,653,062 B1 | 11/2003 | Depablo et al. |
| 6,777,196 B2 | 8/2004 | Klein et al. |
| 6,843,998 B1 | 1/2005 | Steward et al. |
| 6,977,080 B1 | 12/2005 | Donovan |
| 7,001,602 B2 | 2/2006 | Schmidt |
| 7,132,259 B1 | 11/2006 | Dolly et al. |
| 7,160,699 B2 | 1/2007 | Wang et al. |
| 7,183,066 B2 | 2/2007 | Fernandez-Salas et al. |

(Continued)

FOREIGN PATENT DOCUMENTS

| | | |
|---|---|---|
| AU | 2009339292 B2 | 1/2016 |
| CN | 1215084 A | 4/1999 |

(Continued)

OTHER PUBLICATIONS

European Patent Office, Interlocutory decision dated Mar. 12, 2019, in opposition proceedings of EP 2679217, 29 pages.

(Continued)

*Primary Examiner* — Albert M Navarro

(74) *Attorney, Agent, or Firm* — Foley Hoag LLP; Hathaway P. Russell; Benjamin A. Vaughan

(57) ABSTRACT

Pharmaceutical compositions that stabilize a Clostridial toxin active ingredient are described. The compositions can be liquid or solid compositions, and comprise a surfactant and an antioxidant. In some embodiments, the compositions comprise a surfactant selected from a poloxamer and a polysorbate; an antioxidant selected from methionine, N-acetyl cysteine, ethylenediaminetetraacetic acid and combinations thereof, and, optionally, a tonicity agent and/or a lyoprotector selected from, for example, trehalose, sucrose.

24 Claims, No Drawings

(56) References Cited

U.S. PATENT DOCUMENTS

| | | |
|---|---|---|
| 7,205,018 B2 | 4/2007 | Sherwood et al. |
| 7,208,166 B2 | 4/2007 | Marchini et al. |
| 7,208,285 B2 | 4/2007 | Steward et al. |
| 7,211,261 B1 | 5/2007 | Moyer et al. |
| 7,223,577 B2 | 5/2007 | Steward et al. |
| 7,255,865 B2 | 8/2007 | Walker |
| 7,273,722 B2 | 9/2007 | Lin et al. |
| 7,309,602 B2 | 12/2007 | David |
| 7,332,567 B2 | 2/2008 | Steward et al. |
| 7,341,843 B2 | 3/2008 | Atassi |
| 7,354,740 B2 | 4/2008 | Xiang et al. |
| 7,375,079 B2 | 5/2008 | Gordon et al. |
| 7,399,607 B2 | 7/2008 | Williams et al. |
| 7,419,676 B2 | 9/2008 | Dolly et al. |
| 7,442,686 B2 | 10/2008 | Mckerracher et al. |
| 7,473,559 B2 | 1/2009 | Lee |
| 7,491,403 B2 | 2/2009 | Borodic |
| 7,531,193 B2 | 5/2009 | Demarne et al. |
| 7,560,100 B2 | 7/2009 | Pinchasi et al. |
| 7,579,010 B2 | 8/2009 | Hunt |
| 7,579,171 B2 | 8/2009 | Porro et al. |
| 7,591,806 B2 | 9/2009 | Xu |
| 7,598,027 B2 | 10/2009 | Fernandez-Salas et al. |
| 7,601,740 B2 | 10/2009 | Weiner et al. |
| 7,604,802 B2 | 10/2009 | Ohagan et al. |
| 7,642,079 B2 | 1/2010 | Cayouette et al. |
| 7,645,570 B2 | 1/2010 | Fernandez-Salas et al. |
| 7,674,454 B2 | 3/2010 | Huizinga et al. |
| 7,727,537 B2 | 6/2010 | Modi |
| 7,758,872 B1 | 7/2010 | Finzi |
| 7,776,844 B2 | 8/2010 | Yu et al. |
| 7,780,967 B2 | 8/2010 | Hunt |
| 7,829,525 B2 | 11/2010 | Frevert |
| 7,838,011 B2 | 11/2010 | Modi |
| 7,846,722 B2 | 12/2010 | Williams et al. |
| 7,867,480 B1 | 1/2011 | Cevc et al. |
| 7,875,436 B2 | 1/2011 | Fournie-Zaluski et al. |
| 7,879,341 B2 | 2/2011 | Taylor |
| 7,906,136 B2 | 3/2011 | Wong et al. |
| 7,910,554 B2 | 3/2011 | Mckerracher et al. |
| 7,927,622 B1 | 4/2011 | Cevc et al. |
| 7,998,489 B2 | 8/2011 | Steward et al. |
| 8,057,807 B2 | 11/2011 | Schmidt |
| 8,057,808 B2 | 11/2011 | Ackerman |
| 8,067,200 B2 | 11/2011 | Foster et al. |
| 8,124,357 B2 | 2/2012 | Fernandez-Salas et al. |
| 8,137,677 B2 | 3/2012 | Hunt |
| 8,143,212 B2 | 3/2012 | Stogniew et al. |
| 8,158,360 B2 | 4/2012 | Heise et al. |
| 8,168,206 B1 | 5/2012 | Hunt |
| 8,173,138 B2 | 5/2012 | Moyer et al. |
| 8,192,979 B2 | 6/2012 | Borodic et al. |
| 8,241,640 B2 | 8/2012 | Borodic |
| 8,257,699 B2 | 9/2012 | Bookbinder et al. |
| 8,277,822 B2 | 10/2012 | Dott et al. |
| 8,283,133 B2 | 10/2012 | Franciskovich et al. |
| 8,309,077 B2 | 11/2012 | Murthy et al. |
| 8,323,666 B2 | 12/2012 | Hunt |
| 8,343,508 B2 | 1/2013 | Pomato et al. |
| 8,357,541 B2 | 1/2013 | Ton et al. |
| 8,372,645 B2 | 2/2013 | Taylor |
| 8,398,997 B2 | 3/2013 | Dake et al. |
| 8,398,998 B2 | 3/2013 | Bigalke et al. |
| 8,399,006 B2 | 3/2013 | De, Jr. et al. |
| 8,404,249 B2 | 3/2013 | Dake |
| 8,420,081 B2 | 4/2013 | Fraunhofer et al. |
| 8,444,991 B2 | 5/2013 | Randolph et al. |
| 8,470,330 B2 | 6/2013 | Maddon et al. |
| 8,476,024 B2 | 7/2013 | Mahrhold et al. |
| 8,486,467 B1 | 7/2013 | Prescott |
| 8,501,195 B2 | 8/2013 | Turkel et al. |
| 8,512,679 B2 | 8/2013 | Hyde et al. |
| 8,512,979 B2 | 8/2013 | Dunson, Jr. et al. |
| 8,529,939 B2 | 9/2013 | Masters et al. |
| 8,580,250 B2 | 11/2013 | Hunt |
| 8,580,252 B2 | 11/2013 | Bookbinder et al. |
| 8,586,020 B2 | 11/2013 | Song et al. |
| 8,591,884 B2 | 11/2013 | Soparkar et al. |
| 8,609,112 B2 | 12/2013 | Blumenfeld et al. |
| 8,617,568 B2 | 12/2013 | Jung et al. |
| 8,618,261 B2 | 12/2013 | Fernandez-Salas et al. |
| 8,623,419 B2 | 1/2014 | Malakhov et al. |
| 8,632,785 B2 | 1/2014 | Hunt |
| 8,642,047 B2 | 2/2014 | Hunt |
| 8,647,638 B2 | 2/2014 | Clarke et al. |
| 8,669,091 B2 | 3/2014 | Gentschev et al. |
| 8,685,381 B2 | 4/2014 | Schlessinger et al. |
| 8,685,684 B2 | 4/2014 | Lee et al. |
| 8,697,155 B2 | 4/2014 | Levy et al. |
| 8,697,644 B2 | 4/2014 | Prestrelski et al. |
| 8,703,755 B2 | 4/2014 | Adams et al. |
| 8,715,706 B2 | 5/2014 | Barak |
| 8,716,240 B2 | 5/2014 | Defrees et al. |
| 8,729,241 B2 | 5/2014 | Liu et al. |
| 8,734,826 B2 | 5/2014 | Barak |
| 8,796,217 B2 | 8/2014 | Amari et al. |
| 8,808,710 B2 | 8/2014 | Randolph et al. |
| 8,821,879 B2 | 9/2014 | Babuka et al. |
| 8,828,432 B2 | 9/2014 | Van Lengerich |
| 8,840,905 B2 | 9/2014 | Schmidt |
| 8,841,110 B2 | 9/2014 | Xiang et al. |
| 8,883,146 B2 | 11/2014 | Fraunhofer et al. |
| 8,889,151 B2 | 11/2014 | Turkel et al. |
| 8,889,826 B2 | 11/2014 | Leese et al. |
| 8,920,795 B2 | 12/2014 | Jung et al. |
| 8,936,790 B2 | 1/2015 | Turkel et al. |
| 8,940,308 B2 | 1/2015 | Turkel et al. |
| 8,968,747 B2 | 3/2015 | Turkel et al. |
| 8,993,268 B2 | 3/2015 | Jung et al. |
| 9,006,388 B2 | 4/2015 | Paul et al. |
| 9,012,177 B2 | 4/2015 | Glass et al. |
| 9,017,726 B2 | 4/2015 | Song et al. |
| 9,040,074 B2 | 5/2015 | Holzer et al. |
| 9,044,477 B2 | 6/2015 | Blanda et al. |
| 9,050,336 B2 | 6/2015 | Blanda et al. |
| 9,050,367 B2 | 6/2015 | Taylor |
| 9,061,025 B2 | 6/2015 | Burstein |
| 9,066,943 B2 | 6/2015 | Schmidt |
| 9,072,688 B2 | 7/2015 | Boyden et al. |
| 9,078,892 B2 | 7/2015 | Turkel et al. |
| 9,078,893 B2 | 7/2015 | Turkel et al. |
| 9,085,619 B2 | 7/2015 | Fraunhofer et al. |
| 9,107,815 B2 | 8/2015 | Hunt |
| 9,109,244 B2 | 8/2015 | Pompejus et al. |
| 9,125,804 B2 | 9/2015 | Webb et al. |
| 9,157,875 B2 | 10/2015 | Warner et al. |
| 9,161,970 B2 | 10/2015 | Tezel et al. |
| 9,173,944 B2 | 11/2015 | Taylor et al. |
| 9,180,081 B2 | 11/2015 | Dake et al. |
| 9,198,856 B2 | 12/2015 | Burger et al. |
| 9,198,945 B2 | 12/2015 | Kim et al. |
| 9,198,958 B2 | 12/2015 | Jung et al. |
| 9,211,248 B2 | 12/2015 | Dake et al. |
| 9,211,315 B2 | 12/2015 | Bookbinder et al. |
| 9,220,780 B2 | 12/2015 | Jung et al. |
| 9,220,783 B2 | 12/2015 | Taylor |
| 9,226,959 B2 | 1/2016 | Kramps et al. |
| 9,233,080 B2 | 1/2016 | Golubovic-Lakopoulos et al. |
| 9,233,238 B2 | 1/2016 | Buysman et al. |
| 9,248,168 B2 | 2/2016 | Blumenfeld |
| 9,265,722 B2 | 2/2016 | Donovan |
| 9,278,140 B2 | 3/2016 | Hunt |
| 9,283,217 B2 | 3/2016 | Dibas et al. |
| 9,284,566 B2 | 3/2016 | Liao et al. |
| 9,284,579 B2 | 3/2016 | Green et al. |
| 9,302,008 B2 | 4/2016 | Hunt |
| 9,327,105 B2 | 5/2016 | Ramdas et al. |
| 9,340,587 B2 | 5/2016 | Thompson et al. |
| 9,389,162 B2 | 7/2016 | Chen et al. |
| 9,394,234 B2 | 7/2016 | Chen et al. |
| 9,415,006 B2 | 8/2016 | Baker, Jr. et al. |
| 9,447,401 B2 | 9/2016 | Wei et al. |
| 9,452,157 B2 | 9/2016 | Viscomi et al. |
| 9,458,536 B2 | 10/2016 | Felts et al. |

(56) References Cited

U.S. PATENT DOCUMENTS

| | | |
|---|---|---|
| 9,474,688 B2 | 10/2016 | Weeks et al. |
| 9,480,731 B2 | 11/2016 | Jung et al. |
| 9,486,408 B2 | 11/2016 | Edelson et al. |
| 9,512,495 B2 | 12/2016 | Eyal et al. |
| 9,517,202 B2 | 12/2016 | Chen et al. |
| 9,517,255 B2 | 12/2016 | Turzi |
| 9,539,233 B2 | 1/2017 | Ohtake et al. |
| 9,554,968 B2 | 1/2017 | Weikart et al. |
| 9,567,345 B2 | 2/2017 | Eickhoff et al. |
| 9,603,799 B2 | 3/2017 | Sorayya et al. |
| 9,629,904 B2 | 4/2017 | Hunt |
| 9,650,608 B2 | 5/2017 | Khan et al. |
| 9,657,279 B2 | 5/2017 | Voigt et al. |
| 9,662,450 B2 | 5/2017 | Jones et al. |
| 9,669,107 B2 | 6/2017 | Kim et al. |
| 9,687,541 B2 | 6/2017 | Middaugh et al. |
| 9,695,248 B2 | 7/2017 | Maddon et al. |
| 9,713,643 B2 | 7/2017 | Friedman et al. |
| 9,724,397 B2 | 8/2017 | Cherif-Cheikh et al. |
| 9,725,705 B2 | 8/2017 | Xiang |
| 9,744,237 B2 | 8/2017 | Moazed |
| 9,750,797 B2 | 9/2017 | Brandon et al. |
| 9,757,329 B2 | 9/2017 | Webb et al. |
| 9,763,898 B2 | 9/2017 | Schiffrin et al. |
| 9,764,031 B2 | 9/2017 | Ilyinskii et al. |
| 9,790,511 B2 | 10/2017 | Desfougeres et al. |
| 9,795,614 B2 | 10/2017 | Grosskreutz et al. |
| 9,815,886 B2 | 11/2017 | Grossman et al. |
| 9,878,036 B2 | 1/2018 | Coulter et al. |
| 9,890,400 B2 | 2/2018 | Walther et al. |
| 9,901,627 B2 | 2/2018 | Borodic |
| 9,937,099 B2 | 4/2018 | Weikart et al. |
| 9,950,042 B2 | 4/2018 | Borodic |
| 9,956,194 B2 | 5/2018 | Ohlstein et al. |
| 9,956,435 B2 | 5/2018 | Ruegg et al. |
| 9,981,022 B2 | 5/2018 | Hunt |
| 10,016,338 B2 | 7/2018 | Weikart et al. |
| 10,022,384 B2 | 7/2018 | Giliyar et al. |
| 10,030,238 B2 | 7/2018 | Cossins et al. |
| 10,047,384 B2 | 8/2018 | Medoff et al. |
| 10,071,103 B2 | 9/2018 | Sengupta |
| 10,080,786 B2 | 9/2018 | Dake et al. |
| 10,081,654 B2 | 9/2018 | Verdine et al. |
| 10,086,013 B2 | 10/2018 | Dong et al. |
| 10,087,432 B2 | 10/2018 | Rummel et al. |
| 10,098,840 B2 | 10/2018 | Mosqueira et al. |
| 10,105,421 B2 | 10/2018 | Taylor |
| 10,111,939 B2 | 10/2018 | Thompson et al. |
| 10,117,941 B2 | 11/2018 | Manoharan et al. |
| 10,118,965 B2 | 11/2018 | Kim et al. |
| 10,143,728 B2 | 12/2018 | Jung et al. |
| 10,201,594 B2 | 2/2019 | Ruegg et al. |
| 10,245,317 B2 | 4/2019 | Biemans et al. |
| 10,258,673 B2 | 4/2019 | Pokushalov et al. |
| 10,260,111 B1 | 4/2019 | Etchebarne |
| 10,286,044 B2 | 5/2019 | Bookbinder et al. |
| 10,293,034 B2 | 5/2019 | Jung et al. |
| 10,307,468 B2 | 6/2019 | Palan et al. |
| 10,325,685 B2 | 6/2019 | Apte et al. |
| 10,327,423 B2 | 6/2019 | Ala'aldeen et al. |
| 10,329,526 B2 | 6/2019 | Salmons et al. |
| 10,335,370 B2 | 7/2019 | Xu et al. |
| 10,342,812 B2 | 7/2019 | Wang |
| 10,366,789 B2 | 7/2019 | Apte et al. |
| 10,366,793 B2 | 7/2019 | Apte et al. |
| 10,369,190 B2 | 8/2019 | Abiad et al. |
| 10,377,785 B2 | 8/2019 | Ala'aldeen et al. |
| 10,381,112 B2 | 8/2019 | Apte et al. |
| 10,383,519 B2 | 8/2019 | Apte et al. |
| 10,406,139 B2 | 9/2019 | Austad et al. |
| 10,410,749 B2 | 9/2019 | Apte et al. |
| 10,456,473 B2 | 10/2019 | Manoharan et al. |
| 10,465,197 B2 | 11/2019 | Mcclain et al. |
| 10,471,150 B2 | 11/2019 | Konorty et al. |
| 10,532,019 B2 | 1/2020 | Edelson et al. |
| 10,973,890 B2 | 4/2021 | Abiad et al. |
| 2001/0038858 A1 | 11/2001 | Roser et al. |
| 2002/0037833 A1 | 3/2002 | Donovan |
| 2002/0044968 A1 | 4/2002 | van Lengerich |
| 2002/0064536 A1 | 5/2002 | Hunt |
| 2002/0107199 A1 | 8/2002 | Walker |
| 2003/0118598 A1 | 6/2003 | Hunt |
| 2003/0138437 A1 | 7/2003 | Hunt |
| 2003/0138460 A1 | 7/2003 | Hunt |
| 2003/0180289 A1 | 9/2003 | Foster et al. |
| 2004/0009180 A1 | 1/2004 | Donovan |
| 2004/0043374 A1 | 3/2004 | Depablo et al. |
| 2004/0086532 A1 | 5/2004 | Donovan |
| 2004/0143213 A1 | 7/2004 | Hunter et al. |
| 2004/0161776 A1 | 8/2004 | Maddon et al. |
| 2004/0204471 A1 | 10/2004 | Seibert |
| 2004/0213813 A1 | 10/2004 | Ackerman |
| 2004/0214753 A1 | 10/2004 | Britten et al. |
| 2004/0220386 A1 | 11/2004 | Steward et al. |
| 2005/0025778 A1 | 2/2005 | Cormier et al. |
| 2005/0069562 A1 | 3/2005 | Donovan |
| 2005/0112135 A1 | 5/2005 | Cormier et al. |
| 2005/0123565 A1 | 6/2005 | Subramony et al. |
| 2005/0147690 A1 | 7/2005 | Masters et al. |
| 2005/0153873 A1 | 7/2005 | Chan et al. |
| 2005/0214325 A1 | 9/2005 | David |
| 2005/0220854 A1 | 10/2005 | Maa et al. |
| 2005/0238663 A1 | 10/2005 | Hunt |
| 2005/0238668 A1 | 10/2005 | Wang et al. |
| 2005/0244358 A1 | 11/2005 | Ocha |
| 2005/0260186 A1 | 11/2005 | Bookbinder et al. |
| 2005/0266011 A1 | 12/2005 | Maa et al. |
| 2005/0271684 A1 | 12/2005 | Trautman et al. |
| 2006/0002862 A1 | 1/2006 | Truong-Le et al. |
| 2006/0018931 A1 | 1/2006 | Taylor |
| 2006/0057165 A1 | 3/2006 | Dimitrakoudis et al. |
| 2006/0073207 A1 | 4/2006 | Masters et al. |
| 2006/0073333 A1 | 4/2006 | Anderson |
| 2006/0182767 A1 | 8/2006 | Borodic |
| 2006/0211619 A1 | 9/2006 | Steward et al. |
| 2006/0269575 A1 | 11/2006 | Hunt |
| 2006/0292224 A1 | 12/2006 | Ross et al. |
| 2007/0020295 A1 | 1/2007 | Donovan |
| 2007/0026019 A1 | 2/2007 | Hunt |
| 2007/0134199 A1 | 6/2007 | Frevert |
| 2007/0166332 A1 | 7/2007 | Steward et al. |
| 2008/0020000 A1 | 1/2008 | Mckerracher |
| 2008/0044390 A1 | 2/2008 | Jin et al. |
| 2008/0057575 A1 | 3/2008 | Fernandez-Salas et al. |
| 2008/0069841 A1 | 3/2008 | Panjwani et al. |
| 2008/0096248 A1 | 4/2008 | Steward et al. |
| 2008/0138893 A1 | 6/2008 | Steward et al. |
| 2008/0187960 A1 | 8/2008 | Foster et al. |
| 2008/0220021 A1 | 9/2008 | Modi et al. |
| 2008/0241881 A1 | 10/2008 | Steward et al. |
| 2008/0274194 A1 | 11/2008 | Miller et al. |
| 2008/0279896 A1 | 11/2008 | Heinen et al. |
| 2009/0155314 A1 | 6/2009 | Tezel et al. |
| 2009/0181007 A1 | 7/2009 | Gennero et al. |
| 2009/0181083 A1 | 7/2009 | Holm et al. |
| 2009/0324584 A1 | 12/2009 | Hoerr |
| 2009/0324647 A1 | 12/2009 | Borodic |
| 2010/0150994 A1 | 6/2010 | Kotyla |
| 2010/0158951 A1 | 6/2010 | Randolph et al. |
| 2010/0184689 A1 | 7/2010 | Panjwani et al. |
| 2010/0203559 A1 | 8/2010 | Ester et al. |
| 2010/0233741 A1 | 9/2010 | Wang et al. |
| 2010/0233802 A1 | 9/2010 | Zhu et al. |
| 2010/0260796 A1 | 10/2010 | Belin-Poput et al. |
| 2010/0266638 A1 | 10/2010 | Turkel et al. |
| 2010/0279953 A1 | 11/2010 | Hun |
| 2010/0291136 A1 | 11/2010 | Jung et al. |
| 2010/0330123 A1 | 12/2010 | Thompson et al. |
| 2011/0091503 A1 | 4/2011 | Taylor |
| 2011/0091921 A1 | 4/2011 | Aigner et al. |
| 2011/0200657 A1 | 8/2011 | Baker |
| 2012/0039862 A1 | 2/2012 | Borodic |
| 2012/0093866 A1 | 4/2012 | Burger et al. |
| 2012/0107361 A1 | 5/2012 | Thompson et al. |

(56) References Cited

U.S. PATENT DOCUMENTS

| | | |
|---|---|---|
| 2012/0114625 A1 | 5/2012 | Wiessel et al. |
| 2012/0122128 A1 | 5/2012 | Fernandez-Salas et al. |
| 2012/0122802 A1 | 5/2012 | Hunt |
| 2012/0148562 A1 | 6/2012 | Ho et al. |
| 2012/0258126 A1 | 10/2012 | Schoeller et al. |
| 2013/0017587 A1 | 1/2013 | Nierlich et al. |
| 2013/0046275 A1 | 2/2013 | Holzer et al. |
| 2013/0121987 A1 | 5/2013 | Taylor |
| 2013/0171282 A1 | 7/2013 | Kim et al. |
| 2013/0203148 A1 | 8/2013 | Steward et al. |
| 2013/0224248 A1 | 8/2013 | Taylor |
| 2013/0230856 A1 | 9/2013 | Schneider et al. |
| 2013/0330321 A1 | 12/2013 | Turkel et al. |
| 2013/0344167 A1 | 12/2013 | Chery et al. |
| 2014/0030241 A1 | 1/2014 | Greenberg |
| 2014/0030248 A1 | 1/2014 | Turkel et al. |
| 2014/0037603 A1 | 2/2014 | Bolster et al. |
| 2014/0044695 A1 | 2/2014 | Hunt |
| 2014/0056863 A1 | 2/2014 | Greenberg et al. |
| 2014/0086900 A1 | 3/2014 | Jung et al. |
| 2014/0112908 A1 | 4/2014 | Hunt |
| 2014/0120077 A1 | 5/2014 | Ruegg et al. |
| 2014/0154237 A1 | 6/2014 | Waugh et al. |
| 2014/0161783 A1 | 6/2014 | Jung et al. |
| 2014/0199288 A1 | 7/2014 | Hunt |
| 2014/0228782 A1 | 8/2014 | Barak |
| 2014/0294788 A1 | 10/2014 | Bailey et al. |
| 2014/0294803 A1 | 10/2014 | Turkel et al. |
| 2014/0301455 A1 | 10/2014 | Lee et al. |
| 2014/0356340 A1 | 12/2014 | Burbidge et al. |
| 2015/0004149 A1 | 1/2015 | Burbidge et al. |
| 2015/0064166 A1 | 3/2015 | Jung et al. |
| 2015/0086532 A1 | 3/2015 | Borodic |
| 2015/0165003 A1 | 6/2015 | Jung et al. |
| 2015/0175707 A1 | 6/2015 | De Jong et al. |
| 2015/0238527 A1 | 8/2015 | Chang et al. |
| 2015/0297684 A1 | 10/2015 | Borodic |
| 2015/0297800 A1 | 10/2015 | Weikart et al. |
| 2015/0308988 A1 | 10/2015 | Babuka et al. |
| 2015/0313973 A1 | 11/2015 | Forssen et al. |
| 2015/0330972 A1 | 11/2015 | Boyle et al. |
| 2015/0335576 A1 | 11/2015 | Chan et al. |
| 2015/0352226 A1 | 12/2015 | Hunt |
| 2016/0000737 A1 | 1/2016 | Zemel et al. |
| 2016/0022764 A1 | 1/2016 | Sharma et al. |
| 2016/0073650 A1 | 3/2016 | Wiessel et al. |
| 2016/0073659 A1 | 3/2016 | Zemel et al. |
| 2016/0089442 A1 | 3/2016 | Jung et al. |
| 2016/0131669 A1 | 5/2016 | Li et al. |
| 2016/0151482 A1 | 6/2016 | Carnes et al. |
| 2016/0175408 A1 | 6/2016 | Chang et al. |
| 2016/0184413 A1 | 6/2016 | Taylor |
| 2016/0194669 A1 | 7/2016 | Argyros et al. |
| 2016/0206710 A1 | 7/2016 | Jung et al. |
| 2016/0213757 A1 | 7/2016 | Edelson et al. |
| 2016/0228409 A1 | 8/2016 | Cross, III |
| 2016/0250302 A1 | 9/2016 | Zhu et al. |
| 2016/0354418 A1 | 12/2016 | Quintens et al. |
| 2017/0007675 A1 | 1/2017 | Prestrelski et al. |
| 2017/0037438 A1 | 2/2017 | Helman et al. |
| 2017/0042983 A1 | 2/2017 | Jung et al. |
| 2017/0136105 A1 | 5/2017 | Ho et al. |
| 2017/0181952 A1 | 6/2017 | Edelson et al. |
| 2017/0202954 A1 | 7/2017 | Jezek |
| 2017/0204394 A1 | 7/2017 | Slovic et al. |
| 2017/0209389 A1 | 7/2017 | Toth et al. |
| 2017/0209553 A1 | 7/2017 | Kaspar et al. |
| 2017/0216414 A1 | 8/2017 | Tezel et al. |
| 2017/0224786 A1 | 8/2017 | Hunt |
| 2017/0275279 A1 | 9/2017 | Buckner et al. |
| 2017/0290778 A1 | 10/2017 | Waugh |
| 2017/0304601 A1 | 10/2017 | Gardner et al. |
| 2017/0326242 A1 | 11/2017 | Da Silveira Moreira et al. |
| 2017/0342395 A1 | 11/2017 | Xiang |
| 2017/0347664 A1 | 12/2017 | Thompson et al. |
| 2017/0348226 A1 | 12/2017 | Webb et al. |
| 2017/0348263 A1 | 12/2017 | Ohlstein et al. |
| 2017/0356002 A1 | 12/2017 | Thompson et al. |
| 2018/0027833 A1 | 2/2018 | Wiessel et al. |
| 2018/0055779 A1 | 3/2018 | Park et al. |
| 2018/0065966 A1 | 3/2018 | Bhattacharjee et al. |
| 2018/0071361 A1 | 3/2018 | Abiad et al. |
| 2018/0078589 A1 | 3/2018 | Kyle et al. |
| 2018/0092851 A1 | 4/2018 | Hassett et al. |
| 2018/0147357 A1 | 5/2018 | Marashi et al. |
| 2018/0161406 A1 | 6/2018 | Singh |
| 2018/0164298 A1 | 6/2018 | Ali et al. |
| 2018/0177831 A9 | 6/2018 | Borody et al. |
| 2018/0214557 A1 | 8/2018 | Tan et al. |
| 2018/0214717 A1 | 8/2018 | Ruegg et al. |
| 2018/0237847 A1 | 8/2018 | Culler |
| 2018/0243543 A1 | 8/2018 | Baek et al. |
| 2018/0258159 A1 | 9/2018 | Grossman et al. |
| 2018/0271959 A1 | 9/2018 | Hunt |
| 2018/0282309 A1 | 10/2018 | Fieldhouse et al. |
| 2018/0296582 A1 | 10/2018 | Von Maltzahn et al. |
| 2018/0303945 A1 | 10/2018 | Adams et al. |
| 2018/0333475 A1 | 11/2018 | Dorsey et al. |
| 2018/0344820 A1 | 12/2018 | Jacky et al. |
| 2019/0002507 A1 | 1/2019 | Giacalone et al. |
| 2019/0008795 A1 | 1/2019 | Waugh et al. |
| 2019/0008845 A1 | 1/2019 | Canedo |
| 2019/0032105 A1 | 1/2019 | Quiring et al. |
| 2019/0038726 A1 | 2/2019 | Turkel et al. |
| 2019/0050534 A1 | 2/2019 | Apte et al. |
| 2019/0076518 A1 | 3/2019 | Singh |
| 2019/0083434 A1 | 3/2019 | Ohlstein et al. |
| 2019/0099474 A1 | 4/2019 | Jung et al. |
| 2019/0111119 A1 | 4/2019 | Moon et al. |
| 2019/0142936 A1 | 5/2019 | Cui et al. |
| 2019/0142940 A1 | 5/2019 | Moazed |
| 2019/0151465 A1 | 5/2019 | Kim et al. |
| 2019/0183785 A1 | 6/2019 | Edelson et al. |
| 2019/0183986 A1 | 6/2019 | Sanders |
| 2019/0183988 A1 | 6/2019 | Jarstad et al. |
| 2019/0194630 A1 | 6/2019 | Bradshaw et al. |
| 2019/0201505 A1 | 7/2019 | Palan et al. |
| 2019/0201506 A1 | 7/2019 | Lee et al. |
| 2019/0201630 A1 | 7/2019 | Vogt |
| 2019/0216862 A1 | 7/2019 | Goodman et al. |
| 2019/0224253 A1 | 7/2019 | Sandy et al. |
| 2019/0231750 A1 | 8/2019 | Schanbacher et al. |
| 2019/0231844 A1 | 8/2019 | Chen et al. |
| 2019/0233167 A1 | 8/2019 | Felts et al. |
| 2019/0240263 A1 | 8/2019 | Goodman et al. |
| 2019/0247293 A1 | 8/2019 | Dake et al. |
| 2019/0247476 A1 | 8/2019 | Abiad et al. |
| 2019/0262266 A1 | 8/2019 | Moen et al. |
| 2019/0262438 A1 | 8/2019 | Borodic |
| 2019/0274746 A1 | 9/2019 | Toth et al. |
| 2019/0276859 A1 | 9/2019 | Bestel-Corre et al. |
| 2019/0290740 A1 | 9/2019 | Thompson et al. |
| 2019/0298813 A1 | 10/2019 | Jung et al. |
| 2019/0321355 A1 | 10/2019 | Anavi-Goffer et al. |
| 2019/0321427 A1 | 10/2019 | Ganz et al. |
| 2019/0343139 A1 | 11/2019 | Snow et al. |
| 2019/0345436 A1 | 11/2019 | Tracy et al. |
| 2019/0350987 A1 | 11/2019 | Goodman et al. |
| 2019/0351034 A1 | 11/2019 | Abiad et al. |
| 2019/0381160 A1 | 12/2019 | Petit et al. |
| 2019/0381185 A1 | 12/2019 | Kim et al. |
| 2019/0388541 A1 | 12/2019 | Thyagarajan et al. |
| 2020/0009473 A1 | 1/2020 | Jung et al. |
| 2020/0108129 A1 | 4/2020 | Wu et al. |
| 2021/0290739 A1 | 9/2021 | Abiad et al. |
| 2021/0369821 A1 | 12/2021 | Abiad et al. |
| 2023/0173041 A1 | 6/2023 | Abiad et al. |

FOREIGN PATENT DOCUMENTS

| | | |
|---|---|---|
| CN | 103705913 | 4/2014 |
| CN | 105833254 A | 8/2016 |
| EP | 1390053 A2 | 2/2004 |
| EP | 1253932 B1 | 4/2005 |

(56) References Cited

FOREIGN PATENT DOCUMENTS

| | | |
|---|---|---|
| EP | 1747672 | 2/2010 |
| EP | 1112082 B2 | 3/2010 |
| EP | 2248518 B1 | 1/2013 |
| EP | 2511844 B1 | 3/2013 |
| EP | 2720712 B1 | 3/2016 |
| EP | 2373294 B1 | 4/2016 |
| EP | 2679217 B1 | 4/2016 |
| EP | 2692350 B1 | 5/2017 |
| EP | 2709657 B1 | 10/2018 |
| EP | 2943077 B1 | 10/2018 |
| EP | 3405585 A1 | 11/2018 |
| EP | 3436054 A2 | 2/2019 |
| EP | 3380124 A1 | 6/2019 |
| EP | 3380125 A1 | 8/2019 |
| EP | 3538080 A1 | 9/2019 |
| EP | 3448399 A4 | 5/2020 |
| GB | 2419527 A | 5/2006 |
| JP | H10203997 A | 8/1998 |
| JP | H11507072 A | 6/1999 |
| JP | 2005527470 A | 9/2005 |
| JP | 2012512162 A | 5/2012 |
| JP | 2019526609 A | 9/2019 |
| KR | 20110106346 A | 9/2011 |
| KR | 20120112248 A | 10/2012 |
| KR | 20140041460 A | 4/2014 |
| NO | 2018102343 A1 | 6/2018 |
| NO | 2018112138 A1 | 6/2018 |
| RU | 2535115 C1 | 12/2014 |
| WO | WO-1995017904 A2 | 7/1995 |
| WO | 9533850 A1 | 12/1995 |
| WO | 9611699 A1 | 4/1996 |
| WO | 9639166 A1 | 12/1996 |
| WO | 9735604 A1 | 10/1997 |
| WO | 0137656 A1 | 5/2001 |
| WO | 0158472 A1 | 8/2001 |
| WO | 0193827 A1 | 12/2001 |
| WO | 2004060384 A1 | 10/2004 |
| WO | 2005007185 A1 | 5/2005 |
| WO | WO-2005084705 A1 | 9/2005 |
| WO | 2006013357 A1 | 2/2006 |
| WO | 2005084410 A1 | 3/2006 |
| WO | 2005121354 A2 | 3/2006 |
| WO | 2006020208 A2 | 6/2006 |
| WO | 2006042149 A1 | 7/2006 |
| WO | 2006059093 A2 | 8/2006 |
| WO | 2006005910 A2 | 9/2006 |
| WO | 2006106823 A1 | 10/2006 |
| WO | 2007041664 | 4/2007 |
| WO | 2006122123 A2 | 6/2007 |
| WO | 2007048638 A2 | 7/2007 |
| WO | 2007044809 A2 | 8/2007 |
| WO | 2006059105 A2 | 11/2007 |
| WO | 2008049631 A1 | 5/2008 |
| WO | 2008133884 A2 | 11/2008 |
| WO | 2008118691 A2 | 12/2008 |
| WO | 2009008595 A1 | 1/2009 |
| WO | 2009051837 A2 | 7/2009 |
| WO | 2009128644 A2 | 4/2010 |
| WO | 2010011597 A2 | 4/2010 |
| WO | 2010078242 A1 | 7/2010 |
| WO | 2010090677 | 8/2010 |
| WO | 2010094463 A1 | 8/2010 |
| WO | 2010096134 A1 | 8/2010 |
| WO | 2010118888 A1 | 10/2010 |
| WO | 2011103465 A2 | 2/2012 |
| WO | 2012015912 A1 | 2/2012 |
| WO | 2010146591 A2 | 3/2012 |
| WO | 2011110948 A2 | 3/2012 |
| WO | 2012048854 A2 | 6/2012 |
| WO | 2012094163 A1 | 7/2012 |
| WO | 2012116209 A1 | 8/2012 |
| WO | 2012134240 A2 | 1/2013 |
| WO | 2013028781 A1 | 2/2013 |
| WO | 2013071138 A1 | 5/2013 |
| WO | 2013170052 A1 | 11/2013 |
| WO | 2014008138 A2 | 1/2014 |
| WO | 2014026161 | 2/2014 |
| WO | 2010151840 A2 | 3/2014 |
| WO | 2014005039 A2 | 3/2014 |
| WO | 2014068317 A1 | 5/2014 |
| WO | 2014124096 A1 | 8/2014 |
| WO | 2014165617 A1 | 10/2014 |
| WO | 2014184746 A1 | 11/2014 |
| WO | 2014190944 A1 | 12/2014 |
| WO | 2014006217 A1 | 2/2015 |
| WO | 2015020982 A2 | 2/2015 |
| WO | 2014144842 A2 | 4/2015 |
| WO | 2015089452 A1 | 6/2015 |
| WO | 2015157595 A1 | 10/2015 |
| WO | 2015166242 A1 | 11/2015 |
| WO | 2015120231 A2 | 12/2015 |
| WO | 2016014750 A1 | 1/2016 |
| WO | 2016048689 A1 | 3/2016 |
| WO | 2016083549 A2 | 7/2016 |
| WO | 2016154112 A1 | 9/2016 |
| WO | 2016191545 A1 | 2/2017 |
| WO | 2017066121 A1 | 6/2017 |
| WO | 2017089894 A1 | 6/2017 |
| WO | 2017179775 A1 | 10/2017 |
| WO | 2017203038 A1 | 11/2017 |
| WO | 2017220553 A1 | 12/2017 |
| WO | 2018038301 A1 | 3/2018 |
| WO | 2018038585 A1 | 3/2018 |
| WO | 2018039318 A1 | 3/2018 |
| WO | 2018053021 A1 | 3/2018 |
| WO | 2018053004 A2 | 4/2018 |
| WO | 2018065972 A1 | 4/2018 |
| WO | 2018083692 A1 | 5/2018 |
| WO | 2018112419 A1 | 6/2018 |
| WO | 2018130099 A1 | 7/2018 |
| WO | 2018135722 A1 | 7/2018 |
| WO | 2018136617 A2 | 8/2018 |
| WO | 2018175899 A1 | 9/2018 |
| WO | 2018195097 A1 | 10/2018 |
| WO | 2018206772 A1 | 11/2018 |
| WO | 2018222652 A1 | 12/2018 |
| WO | 2018234645 A1 | 12/2018 |
| WO | 2018216974 A2 | 1/2019 |
| WO | 2019005773 A1 | 1/2019 |
| WO | 2019046311 A1 | 3/2019 |
| WO | 2019046529 A1 | 3/2019 |
| WO | 2019051204 A1 | 3/2019 |
| WO | 2019051380 A1 | 3/2019 |
| WO | 2019070850 A1 | 4/2019 |
| WO | 2019075452 A1 | 4/2019 |
| WO | 2019092504 A1 | 5/2019 |
| WO | 2019104135 A1 | 5/2019 |
| WO | 2019104136 A1 | 5/2019 |
| WO | 2019118393 A1 | 6/2019 |
| WO | 2019127719 A1 | 7/2019 |
| WO | 2019135244 A2 | 8/2019 |
| WO | 2019147799 A1 | 8/2019 |
| WO | 2019152667 A1 | 8/2019 |
| WO | 2019155391 A1 | 8/2019 |
| WO | 2019164134 A1 | 8/2019 |
| WO | 2019166514 A1 | 9/2019 |
| WO | 2019174560 A1 | 9/2019 |
| WO | 2019178055 A1 | 9/2019 |
| WO | 2019178359 A1 | 9/2019 |
| WO | 2019178490 A1 | 9/2019 |
| WO | 2019178494 A1 | 9/2019 |
| WO | 2019178487 A2 | 11/2019 |
| WO | 2019211382 A1 | 11/2019 |
| WO | 2019226599 A1 | 11/2019 |

OTHER PUBLICATIONS

Innotox, Botulinum toxin products, retrieved from https://www.asushit.com/index.php?route=product/product&product_id=26092, on Jan. 10, 2021, 6 pages.

Medytox, History of Medytox, retrieved from www.medytox.com/page/history_en?site_id=en, on Jan. 10, 2021, 4 pages.

(56) References Cited

OTHER PUBLICATIONS

Saito, Y., Pluronic Surfactants, J. Japanese Oil Chemists' Soc., 2000, 53-62.
Rowe, R., et al., Aliphatic Polyesters, Handbook of Pharmaceutical Excipients 2003, 4th ed., 19-21.
Finzi, E., et al. Treatment of Depression with Botulinum Toxin A: A Case Series, Derma. Surg. 2006, 32: 645-650.
Extended European Search Report for EP Application No. EP 19190978.7 dated Nov. 13, 2020.
Chen, C., Applications of emulsifiers in pharmaceutical formulations, China Sufactant Detergent & Comestics 2014, 44 (10): 590-593.
Akers "Excipient-drug interactions in parental formulations" Journal of Pharmaceutical Sciences, vol. 91, No. 11 ,pp. 2283-2300 (2002).
Alam et al., "Pain Associated With Injection of Botulinum A Exotoxin Reconstituted Using Isotonic Sodium Chloride With and Without Preservative: A Double-Blind, Randomized Controlled Trial", Arch. Dermatol., vol. 138, No. 4, pp. 510-514 (2002).
Allergan Inc. "Stability of lypholized botulinum toxin compositions: Compositions comprising Sucrose", European Patent No. 13178507.3, Doc# HE 166929 o11/u7, Jun. 2015.
Allergan Inc. "Stability of lypholized botulinum toxin compositions: Compositions of Sucrose", European Patent No. 13178507.3, Doc# HE 120308 o11/u7, Nov. 2019.
Amersdorfer et al., "Molecular Characterization of Murine Humoral Immune Response to Botulinum Neurotoxin Type A Binding Domain as Assessed by Using Phage Antibody Libraries", Infect. Immun. Vol. 65, No. 9, pp. 3743-3752 (1997).
Atmaca, "Antioxidant Effects of Sulfur-Containing Amino Acids", Yonsei Medical Journal, vol. 45, No. 5, pp. 776-788 (2004).
Borodic et al., "Effects of Repeated Botulinum Toxin Injections on Orbicularis Oculi Muscle", J. Clin. Neuro-opthalmology, vol. 12, No. 2, pp. 121-127 (1992).
Borodic et al., "Therapy with Botulinum Toxin", Neurological Disease and Therapy, Ed., Jankovic, pp. 119-157 (1994).
Boyd et al., "The Effect of Botulinum Neurotoxins on the Release of Insulin from the Insulinoma Cell Lines HIT-15 and RINm5F", J. Biol. Chem., vol. 270, No. 31, pp. 18216-18218 (1995).
Bradshaw et al., "Regulation of Neurotoxin Complex Expression in Clostridium Botulinum Strains 62A, Hall A-hyper, and NCTC 2916", Anaerobe, vol. 10, No. 6, pp. 321-333 (2004).
Brandt et al., "Efficacy and Safety Evaluation of a Novel Botulinum Toxin Topical Gel for the Treatment of Moderate to Severe Lateral Canthal Lines", Dermatol. Surg., vol. 36, Suppl. 4, pp. 2111-2118 (2010).
Brashear et al., " A multicenter, double-blind, randomized, placebo-controlled, parallel study of the safety and efficacy of BOTOX (botulinum toxin type A) purified neurotoxin in the treatment of focal upper limb spasticity poststroke", Neurology, vol. 56, Suppl. 3, pp. A78 (2001) Abstract only.
Carpenter et al., "Interactions of stabilizers with proteins during freezing and drying", Formulation and Delivery of Protein and Peptides, ACS Symposiums Series, vol. 567, Eds. Cleland, J.L. and Langer, R., Washington D.C., American Chemical Society, pp. 134-147 (1994).
Carpenter et al., "Interactions of Stabilizing Additives with Proteins During Freeze-Thawing and Freeze-Drying", International Symposium on Biological Product Freeze-Drying and Formulation, Oct. 24-26, 1990; Karger (1992), 225-239.
Carpenter et al., "Rational Design of Stable Lyophilized Protein Formulations: Theory and Practice", Pharm. Biotechnol., vol. 13, pp. 109-133 (2002).
Carruthers et al., "Improvement of Tension-Type Headache When Treating Wrinkles With Botulinum Toxin A Injections", Headache, vol. 39, No. 9, pp. 662-665 (1999).
Carruthers et al., "Botox: Beyond Wrinkles", Clinics in Dermatology, vol. 22, No. 1, pp. 89-93 (2004).
Cheng et al., "Unlabeled Uses of Botulinum Toxins: A Review, Part 1", Am. J. Health Syst. Pharm., vol. 63, No. 2, pp. 145-152 (2006).
Choi et al., "Effective Botulinum Toxin Injection Guide for Treatment of Temporal Headache", Toxins (Basel), vol. 8, No. 9, Art. 265, 10 pages (2016).
Decision of the Opposition Division regarding the validity of EP patent No. 2679217, Dated Mar. 12, 2019.
Definition of "Saline" by Oxford Dictionaryy on Lexico.com, Also meaning of Saline, Online article obtained from http:www.lexico.com/saline (2020).
Depiereux et al., "Match-Box: A Fundamentally New Algorithm for the Simultaneous Alignment of Several Protein Sequences", Comput. Appl. Biosci., vol. 8, No. 5, pp. 501-509 (1992).
Doft et al., "Treatment of Axillary Hyperhidrosis With Botulinum Toxin: A Single Surgeon's Experience With 53 Consecutive Patients", Aesthetic Plast. Surg., vol. 35, No. 6, pp. 1079-1086 (2011).
Dressler "Five-year Experience With incobotulinumtoxinA (Xeomin®)): The First Botulinum Toxin Drug Free of Complexing Proteins", European Journal of Neurology, vol. 19, No. 3, pp. 385-389 (2012).
Pickar et al., Excerpt, "Example 3", Dosage Calculation, 7th Edition, Thomson, Delmar Learning, 5 Maxwell Drive, Clifton Park, NY, 3 pages (2004).
Edgar, "Muscle: Multiple Sequence Alignment with High Accuracy and High Throughput", Nucleic Acids Research, vol. 32, No. 5, pp. 1792-1797, (2004).
European Commision Guidelines: Medicinal products for human use safety, environment and information; Excipients In the label and package leaflet of medicinal products for human use, vol. 3B; Jul. 2003.
Experimental Report Filed by the Patentee Allergan During Opposition Proceedings Corresponding to EP application No. 09768315. 5, Allergan ref. No. 149691 011/u7, 2 pages, Document filed May 2018.
Experimental Report D10, Filed by the Patentee Allergan During Opposition Proceedings Corresponding to EP application No. 13178507. 3, Allergan ref. No. 166929 u7/011, 1 page, Document filed Nov. 2018.
Foran et al., "Botulinum Neurotoxin C1 Cleaves Both Syntaxin and SNAP-25 In Intact and Permeabilized Chromaffin Cells: Correlation With Its Blockade Of Catecholamine Release", Biochemistry, vol. 35, No. 8, pp. 2630-2636 (1996).
Foster et al., Ophthalmology Times, pp. 13-15 (1997).
Garcia-Rodriguez., "Molecular Evolution of Antibody Cross-Reactivity for Two Subtypes of Type A Botulinum Neurotoxin", Nature Biotechnol., vol. 25, No. 1, pp. 107-116 (2007).
Glogau et al., "Results of a Randomized, Double-Blind, Placebo-Controlled Study to Evaluate the Efficacy and Safety of a Botulinum Toxin Type A Topical Gel for the Treatment of Moderate-To-Severe Lateral Canthal Lines", J. Drugs Dermatol., vol. 11, No. 1, pp. 38-45 (2012).
Goodnough et al., "Recovery of type-A botulinal toxin following lyophilization", Acs Symposium Series, 567 (-):193-203 (1994).
Gotoh, "Significant Improvement in Accuracy of Multiple Protein Sequence Alignments by Iterative Refinement as Assessed by Reference to Structural Alignments", J. Mol. Biol., vol. 264, No. 4, pp. 823-838 (1996).
Grosse et al., "Success of Repeat Detrusor Injections of Botulinum a Toxin in Patients With Severe Neurogenic Detrusor Overactivity and Incontinence", European Urology, vol. 47, No. 5, pp. 653-659 (2005).
Hallis et al., "Development of Novel Assays for Botulinum Type A and B Neurotoxins Based on Their Endopeptidase Activities", J. Clin. Microbiol., vol. 34, No. 8, pp. 1934-1938 (1996).
Humeau et al., "How Botulinum and Tetanus Neurotoxins Block Neurotransmitter Release", Biochimie, vol. 82, No. 5, pp. 427-446, (2000).
Jabbari et al., "Treatment of Refractory Pain With Botulinum Toxins-An Evidence-Based Review", Pain Med., vol. 12, No. 11, pp. 1594-1606 (2011).
Johnson, "Preparation of Peptide and Protein Powders for Inhalation", Adv. Drug Del. Rev., vol. 26, No. 1, pp. 3-15 (1997).
Johnson and Bradshaw, "Clostridial botulinum and its Neurotoxins: A Metabolic and Cellular Perspective", Toxicon, vol. 39, No. 11, pp. 1703-1722 (2001).

(56) References Cited

OTHER PUBLICATIONS

Jones et al., "Development of Improved SNAP-25 Endopeptidase Immunoassays for Botulinum Type A and E Toxins", J. Immunol. Methods, vol. 329, No. 1-2, pp. 92-101 (2008).
Kim et al., "The Efficacy and Safety of Liquid-Type Botulinum Toxin Type A for the Management of Moderate to Severe Glabellar Frown Lines", Plast. Reconstr. Surg., vol. 135, No. 3, pp. 732-741 (2015).
Kohl et al., "Comparison of the effect of botulinum toxin A (Botox ®) with the highly-purified neurotoxin (NT 201) in the extensor digitorum brevis muscle test", Mov. Discord vol. 15, Suppl 3, Abst. 165 (2000).
Lalli et al., "The Journey of Tetanus and Bolulinum Neurotoxins in Neurons", Trends in Microbiol., vol. 11, No. 9, pp. 431-437 (2003).
Lang, "History and Uses of BOTOX (Botulinum Toxin Type A)", Lippincotts Case Management, vol. 9, No. 2, pp. 109-112 (2004).
Lawrence et al., "Detecting Subtle Sequence Signals: A Gibbs Sampling Strategy for Multiple Alignment", Science, vol. 262, No. 5131, pp. 208-214 (1993).
Lipham, "Cosmetic and Clinical Applications of Botulinum Toxin", Slack Incorporated, 1st Ed., 2 pages, (2004).
Malhotra et al., "Botulinum Toxin and Human Serum Albumin", Arch. Ophthalmol., vol. 121, No. 11, pp. 1661-1662 (2003).
Marconi et al., "A protein-chip Membrane-Capture Assay for Botulinum Neurotoxin Activity", Toxicol. App. Pharmacol., vol. 233, No. 3, pp. 439-446 (2008).
Marini et al., "SiMa, a New Neuroblastoma Cell Line Combining Poor Prognostic Cytogenetic Markers with High Adrenergic Differentiation", Cancer Genet. Cytogenet., vol. 112, No. 2, pp. 161-164 (1999).
Masumoto et al., "Involvement of SNAP-25 in TRH-induced Exocytosis in Pituitary GH4C1 Cells", Journal of Endocrinology, vol. 153, No. 1, pp. R5-R10 (1997).
McLeod et al., "Loss of factor VIII activity during storage in PVC containers due to adsorption", Hemophilia, vol. 6, No. 2, pp. 89-92 (2000).
Mocellin et al., "DNA Array-Based Gene Profiling: From Surgical Specimen to the Molecular Portrait of Cancer", Ann. Surg., vol. 241, No. 1, pp. 16-26 (2005).
Morgenstern et al., "Multiple DNA and Protein Sequence Alignment Based on Segment-to-Segment Comparison", Proc. Natl. Acad. Sci., vol. 93, No. 22, pp. 12098-12103 (1996).
Nabokina et al., "Intracellular Location of SNAP-25 in Human Neutrophils", Biochem. Biophys.239, No. 2, pp. 592-597 (1997).
Naumann et al., "Botulinum toxin type A in the treatment of focal, axillary and palmar hyperhidrosis and other hyperhidrotic conditions", European J. Neurology, vol. 6, Supp 4, pp. s111-s115 (1999).
Nizai, "Handbook of Pharmaceutical Manufacturing Formulations: Liquid Products", Informa Healthcare, USA, Inc., 52 Vanderbilt Avenue, New York, NY, 10017, vol. 3, p. 58, (2004).
Notredame et al., "T-Coffee: A Novel Method for Fast and Accurate Multiple Sequence Alignment", J Mol. Biol., vol. 302, No. 1, pp. 205-217 (2000).
Ortisi et al., "Blepharospasm and Hemifacial Spasm: A Protocol for Titration of Botulinum Toxin Dose to the Individual Patient and for the Management of Refractory Cases", Eye (Lond), vol. 20, No. 8, pp. 916-922 (2006).
Osterberg et al., "Development of Freeze-Dried Albumin-Free Formulation of Recombinant Factor VIII SQ", Pharm. Res., vol. 14, No. 7, pp. 892-898 (1997).
Panicker and Muthane, "Botulinum Toxins: Pharmacology and Its Current Therapeutic Evidence for Use", Neurol. India, vol. 51, No. 4, pp. 455-460 (2003).
Parish, "Commercial Preparations and Handling of Botulinum Toxin Type A and Type B", Clin. Dermat., vol. 21, No. 6, pp. 481-484 (2003).
Parkins and Lashmar, "The Formulation of Biopharmaceutical Products", Pharm. Sci. Technolo. Today, vol. 3, No. 4, pp. 129-137 (2000).

Pellett et al., "A Neuronal Cell-Based Botulinum Neurotoxin Assay For Highly Sensitive and Specific Detection of Neutralizing Serum Antibodies", FEBS Lett., vol. 581, No. 25, pp. 4803-4808 (2007).
Zhou et al., "Biotherapeutic formulation factors affecting metal leachables from stainless steel studied by design experiments" AAPS PharmSciTech, Vo. 13, No. 1, pp. 284-294 (2012).
Poliziani et al., "Striving for More Good Days: Patient Perspectives on Botulinum Toxin for the Treatment of Cervical Dystonia", Patient Prefer. Adherence, vol. 10, No. 10, pp. 1601-1608 (2016).
Raffestin et al., "Organization and Regulation of the Neurotoxin Genes in Clostridium Botulinum and Clostridium Tetani", Anaerobe, vol. 10, No. 2, pp. 93-100 (2004).
Ragona et al., "Management of Parotid Sialocele with Botulinum Toxin", Laryngoscope, vol. 109, No. 8, pp. 1344-1346 (1999).
Ramirez-Castaneda and Jankovic, "Long-term Efficacy and Safety of Botulinum Toxin Injections in Dystonia", Toxins (Basel), vol. 5, No. 2, pp. 249-266 (2013).
Rasooly and Do, "Development of an In Vitro Assay as an Alternative to the Mouse Bioassay for *Clostridium botulinum* Neurotoxin Type A", App. Environ. Microbiol., vol. 74, No. 14, pp. 4309-4313 (2008).
Schantz and Johnson "Properties and Use of Botulinum Toxin and Other Microbial Neurotoxins in Medicine", Microbiol. Rev., vol. 56, No. 1, pp. 80-99 (1992).
Schulte-Baukloh et al., "Persistence of the Synaptosomal-Associated protein-25 Cleavage Product After Intradetrusor Botulinum Toxin A Injections in Patients With Myelomeningocele Showing an Inadequate Response to Treatment", BJU Int., vol. 100, No. 5, pp. 1075-1080 (2007).
Sellers and Maa, "Principles of Biopharmaceutical Protein Formulation: An Overview", Meth. Mol. Biol., vol. 308, pp. 243-263 (2005).
Sesardic et al., "Role for Standards in Assays of Botulinum Toxins: International Collaborative Study of Three Preparations of Botulinum Type A Toxin", Biologicals, vol. 31, No. 4, pp. 256-276 (2003).
Shih et al., "Expression Profiling by Microarrays in Colorectal Cancer (Review)", Oncol. Rep., vol. 13, No. 3, pp. 517-524 (2005).
Shimazaki et al., "Phosphorylation of 25-kDa Synaptosome-Associated Protein. Possible Involvement in Protein Kinase C-mediated Regulation of Neurotransmitter Release", J. Biol. Chem., vol. 271, No. 24, pp. 14548-14533 (1996).
Silberstein et al., "Botulinum Toxin Type A in the Prophylactic Treatment of Chronic Tension-Type Headache: A Multicentre, Double-Blind, Randomized, Placebo-Controlled, Parallel-Group Study", Cephalgia, vol. 26, No. 7, pp. 790-800 (2006).
Singh, "Critical Aspects of Bacterial Protein Toxins", Adv, Exp. Med. Biol., vol. 391, pp. 63-84 (1996).
Subramanian et al., "DIALIGN-T: An Improved Algorithm for Segment-Based Multiple Sequence Alignment", BMC Bioinformatics, 2005, vol. 6, Art. 66, 13 Pages (2005).
Thompson et al., "Clustal W: Improving the Sensitivity of Progressive Multiple Sequence Alignment Through Sequence Weighting, Position-Specific Gap Penalties and Weight Matrix Choice", Nucleic Acids Res., vol. 22, No. 22, pp. 4673-4680 (1994).
Troost, "Botulinum Toxin Type A (BOTOX) in the Treatment of Migraine and Other Headaches", Expert. Rev. Neurother., vol. 4, No. 1, pp. 27-31 (2004).
Trompetto et al., "Do Flexible Inter-Injection Intervals Improve the Effects of Botulinum Toxin A Treatment in Reducing Impairment and Disability in Patients With Spasticity?", Medical Hypotheses, vol. 102, pp. 28-32 (2017).
Tumber and Louis, "Botulinum Toxin Type a Therapy and Human Serum Albumin", Anesthesiology, vol. 104, No. 5, pp. 1108-1109 (2006).
Turton et al., "Botulinum and Tetanus Neurotoxins: Structure, Function and Therapeutic Utility", Trends Biochem. Sci., vol. 27, No. 11, pp. 552-558, 27(11) (2002).
van Ingen, "Sisterna: Sucrose esters, not a 'sweet' solution", White Paper, Flavours of Asia, pp. 1-11, downloaded 2013 from flavours.asia/uploads/7/9/8/9/7/7989988/white_paper_-_sucrose_esters_not_a_sweet_solution.

(56) References Cited

OTHER PUBLICATIONS

Veeratterapillay et al., "Discontinuation Rates and Inter-Injection Interval for Repeated Intravesical Botulinum Toxin Type A Injections for Detrusor Overactivity", Int. J. Urol., vol. 21, No. 2, pp. 175-178 (2014).

Walle et al., "Align-m A New Algorithm for Multiple Alignment of Highly Divergent Sequences", Bioinformatics, vol. 20, No. 9, pp. 1428-1435 (2004).

Williamson et al., "Clostridial Neurotoxins and Substrate Proteolysis in Intact Neurons: Botulinum Neurotoxin C Acts on Synaptosomal-Associated Protein of 25 kDa", J. Biol. Chem., vol. 271, No. 13, pp. 7694-7699 (1996).

Yowler et al., "Botulinum Neurotoxin A Activity Is Dependent Upon the Presence of Specific Gangliosides in Neuroblastoma Cells Expressing Synaptotagmin I", J. Biol. Chem., vol. 277, No. 36, pp. 32815-32819 (2002).

Rodriguez, T., BOTOX Fights Depression, Scientific American, 2012, 1-6, retrieved from https://www.scientificamerican.com/article/botox-fights-depression/, on Jan. 12, 2021.

Pokushalov, E., et al., Long-Term Suppression of Atrial Fibrillation by Botulinum Toxin Injection Into Epicardial Fat Pads in Patients Undergoing Cardiac Surgery One-Year Follow-Up of a Randomized Pilot Study, Circ Arrhythm Electrophysiol, 2015, 1334-1341, 8.

Ansel, Howard, Pharmaceutical Dosage Forms and Drug Delivery Systems, 1999, 2 Pages, 7th edition, Lippincott Williams & Wilkins.

Gennaro, Alfonso R., Pharmaceutical Sciences, Remington's 17th Edition, 1985, Mack Publishing Company, Easton, PA.

Gennaro, Alfonso, Remington: The Science and Practice, 2000, 2 Pages, 20th edition, Lippincott Williams & Wilkins.

Goodman & Gilman's The Pharmacological Basis of Therapeutics, 10th Edition, McGraw-Hill, 2001, 2 pages.

Schantz, E., et al., Preparation and Characterization of Botulinum Toxin Type A for Human Treatment, Neurological Disease & Therapy, 1994, 41-49, 25.

Wieder, J., et al., Understanding Botulinum Toxin, Derma. Surg., 1998, 1172-1174, 24.

Whelan et al., "The complete amino acid sequence of the Clostridium botulinum type-E neurotoxin, derived by nucleotide-sequence analysis of the encoding gene," European Journal of Biochemistry 204 (1992): 657-667.

NON-PROTEIN CLOSTRIDIAL TOXIN COMPOSITIONS

CROSS-REFERENCE TO RELATED APPLICATIONS

This application is a divisional of U.S. patent application Ser. No. 17/185,312, filed Feb. 25, 2021, which is a continuation of U.S. patent application Ser. No. 16/531,800, filed Aug. 5, 2019, which is a divisional of U.S. patent application Ser. No. 15/703,527, filed Sep. 13, 2017, which claims the benefit of U.S. Provisional Application No. 62/394,009, filed Sep. 13, 2016, the entire content of each application is incorporated herein by reference.

TECHNICAL FIELD

The present disclosure relates to solid and liquid pharmaceutical compositions comprising a Clostridial toxin active ingredient and one or more non-protein excipient.

BACKGROUND

A pharmaceutical composition is a formulation which contains at least one active ingredient (such as a Clostridial toxin) as well as, for example, one or more excipients, buffers, carriers, stabilizers, preservatives and/or bulking agents, and is suitable for administration to a patient to achieve a desired diagnostic result or therapeutic effect. The pharmaceutical compositions disclosed herein have diagnostic, therapeutic and/or research utility.

For storage stability and convenience of handling, a pharmaceutical composition can be formulated as a lyophilized (i.e. freeze dried) or vacuum dried powder which can be reconstituted with a suitable fluid, such as saline or water, prior to administration to a patient. Alternately, the pharmaceutical composition can be formulated as an aqueous solution or suspension. A pharmaceutical composition can contain a proteinaceous active ingredient. Unfortunately, a protein active ingredient can be very difficult to stabilize (i.e. maintained in a state where loss of biological activity is minimized), thereby resulting in a loss of protein and/or loss of protein activity during the formulation, reconstitution (if required) and storage of the pharmaceutical composition prior to use. Stability problems can arise due to surface adsorption of a protein active ingredient, physical instability, such as, e.g., denaturation or aggregation, or chemical instability, such as, e.g., cross-linking, deamidation, isomerization, oxidation, formation of acidic or basic species, Maillard reaction, and fragmentation. To prevent such instability, various protein-based excipients, such as albumin and gelatin, have been used to stabilize a protein active ingredient present in a pharmaceutical composition.

Unfortunately, despite their known stabilizing effects, significant drawbacks exist to the use of protein excipients, such as albumin or gelatin, in a pharmaceutical composition. For example, albumin and gelatin are expensive and increasingly difficult to obtain. Furthermore, blood products or animal derived products such as albumin and gelatin, when administered to a patient can subject the patient to a potential risk of receiving blood borne pathogens or infectious agents. Thus, it is known that the possibility exists that the presence of an animal-derived protein excipient in a pharmaceutical composition can result in inadvertent incorporation of infectious elements into the pharmaceutical composition. For example, it has been reported that use of human serum albumin may transmit prions into a pharmaceutical composition. Thus, it is desirable to find suitable non-protein excipients, such as, e.g., stabilizers, cryo-protectants and lyoprotectants, which can be used to stabilize the protein active ingredient present in a pharmaceutical composition.

The unique characteristics of Clostridial toxins further constrain and hinder the selection of suitable non-protein excipients for a pharmaceutical composition comprising a Clostridial toxin. For example, Clostridial toxins are large proteins having an average molecular weight of approximately 150 kDa, and are further complexed with non-toxin associated proteins that increase the size to approximately 300-900-kDa. The size of a Clostridial toxin complex makes it much more fragile and labile than smaller, less complex proteins, thereby compounding the formulation and handling difficulties if Clostridial toxin stability is to be maintained. Hence, the use of non-protein excipients, such as, e.g., stabilizers, cryo-protectants and lyoprotectants must be able to interact with the Clostridial toxin in a manner which does not denature, fragment or otherwise inactivate the toxin or cause disassociation of the non-toxin associated proteins present in the toxin complex.

Another problem associated with a Clostridial toxin, is the exceptional safety, precision, and accuracy that is necessary for at all steps of the formulation process. Thus, a non-protein excipient should not itself be toxic or difficult to handle so as to not exacerbate the already extremely stringent requirements.

Still another difficulty linked with a Clostridial toxin, is the small amount of Clostridial toxin that is used in a pharmaceutical composition. As with enzymes generally, the biological activities of the Clostridial toxins are dependent, at least in part, upon their three-dimensional conformation. Thus, a Clostridial toxin is detoxified by heat, various chemicals, surface stretching, and surface drying. Additionally, it is known that dilution of a Clostridial toxin complex obtained by the known culturing, fermentation and purification methods to the much lower concentration used in a pharmaceutical composition results in rapid inactivation of the toxin. The low amount of a Clostridial toxin that is used in a pharmaceutical composition, makes this active ingredient very susceptible to adsorption to, e.g., the surfaces of laboratory glassware, vessels, to the vial in which the pharmaceutical composition is reconstituted and to the inside surface of a syringe used to inject the pharmaceutical composition. Such adsorption of a Clostridial toxin to surfaces can lead to a loss of active ingredient and to denaturation of the remaining Clostridial toxin, both of which reduce the total activity of the active ingredient present in the pharmaceutical composition. Hence, the use of non-protein excipients, such as, e.g., stabilizers, cryo-protectants and lyoprotectants must be able to act as surface blockers to prevent the adsorption of a Clostridial toxin to a surface.

Yet another problem connected to a Clostridial toxin, is the pH-sensitivity associated with complex formation. For example, the 900-kDa BoNT/A complex is known to be soluble in dilute aqueous solutions at pH 3.5-6.8. However, at a pH above about 7 the non-toxic associated proteins dissociate from the 150-kDa neurotoxin, resulting in a loss of toxicity, particularly as the pH rises above pH 8.0. See Edward J. Schantz et al., pp. 44-45, *Preparation* and *characterization of botulinum* toxin *type A for human treatment*, in Jankovic, J., et al., Therapy with Botulinum Toxin (Marcel Dekker, Inc., 1994). As the non-toxic associated proteins are believed to preserve or help stabilize the secondary and tertiary structures upon which toxicity depends, the dissociation of these proteins results in a more unstable Clostridial toxin. Thus, non-protein excipients useful to formulate a pharmaceutical composition comprising a Clostridial toxin must be able to operate within the confines of a pH level necessary to maintain the activity a Clostridial toxin.

What is needed therefore is a Clostridial toxin pharmaceutical composition wherein a Clostridial toxin active ingredient (such as a botulinum toxin) is stabilized by a non-protein excipient. The present compositions relate to solid and liquid Clostridial toxin active ingredient pharmaceutical compositions with one or more non-protein excipients which functions to stabilize the Clostridial toxin active ingredient present in the solid or liquid pharmaceutical composition.

BRIEF SUMMARY

In one aspect, a pharmaceutical composition comprising a Clostridial toxin active ingredient, a tonicity agent, a surfactant and an antioxidant is provided.

In another aspect, a pharmaceutical composition comprising a Clostridial toxin active ingredient, a surfactant and an antioxidant is provided.

In another aspect, a pharmaceutical composition comprising a Clostridial toxin active ingredient, a lyoprotector, a surfactant and an antioxidant is provided.

In some embodiments, the pharmaceutical compositions comprise a botulinum toxin. In some embodiments, the pharmaceutical composition comprises trehalose. In some embodiments, the pharmaceutical composition comprises sodium chloride. In some embodiments, the composition comprises a poloxamer and/or a polysorbate. In some embodiments, the composition comprises poloxamer 188 and/or polysorbate 20. In some embodiments, the antioxidant is selected from the group consisting of L-methionine, N-acetyl-cysteine (NAC), butylated hydroxytoluene (BHT), ethylene diamine tetraacetic acid sodium salt (EDTA), an EDTA analog, ethylene glycol-bis(2-aminoethylether)-N,N,N',N'-tetraacetic acid (EGTA), an EGTA analog, diethylenetriaminepentaacetic acid (DTPA), a DTPA analog, ascorbic acid, and combinations thereof. In some embodiments, the composition further comprises a buffering agent. In one embodiment, the buffering agent includes histidine buffer. In some embodiments, the composition has a pH of from 5 to 7. In some embodiments, the composition is a liquid formulation. In some embodiments, the composition is a solid lyophilized formulation.

In another aspect, a liquid pharmaceutical composition comprising a Clostridial toxin active ingredient, trehalose, a poloxamer or a polysorbate, and L-methionine or NAC is provided. In some embodiments, the liquid pharmaceutical composition comprises a botulinum toxin. In some embodiments, the liquid pharmaceutical composition further comprises EDTA, EGTA, DTPA or analogs thereof. In some embodiments, the liquid pharmaceutical composition comprises a histidine buffer. In some embodiments, the pH of the liquid pharmaceutical composition ranges from 5 to 7. In some embodiments, the relative weight amount of L-methionine ranges from about 0.1% to about 0.3%. In some embodiments, the relative weight amount of NAC ranges from about 0.1% to about 0.5%. In some embodiments, the relative weight amount of EDTA ranges from about 0.01% to about 0.05%. In some embodiments, the relative weight amount of trehalose ranges from about 1.0 to about 10%. In some embodiments, the relative weight amount of poloxamer 188 ranges from about 0.5% to about 5%. In some embodiments, the relative weight amount of polysorbate ranges from about 0.02% to about 0.06%.

In another embodiment, a liquid pharmaceutical composition is provided. The composition comprises a Clostridial toxin active ingredient; a tonicity agent selected from trehalose, sucrose and combinations thereof, a surfactant selected from a poloxamer, a polysorbate and combinations thereof, and an antioxidant selected from methionine, NAC, ascorbic acid, butylated hydroxytoluene, EDTA, EGTA, DTPA, analogs thereof, and combinations thereof. In one embodiment, the composition excludes albumin, and in another embodiment, when the antioxidant is methionine the composition excludes a polysorbate. In one embodiment, the composition excludes animal protein stabilizers.

In another embodiment, a liquid pharmaceutical composition is contemplated. The composition comprises a Clostridial toxin active ingredient; a surfactant selected from a poloxamer, a polysorbate and combinations thereof; and an antioxidant selected from methionine, NAC, EDTA, EGTA, DTPA, analogs thereof, and combinations thereof. In one embodiment, the composition excludes albumin.

In another embodiment, the liquid composition is an animal protein free composition that comprises a botulinum toxin, a poloxamer, and methionine, and optionally includes a disaccharide. In one embodiment, the liquid composition excludes a disaccharide.

In a further embodiment, the liquid composition is an animal protein free composition that comprises a botulinum toxin, a surfactant selected from a poloxamer, a polysorbate and combinations thereof; and an antioxidant selected from the group consisting of a chelating agent, a sacrificial antioxidant, a chain terminator, and combinations thereof. In one embodiment, the antioxidant includes a combination of a chelating agent and a chain terminator.

In yet another embodiment, the liquid composition is an animal-protein free composition comprising a botulinum toxin, a poloxamer surfactant, and methionine, and optionally a disaccharide. In one embodiment, the liquid composition excludes a disaccharide.

In another embodiment, a liquid pharmaceutical composition is contemplated. The composition comprises a Clostridial toxin active ingredient; trehalose or sucrose; a poloxamer; and methionine. In one embodiment, the composition excludes albumin.

In another embodiment, a liquid pharmaceutical composition is contemplated. The composition comprises a Clostridial toxin active ingredient, trehalose in an amount between 1-15 wt %; a poloxamer in an amount between 0.5-8 wt %; and methionine in an amount between 0.05-5 wt %. In one embodiment, the composition excludes albumin.

In another embodiment, a liquid pharmaceutical composition is contemplated. The composition comprises a botulinum toxin; a disaccharide; a poloxamer; and an antioxidant selected from methionine, NAC, ascorbic acid, butylated hydroxytoluene, EDTA, EGTA, DTPA, analogs thereof, and combinations thereof. In one embodiment, the composition excludes albumin.

In another embodiment, the liquid composition is an animal protein free composition that comprises a botulinum toxin; a disaccharide; a poloxamer; and an antioxidant selected from the group consisting of a chelating agent, a sacrificial antioxidant, a chain terminator, and combinations thereof.

In another embodiment, a liquid composition comprised of a Clostridial toxin active ingredient, a poloxamer, a chelating agent and a chain terminator is provided.

In another embodiment, a liquid composition comprised of a Clostridial toxin active ingredient; a poloxamer; a chelating agent selected from EDTA, EGTA, DTPA and analogs thereof, and NAC is provided.

In another embodiment, a liquid composition comprised of a Clostridial toxin active ingredient, a poloxamer, and methionine is provided.

In another embodiment, a liquid composition comprised of a Clostridial toxin active ingredient, a tonicity agent selected from trehalose, sucrose and combinations thereof, a surfactant selected from a poloxamer, a polysorbate and combinations thereof, a chelating agent and a chain terminator is provided.

In another embodiment, a liquid composition comprised of a Clostridial toxin active ingredient; a tonicity agent selected from trehalose, sucrose and combinations thereof; a surfactant selected from a poloxamer, a polysorbate and combinations thereof; a chelating agent selected from EDTA, EGTA, DTPA and analogs thereof, and NAC, is provided.

In any of the foregoing embodiments, it is contemplated that the composition is not, in some embodiments, an emulsion and/or excludes nanoparticles comprising an amphiphilic entity.

In another aspect, the present disclosure provides a solid pharmaceutical composition comprising a botulinum toxin; trehalose; a poloxamer or a polysorbate; NAC; and a chelating agent selected from EDTA, EGTA, DTPA and analogs thereof. In an alternative embodiment, the solid pharmaceutical composition comprises a botulinum toxin, trehalose, a poloxamer and L-methionine. In some embodiments, the solid pharmaceutical composition further comprises histidine buffer. In some embodiments, the relative weight amount of L-methionine ranges from about 0.1% to about 0.3%. In some embodiments, the relative weight amount of NAC ranges from about 0.01% to about 0.5%. In some embodiments, the relative weight amount of EDTA ranges from about 0.01% to about 0.05%. In some embodiments, the relative weight amount of trehalose ranges from about 1.0 to about 10%. In some embodiments, the relative weight amount of poloxamer ranges from about 0.5% to about 5%. In some embodiments, the relative weight amount of polysorbate ranges from about 0.02% to about 0.06%.

In one embodiment, a solid or lyophilized pharmaceutical composition is contemplated. The composition comprises a Clostridial toxin active ingredient; a disaccharide selected from trehalose, sucrose and combinations thereof, a surfactant selected from a poloxamer, a polysorbate and combinations thereof; and an antioxidant selected from methionine, N-acetyl cysteine, BHT, EDTA, EGTA, DTPA, ascorbic acid, analogs thereof, and combinations thereof. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, the solid or lyophilized composition is an animal protein free composition that comprises a botulinum toxin; a disaccharide selected from trehalose, sucrose and combinations thereof, a surfactant selected from a poloxamer, a polysorbate and combinations thereof; and an antioxidant selected from the group consisting of a chelating agent, a sacrificial antioxidant, a chain terminator, and combinations thereof.

In another embodiment, a solid or lyophilized pharmaceutical composition is contemplated. The composition comprises a Clostridial toxin active ingredient; trehalose or sucrose; a poloxamer; and methionine. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, a solid or lyophilized pharmaceutical composition is contemplated. The composition comprises a Clostridial toxin active ingredient; trehalose in an amount between 1-15 wt %; a poloxamer in an amount between 0.5-8 wt %; and methionine in an amount between 0.05-5 wt %. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, a solid or lyophilized pharmaceutical composition is contemplated. The composition comprises a botulinum toxin; a disaccharide; a poloxamer; and an antioxidant selected from methionine, N-acetyl cysteine, EDTA, EGTA, DTPA, analogs thereof, and combinations thereof. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, the solid or lyophilized composition is an animal protein free composition that comprises a botulinum toxin, a disaccharide, a poloxamer; and an antioxidant selected from the group consisting of a chelating agent, a sacrificial antioxidant, a chain terminator, and combinations thereof.

In another embodiment, a lyophilized composition comprised of a Clostridial toxin active ingredient; a lyoprotector selected from sucrose, trehalose, mannitol, sorbitol, glucose, and combinations thereof, a surfactant selected from a poloxamer, a polysorbate and combinations thereof; a chelating agent; and a chain terminator; is provided.

In another embodiment, a lyophilized composition comprised of a Clostridial toxin active ingredient; a lyoprotector selected from sucrose, trehalose, mannitol, sorbitol, glucose, and combinations thereof, a surfactant selected from a poloxamer, a polysorbate and combinations thereof, a chelating agent selected from EDTA, EGTA, DTPA, and analogs thereof, and NAC; is provided.

In another embodiment, a lyophilized composition comprised of a Clostridial toxin active ingredient; a lyoprotector selected from sucrose, trehalose, mannitol, sorbitol, glucose, and combinations thereof, a poloxamer; and a chain terminator is provided. In one embodiment, the lyophilized composition excludes a chelating agent. In one embodiment, the chain terminator is NAC.

In another embodiment, a lyophilized composition comprised of a Clostridial toxin active ingredient; a lyoprotector selected from sucrose, trehalose, mannitol, sorbitol, glucose, and combinations thereof, a poloxamer; and methionine is provided.

In another embodiment, a lyophilized composition comprised of a Clostridial toxin active ingredient; a lyoprotector selected from sucrose, trehalose, mannitol, sorbitol, glucose, and combinations thereof; a poloxamer; a chelating agent; and a chain terminator is provided.

In another embodiment, a lyophilized composition comprised of a Clostridial toxin active ingredient; a lyoprotector selected from sucrose, trehalose, mannitol, sorbitol, glucose, and combinations thereof, a poloxamer; a chelating agent selected from EDTA, EGTA, DTPA and analogs thereof, and NAC is provided.

In another embodiment, the lyophilized composition is an animal protein free composition that comprises a Clostridial toxin active ingredient; a lyoprotector selected from sucrose, trehalose, mannitol, sorbitol, glucose, and combinations thereof, a poloxamer; and NAC; and optionally includes EDTA, EGTA, DTPA or analogs thereof. In one embodiment, the lyophilized composition excludes EDTA, EGTA, DTPA and analogs thereof.

In another embodiment, a lyophilized composition comprised of a Clostridial toxin active ingredient; a lyoprotector selected from sucrose, trehalose, mannitol, sorbitol, glucose, and combinations thereof, a surfactant selected from a poloxamer, a polysorbate and combinations thereof, and NAC is provided.

In certain embodiments, the lyophilized composition is reconstituted with a tonicity agent selected from trehalose, sucrose, sodium chloride, mannitol, sorbitol, glucose, and combinations thereof. In at least one embodiment, the lyophilized composition is reconstituted with a reconstitution vehicle comprising NaCl prior to administration to a patient.

In any of the foregoing embodiments of solid or liquid compositions, it is contemplated that one or more, in any combination, of these ingredients are excluded polyvinylpyrrolidone, diblock copolymers of polypropylene glycol and polyethylene glycol, and/or a polyalcohol such as inositol, lactitol, isomalt, xylitol, erythritol. In any of the foregoing embodiments of solid or liquid compositions, it is contemplated that the composition is free of animal proteins.

In another aspect, a pharmaceutical composition comprising a Clostridial toxin active ingredient; a tonicity agent and/or a lyoprotector selected from trehalose, sucrose and combinations thereof; a surfactant selected from a poloxamer, a polysorbate and combinations thereof, and an antioxidant selected from methionine, N-acetyl cysteine, EDTA, EGTA, DTPA, analogs thereof, and combinations thereof, is contemplated. In one embodiment, the composition excludes albumin, and in embodiments when the composition is a liquid and the antioxidant is methionine, the surfactant excludes a polysorbate. The composition can be liquid or solid.

In another aspect, a pharmaceutical composition is contemplated. The composition comprises a Clostridial toxin active ingredient; trehalose or sucrose; a poloxamer; and methionine. In one embodiment, the composition excludes albumin. The composition can be liquid or solid.

In another aspect, a pharmaceutical composition is contemplated. The composition comprises a Clostridial toxin active ingredient, trehalose in an amount between 1-15 wt %, a poloxamer in an amount between 0.5-8 wt %, and methionine in an amount between 0.05-5 wt %. In one embodiment, the composition excludes albumin. The composition can be liquid or solid.

In another aspect, a pharmaceutical composition is contemplated. The composition comprises a botulinum toxin; a disaccharide; a poloxamer; and an antioxidant selected from methionine, NAC, EDTA, EGTA, DTPA, analogs thereof, and combinations thereof. In one embodiment, the composition excludes albumin. The composition can be liquid or solid.

In another aspect, a pharmaceutical composition comprising a Clostridial toxin active ingredient; a surfactant selected from a poloxamer, a polysorbate and combinations thereof; and an antioxidant selected from methionine, N-acetyl cysteine, EDTA, EGTA, DTPA, analogs thereof, and combinations thereof, is provided. In one embodiment, the composition excludes albumin, and in embodiments when the composition is a liquid and the antioxidant is methionine, the surfactant excludes a polysorbate. The composition can be liquid or solid. In one embodiment, the composition further comprises a tonicity agent and/or a lyoprotector. In some embodiments, the tonicity agent is selected from trehalose, sucrose, sodium chloride, mannitol, sorbitol, glucose, and combinations thereof. In alternative embodiments, the lyoprotector is selected from trehalose, sucrose, mannitol, sorbitol, glucose, and combinations thereof. In one embodiment, the tonicity agent and/or lyoprotector is a disaccharide. In one embodiment, the disaccharide is selected from trehalose and sucrose.

In another aspect, a method for treating depression is contemplated. The method comprises providing for administration, instructing to administer, or administering a composition according to any of the embodiments and aspects described herein.

In another aspect, a method for treating cardiac arrhythmia is contemplated. The method comprises providing for administration, instructing to administer, or administering a composition according to any of the embodiments and aspects described herein.

DETAILED DESCRIPTION

Compositions described herein, in embodiments, are directed to stable liquid and/or stable solid pharmaceutical compositions of a Clostridial toxin active ingredient, where the composition comprises, in some embodiments, a surfactant and an antioxidant, and optionally a tonicity agent and/or a lyoprotector. In certain liquid compositions, the disaccharide is optional.

Also as will be described below, the compositions are useful in methods for the treatment of various diseases, disorders, and conditions, including, for example, depression (e.g. major depressive disorder), headache (e.g. migraine, tension headache, and the like), pain, atrial fibrillation, hyperhidrosis, muscle spasticity, cervical dystonia, blepharospasm, overactive bladder (e.g. neurogenic detrusor over-activity, and idiopathic overactive bladder), bladder pain (e.g. interstitial cystitis, and bladder pain syndrome), skin conditions (e.g. wrinkles, fine wrinkles, excess sebum production, acne, and rosacea), irregularities, and the like using the compositions provided herein. Embodiments can include various administration techniques, including, for example, injection, such as intramuscular, intracutaneous, subcutaneous, or the like, instillation, intravenous, transdermal, and topical.

Definitions

As used herein, the words or terms set forth below have the following definitions:

The articles "a" and "an" are used herein to refer to one or to more than one (i.e., to at least one) of the grammatical object of the article. By way of example, "an element" means one element or more than one element.

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value. The term "about" when qualifying a value of a stated item, number, percentage, or term refers to a range of plus or minus ten percent of the value of the stated item, percentage, parameter, or term.

"Administration", or "to administer" means the step of giving (i.e. administering) a pharmaceutical composition to a subject, or alternatively a subject receiving a pharmaceutical composition. The pharmaceutical compositions disclosed herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

"Alleviating" means a reduction in the occurrence of a pain, of a headache, or of any symptom or cause of a condition or disorder. Thus, alleviating includes some reduction, significant reduction, near total reduction, and total reduction.

"Animal protein free" means the absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal protein free pharmaceutical composition can include a botulinum neurotoxin. For example, an "animal protein free" pharmaceutical composition means a pharmaceutical composition which is either substantially free or essentially free or entirely free of a serum derived albumin, gelatin and other animal derived proteins, such as immunoglobulins. An example of an animal protein free pharmaceutical composition is a pharmaceutical composition which comprises or which consists of a botulinum toxin (as the active ingredient) and a suitable polysaccharide as a stabilizer or excipient.

"Antioxidant" refers to any compound which protects an active ingredient from reaction with oxygen. Antioxidants can be broadly divided into three categories: (i) sacrificial antioxidants, which react with oxygen more readily than a particular active ingredient and therefore can scavenge oxygen, e.g., ascorbic acid and sulfites; (ii) chain terminators, which are molecules that form stable radicals due to weak bonds to hydrogen atoms that are attacked in a propagation of radical chains by consumption of oxygen, e.g., methionine, NAC, glutathionine, lipoic acid, butylated hydroxytoluene (BHT), and cysteine, (iii) chelating agents, which reduce catalytic activity of transition metals by forming complexes with the metals, e.g., EDTA, EGTA and DTPA and analogs thereof.

"Biological activity" describes the beneficial or adverse effects of a drug on living matter. When a drug is a complex chemical mixture, this activity is exerted by the substance's active ingredient but can be modified by the other constituents. Biological activity can be assessed as potency or as toxicity by an in vivo $LD_{50}$ or $ED_{50}$ assay, or through an in vitro assay such as, for example, cell-based potency assays as described in U.S. 2010/0203559 and U.S. 2010/0233802.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G, and their subtypes and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 600 and 900 kDa complexes), as well as the neurotoxic component of the botulinum toxin (150 kDa) that is unassociated with the complex proteins.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxins include Botulinum toxins, such as a BoNT/A, a BoNT/B, a BoNT/$C_1$, a BoNT/D, a BoNT/E, a BoNT/F, a BoNT/G, a Tetanus toxin (TeNT), a Baratii toxin (BaNT), and a Butyricum toxin (BuNT). The BoNT/$C_2$ cytotoxin and BoNT/$C_3$ cytotoxin, not being neurotoxins, are excluded from the term "Clostridial toxin." The term Clostridial toxin also includes the approximately 150-kDa Clostridial toxin alone (i.e. without the NAPs). A Clostridial toxin includes naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. A Clostridial toxin also includes Clostridial toxin complexes, which refers to a complex comprising a Clostridial toxin and non-toxin associated proteins (NAPs), such as, e.g., a Botulinum toxin complex, a Tetanus toxin complex, a Baratii toxin complex, and a Butyricum toxin complex. Non-limiting examples of Clostridial toxin complexes include those produced by a *Clostridium botulinum*, such as, e.g., a 900-kDa BoNT/A complex, a 500-kDa BoNT/A complex, a 300-kDa BoNT/A complex, a 500-kDa BoNT/B complex, a 500-kDa BoNT/$C_1$ complex, a 500-kDa BoNT/D complex, a 300-kDa BoNT/D complex, a 300-kDa BoNT/E complex, and a 300-kDa BoNT/F complex.

"Clostridial toxin active ingredient" refers to a molecule which contains any part of a Clostridial toxin that exerts an effect upon or after administration to a subject or patient. As used herein, the term "Clostridial toxin" encompasses (i) a Clostridial toxin complex comprising the approximately 150-kDa Clostridial toxin and other proteins collectively called non-toxin associated proteins (NAPs), (ii) the approximately 150-kDa Clostridial toxin alone (i.e. without the NAPs), or (iii) a modified Clostridial toxin, such as, e.g., a re-targeted Clostridial toxins.

"Deformity" means a cosmetic, physical or functional irregularity, defect, abnormality, imperfection, malformation, depression, or distortion.

"Effective amount" as applied to the biologically active ingredient means that amount of the ingredient which is generally sufficient to effect a desired change in the subject. For example, where the desired effect is a reduction in an autoimmune disorder symptom, an effective amount of the ingredient is that amount which causes at least a substantial reduction of the autoimmune disorder symptom, and without resulting in significant toxicity.

"Effective amount" when used in reference to the amount of an excipient or specific combination of excipients added to a Clostridial toxin composition, refers to the amount of each excipient that is necessary to achieve the desired initial recovered potency of a Clostridial toxin active ingredient. In aspects of this embodiment, an effective amount of an excipient or combination of excipients results in an initial recovered potency of, e.g., at least 10%, at least 20%, at least 30%, at least 40%, at least 50%, at least 60%, at least 70%, at least 80%, at least 90% or at least 100%. In other aspects of this embodiment, a therapeutically effective concentration of a Clostridial toxin active ingredient reduces a symptom associated with the aliment being treated by, e.g., at most 10%, at most 20%, at most 30%, at most 40%, at most 50%, at most 60%, at most 70%, at most 80%, at most 90% or at most 100%.

"Heavy chain" means the heavy chain of a botulinum neurotoxin. It has a molecular weight of about 100 kDa and can be referred to as the H chain, or as H.

$H_C$ means a fragment (about 50 kDa) derived from the H chain of a botulinum neurotoxin which is approximately equivalent to the carboxyl end segment of the H chain, or the portion corresponding to that fragment in the intact H chain. It is believed to be immunogenic and to contain the portion of the natural or wild type botulinum neurotoxin involved in high affinity, presynaptic binding to motor neurons.

$H_N$ means a fragment (about 50 kDa) derived from the H chain of a botulinum neurotoxin which is approximately equivalent to the amino end segment of the H chain, or the portion corresponding to that fragment in the intact in the H chain. It is believed to contain the portion of the natural or wild type botulinum neurotoxin involved in the translocation of the L chain across an intracellular endosomal membrane.

"Light chain" means the light chain of a Clostridial neurotoxin. It has a molecular weight of about 50 kDa, and can be referred to as the L chain, L, or as the proteolytic domain (amino acid sequence) of a botulinum neurotoxin.

$LH_N$ or $L-H_N$ means a fragment derived from a Clostridial neurotoxin that contains the L chain, or a functional fragment thereof coupled to the $H_N$ domain It can be obtained from the intact Clostridial neurotoxin by proteolysis, so as to remove or to modify the $H_C$ domain.

"Implant" means a controlled release (e.g., pulsatile or continuous) composition or drug delivery system. The implant can be, for example, injected, inserted or implanted into a human body.

"Liquid composition", "liquid pharmaceutical composition", or "liquid formulation" refers to a pharmaceutically active preparation of drug or biological which is capable of being stored in a liquid pharmaceutical excipient, such as a buffering agent, for an extended period of time, such that it can be ready-to-use as needed by a clinician. The liquid pharmaceutical composition is manufactured without a lyophilization process.

"Local administration" means direct administration of a pharmaceutical at or to the vicinity of a site on or within an animal body, at which site a biological effect of the pharmaceutical is desired, such as via, for example, intramuscular or intra- or subdermal injection or topical administration. Local administration excludes systemic routes of administration, such as intravenous or oral administration. Topical administration is a type of local administration in which a pharmaceutical agent is applied to a patient's skin.

"Lyoprotector" or "lyoprotectant" means a substance that is included in a lyophilized formulation to protect a Clostridial toxin active ingredient during the freeze-drying process. Lyoprotectors include for example polyhydroxy compounds such as sugars (mono-, di-, and polysaccharides), polyalcohols, and their derivatives. Exemplary lyoprotectors which can be used with the lyophilized formulations disclosed herein include sucrose, trehalose, mannitol, sorbitol, glucose, raffinose, maltose, glycerol, lactose, fructose, galactose, and combinations thereof.

"Lyophilized composition", "lyophilized pharmaceutical composition", "lyophilized formulation", or "solid composition" refers to a formulation containing a Clostridial toxin active ingredient which has been subjected to a lyophilization, freeze-drying or vacuum-drying process; and can be reconstituted with a reconstitution vehicle, such as for example saline or water, prior to administration to a patient. The lyophilized composition can be a freeze-dried composition or a vacuum-dried composition.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, asparagine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Patient" means a human or non-human subject receiving medical or veterinary care. Accordingly, the compositions as disclosed herein can be used in treating any animal, such as, for example, mammals, or the like.

"Peripherally administering" or "peripheral administration" means subdermal, intradermal, transdermal, or subcutaneous administration, but excludes intramuscular administration. "Peripheral" means in a subdermal location, and excludes visceral sites.

"Pharmaceutical composition" means a composition comprising an active pharmaceutical ingredient, such as, for example, a Clostridial toxin active ingredient such as a botulinum toxin, and at least one additional ingredient, such as, for example, a stabilizer or excipient or the like. A pharmaceutical composition is therefore a formulation which is suitable for diagnostic or therapeutic administration to a subject, such as a human patient. The pharmaceutical composition can be, for example, in a lyophilized or vacuum dried condition, a solution formed after reconstitution of the lyophilized or vacuum dried pharmaceutical composition, or as a solution or solid which does not require reconstitution.

"Pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyoprotectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical composition comprising a Clostridial toxin active ingredient can include one or more pharmaceutically acceptable excipients that facilitate processing of an active ingredient into pharmaceutically acceptable compositions. Insofar as any pharmacologically acceptable excipient is not incompatible with the Clostridial toxin active ingredient, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003), each of which is hereby incorporated by reference in its entirety.

The constituent ingredients of a pharmaceutical composition can be included in a single composition (that is, all the constituent ingredients, except for any required reconstitution fluid, are present at the time of initial compounding of the pharmaceutical composition) or as a two-component system, for example a vacuum-dried composition reconstituted with a reconstitution vehicle which can, for example, contain an ingredient not present in the initial compounding of the pharmaceutical composition. A two-component system can provide several benefits, including that of allowing incorporation of ingredients which are not sufficiently compatible for long-term shelf storage with the first component of the two-component system. For example, the reconstitution vehicle may include a preservative which provides sufficient protection against microbial growth for the use period, for example one-week of refrigerated storage, but is not present during the two-year freezer storage period during which time it might degrade the toxin. Other ingredients, which may not be compatible with a botulinum toxin or other ingredients for long periods of time, can be incorporated in this manner; that is, added in a second vehicle (e.g. in the reconstitution vehicle) at the approximate time of use. A pharmaceutical composition can also include preservative agents such as benzyl alcohol, benzoic acid, phenol, parabens and sorbic acid. Pharmaceutical compositions can include, for example, excipients, such as surface active agents; dispersing agents; inert diluents; granulating and disintegrating agents; binding agents; lubricating agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, Remington's Pharmaceutical Sciences, Mack Publishing Co., Easton, Pa., which is incorporated herein by reference.

"Polysaccharide" means a polymer of more than two saccharide molecule monomers. The monomers can be identical or different.

"Stabilizing agent", "stabilization agent" or "stabilizer" means a substance that acts to stabilize a Clostridial toxin active ingredient such that the potency of the pharmaceutical composition is increased relative to an unstabilized composition.

"Stabilizers" can include excipients, and can include protein and non-protein molecules.

"Surfactant" refers to a natural or synthetic amphiphilic compound. A surfactant can be non-ionic, zwitterionic, or ionic. Non-limiting examples of surfactants include a poloxamer, a polysorbate, and combinations thereof.

"Therapeutic formulation" means a formulation can be used to treat and thereby alleviate a disorder or a disease, such as, for example, a disorder or a disease characterized by hyperactivity (i.e. spasticity) of a peripheral muscle.

Therapeutically effective concentration", "therapeutically effective amount," "effective amount," "effective dose," and "therapeutically effective dose" refer to the minimum dose of a Clostridial toxin active ingredient necessary to achieve the desired therapeutic effect and includes a dose sufficient to reduce a symptom associated with aliment being treated.

"TEM" as used herein, is synonymous with "Targeted Exocytosis Modulator" or "retargeted endopeptidase." Generally, a TEM comprises an enzymatic domain from a Clostridial toxin light chain, a translocation domain from a Clostridial toxin heavy chain, and a targeting domain. The targeting domain of a TEM provides an altered cell targeting capability that targets the molecule to a receptor other than the native Clostridial toxin receptor utilized by a naturally-occurring Clostridial toxin. This re-targeted capability is achieved by replacing the naturally-occurring binding domain of a Clostridial toxin with a targeting domain having a binding activity for a non-Clostridial toxin receptor. Although binding to a non-Clostridial toxin receptor, a TEM undergoes all the other steps of the intoxication process including internalization of the TEM/receptor complex into the cytoplasm, formation of the pore in the vesicle membrane and di-chain molecule, translocation of the enzymatic domain into the cytoplasm, and exerting a proteolytic effect on a component of the SNARE complex of the target cell.

"Tonicity agent" means a low molecular weight excipient which is included in a formulation to provide isotonicity. Non-limiting examples of a tonicity agent include a disaccharide such as trehalose or sucrose; a polyalcohol such as sorbitol or mannitol; a monosaccharide such as glucose; and a salt such as sodium chloride.

"Topical administration" excludes systemic administration of the neurotoxin. In other words, and unlike conventional therapeutic transdermal methods, topical administration of botulinum toxin does not result in significant amounts, such as the majority of, the neurotoxin passing into the circulatory system of the patient.

"Treating" means to alleviate (or to eliminate) at least one symptom of a condition or disorder, such as, for example, wrinkles, spasticity, depression, pain (such as, for example, headache pain), bladder overactivity, or the like, either temporarily or permanently.

As used herein, the term "unit" or "U" refers to the LD$_{50}$ dose or the dose determined by a cell based potency assay (CBPA). The LD$_{50}$ dose is defined as the amount of a Clostridial toxin active ingredient, Clostridial toxin complex or modified Clostridial toxin that killed 50% of the mice injected with the Clostridial toxin, Clostridial toxin complex or modified Clostridial toxin. The CBPA dose is determined as described in U.S. Pat. No. 8,618,261, the assay details of which are incorporated by reference herein.

"Variant" means a Clostridial neurotoxin, such as wild-type botulinum toxin serotype A, B, C, D, E, F or G, that has been modified by the replacement, modification, addition or deletion of at least one amino acid relative to wild-type botulinum toxin, which is recognized by a target cell, internalized by the target cell, and catalytically cleaves a SNARE (SNAP (Soluble NSF Attachment Protein) Receptor) protein in the target cell.

An example of a variant neurotoxin component can comprise a variant light chain of a botulinum toxin having one or more amino acids substituted, modified, deleted and/or added. This variant light chain may have the same or better ability to prevent exocytosis, for example, the release of neurotransmitter vesicles. Additionally, the biological effect of a variant may be decreased compared to the parent chemical entity. For example, a variant light chain of a botulinum toxin type A having an amino acid sequence removed may have a shorter biological persistence than that of the parent (or native) botulinum toxin type A light chain.

Pharmaceutical Compositions

In a first aspect, a pharmaceutical composition comprising (or consisting of, or consisting essentially of) a Clostridial toxin active ingredient, a disaccharide, a surfactant and an antioxidant is described. The composition can, in one embodiment, be a solid composition, such as a lyophilized powder that is reconstituted prior to use. In another embodiment, the composition is a liquid composition; that is, the composition is manufactured and stored in liquid form. Studies were conducted demonstrating that the compositions stabilize the Clostridial toxin active ingredient to retain its potency, as will now be described with respect to Examples 1-11.

In one study, described in Example 1, compositions were prepared that comprised botulinum toxin as a model Clostridial toxin active ingredient, a disaccharide, a surfactant, and an antioxidant. The formulations were lyophilized and stored under various temperatures for selected periods of time, ranging from 1 month to 7.5 months. Potency of the lyophilized formulations after storage and reconstitution with saline was tested by a cell based potency assay. The results were normalized to target potency. The potencies of the solid compositions are shown in Tables 1.1, 1.2, 2 and 3.

TABLE 1

1-Lyophilized formulations

| Formulation | Excipient, % w/w | | | | | | | Normalized potency, storage at 25° C. | | |
| --- | --- | --- | --- | --- | --- | --- | --- | --- | --- | --- |
| | Treh | TWEEN® 20 | P 188 | NaCl | Met | NAC | Buffer | T0 | 3 mo | 6 mo |
| Comparator 1 | 3 | 0.04 | — | 0.9 | 0.2 | — | water | 80.6% | 86.4% | 80.8% |
| Comparator 2 | 2 | — | 4 | — | — | — | 20 mM Histidine pH 5.5 | 81.5% | 68.6% | 68.0% |
| Formulation 1 | 2 | — | 4 | — | — | 0.03 | 20 mM Histidine pH 5.5 | 98.6% | 91.9% | 86.9% |

Treh = trehalose;
P 188 = poloxamer P 188;
Met = L-methionine;
NAC = N-acetyl-L-cysteine.

TABLE 1

2-Lyophilized formulations

| Formulation | Excipient, % w/w | | | | | | | Normalized potency, storage at 40° C. | | |
| --- | --- | --- | --- | --- | --- | --- | --- | --- | --- | --- |
| | Treh | TWEEN® 20 | P 188 | NaCl | Met | NAC | Buffer | 1 mo | 3 mo | 6 mo |
| Comparator 1 | 3 | 0.04 | — | 0.9 | 0.2 | — | Water | 74.8% | 70.3% | 24.0% |
| Comparator 2 | 2 | — | 4 | — | — | — | 20 mM Histidine pH 5.5 | 64.8% | 57.8% | 46.8% |
| Formulation 1 | 2 | — | 4 | — | — | 0.03 | 20 mM Histidine pH 5.5 | 86.5% | 77.9% | 62.3% |

Treh = trehalose;
P 188 = poloxamer P 188;
Met = L-methionine;
NAC = N-acetyl-L-cysteine.

The data in Table 1.1 demonstrates that a lyophilized botulinum toxin composition comprised of trehalose, poloxamer, and NAC retained more than 8500 potency after storage for six months at 25° C. The formulation referred to as Comparator 2, which was identical to Formulation 1 except that it lacked an antioxidant (i.e., no methionine, no NAC), had only 68% retained potency after storage for six months at 25° C. Formulation 1 had about 7.5% higher potency than Comparator 1 after storage for six months at 25° C. (calculated as a percent difference, ((86.9%-80.8%)/80.8%)). Formulation 1 had 27.8% higher potency than Comparator 2 after storage for six months at 25° C. (calculated as a percent difference, ((86.9%-68%)/68%)). The data in Table 1.2 shows potency data for the same three formulations as Table 1.1 (Formulation 1 and Comparator 1 and Comparator 2), demonstrating that a lyophilized botulinum toxin composition comprised of trehalose, poloxamer, and NAC retained more than 60% potency after storage for six months at 40° C. The formulation referred to as Comparator 2, which was identical to Formulation 1 except that it lacked an antioxidant (e.g., no methionine, no NAC), had only 46.8% retained potency after storage for six months at 40° C. Formulation 1 had about 160% higher potency than Comparator 1 after storage for six months at 40° C. (calculated as a percent difference). Formulation 1 had about 33% higher potency than Comparator 2 after storage for six months at 40° C. (calculated as a percent difference). Accordingly, in one embodiment, a lyophilized composition is contemplated, where the composition is comprised of a Clostridial toxin active ingredient, such as a botulinum toxin; a disaccharide; a surfactant; and an antioxidant. In one embodiment, the composition retains potency after storage for six months at 25° C. that is at least about 15%, 20%, or 25% greater than a formulation lacking the antioxidant. In another embodiment, a lyophilized composition is contemplated, where the composition is comprised of a Clostridial toxin active ingredient, such as a botulinum toxin; a disaccharide; a surfactant; and an antioxidant. In one embodiment, the composition retains potency after storage for six months at 40° C. that is at least about 20%, 25%, or 30% greater than a formulation lacking the antioxidant. In another embodiment, a lyophilized composition is contemplated, where the composition is comprised of a Clostridial toxin active ingredient, such as a botulinum toxin; a disaccharide; a surfactant; and an antioxidant. In one embodiment, the composition retains at least about 55% or 60% potency after storage for six months at 40° C., where potency is measured in a cell-based potency assay.

It will be appreciated that potency of the Clostridial toxin can be ascertained in various ways, such as the in vitro cell-based potency assay used in the studies discussed herein or in an in vivo assay. An exemplary in vivo assay is the $LD_{50}$ potency assay, where the potency of the toxin is expressed as a multiple of the $LD_{50}$ value for a mouse, one unit (U) of toxin being defined as being the equivalent amount of toxin that kills 50% of a group of 18 to 20 female Swiss-Webster mice, weighing about 20 grams each. Any known method for assessing potency can be used to determine whether a composition or a particular composition components stabilize a toxin. The in vitro cell-based potency assay used herein is not intended to be limiting to the possible approaches to ascertain potency.

In another study, with continuing reference to Example 1, lyophilized botulinum toxin compositions were prepared with trehalose; a polysorbate or a poloxamer; and methionine or NAC. Comparator formulations were prepared with sucrose (Comparator 3) and with no antioxidant (Comparator 2). The lyophilized formulations and lyophilized comparator formulations were placed in storage for 1 month at −20° C. or at 40° C. Potency of the botulinum toxin was measured using a cell-based potency assay and the results are shown in Table 2.

TABLE 2

Lyophilized formulations

| | Excipient, % w/w | | | | | | | | Normalized potency (% of target) | | |
|---|---|---|---|---|---|---|---|---|---|---|---|
| Formulation | Treh | Sucr | TWEEN® 20 | P 188 | NaCl | Met | NAC | Buffer | T0 | 1 mo −20° C. | 1 mo 40° C. |
| Comparator 2 | 2 | | | 4 | | | | 20 mM Histidine pH 5.5 | 87.15% | 88.95% | 76.32% |
| Comparator 3 | | 3 | 0.04 | | 0.9 | 0.2 | | Water | 84.06% | 85.18% | 72.86% |
| Formulation 2 | 2 | | | 4 | | 0.2 | | 20 mM Histidine pH 6.0 | 98.60% | 120.85% | 91.17% |
| Formulation 3 | 8 | | 0.04 | | | | 0.03 | 20 mM Histidine pH 6.0 | 105.2% | 110.05% | 96.89% |

Treh = trehalose;
Sucr = sucrose;
P188 = poloxamer P 188;
Met = L-methionine;
NAC = N-acetyl-L-cysteine.

Inspection of the data in Table 2 for compositions identified as Formulation 2 and Comparator 2 demonstrates the stabilizing effect on the botulinum toxin by the combination of a disaccharide, a surfactant, and an antioxidant. Formulation 2 and Comparator 2 were identical in all respects other than Comparator 2 lacked an antioxidant. The potency data for these two compositions shows that the antioxidant acts to stabilize the toxin, as Formulation 2 retained more than 90% potency after storage for one month at 40° C. whereas the comparative formulation (Comparator 2) lacking the antioxidant had only 76% potency after storage for one month at 40° C. Formulation 3, comprised of trehalose, polysorbate surfactant (TWEEN®-20), and an antioxidant NAC, retained more than 95% potency after storage for one month at 40° C., considerably better than either comparative formulation. Accordingly, in one embodiment, a lyophilized composition is contemplated, where the composition is comprised of a Clostridial toxin active ingredient, such as a botulinum toxin; a disaccharide; a surfactant; and an antioxidant. In one embodiment, the composition retains at least about 80%, 85% or 90% potency after storage for one month at 40° C., where potency is measured in a cell-based potency assay. In another embodiment, a lyophilized composition is contemplated, where the composition is comprised of a Clostridial toxin active ingredient, such as a botulinum toxin; a disaccharide; a surfactant selected from a poloxamer and a polysorbate; and an antioxidant selected from methionine, NAC, EDTA, EGTA, DTPA, analogs thereof, and combinations thereof. In one embodiment, the composition retains at least about 80%, 85% or 90% potency after storage for one month at 40° C., where potency is measured in a cell-based potency assay. Such compositions, in another embodiment, retain potency after storage for one month at 40° C. that is at least about 18%, 20% or 24% greater than a formulation lacking the antioxidant.

With continued reference to Example 1, compositions comprised of a Clostridial toxin active ingredient (botulinum toxin), trehalose, a poloxamer surfactant (e.g. KOLLIPHOR® P-188) and methionine as a stabilizing antioxidant were prepared. A comparative formulation lacking the methionine was prepared (Comparator 2). The compositions were lyophilized and placed in storage for 7.5 months at 25° C. Potency of the botulinum toxin was measured after 3 months and after 7.5 months of storage using a cell-based potency assay and normalized to the target potency. The results are shown in Table 3.

TABLE 3

| Formulation | Lyophilized formulations Excipient, % w/w | | | | Normalized potency, storage at 25° C. | | |
|---|---|---|---|---|---|---|---|
| | Trehalose | P-188 | Met | Buffer | T0 | 3 mo | 7.5 mo |
| Comparator 2 | 2 | 4 | | 20 mM Histidine, pH 5.5 | 87.1% | 78.0% | 78.0% |
| Formulation 2 | 2 | 4 | 0.2 | 20 mM Histidine, pH 6.0 | 98.6% | 97.0% | 98.0% |
| Formulation 4 | 8 | 0.6 | 0.2 | 20 mM Histidine, pH 6.0 | 86.5% | 83.0% | 84.0% |

P-188 = Poloxamer P-188;
Met = L-methionine.

Inspection of the data in Table 3 for compositions identified as Formulation 2 and Comparator 2 demonstrates the stabilizing effect on the botulinum toxin by the combination of a tonicity agent, a surfactant, and an antioxidant. Formulation 2 and Comparator 2 were identical in all respects other than Comparator 2 lacked the antioxidant and had a slightly lower pH. The potency data for these two compositions shows that the antioxidant acts to stabilize the toxin, as Formulation 2 retained more than 95% potency after storage for 3 months and after storage for 7.5 months at 25° C. whereas the comparative formulation lacking the antioxidant had only 78% potency after storage for 3 months and after storage for 7.5 months at 25° C. Formulation 4 was comprised of the same components as Formulation 2, but with a higher weight percent of trehalose and a lower weight percent of poloxamer surfactant. Formulation 4 also stabilized the botulinum toxin better than the Comparator 2 formulation that lacked methionine. Accordingly, in one embodiment, a lyophilized composition is contemplated, where the composition is comprised of a Clostridial toxin active ingredient, such as a botulinum toxin; trehalose; a poloxamer surfactant; and methionine. In one embodiment, the composition retains at least about 80%, 85% or 90% potency after storage for three months at 25° C., where potency is measured in a cell-based potency assay. In another embodiment, a lyophilized composition is contemplated, where the composition is comprised of a Clostridial toxin active ingredient, such as a botulinum toxin; trehalose; a poloxamer surfactant; and methionine. In one embodiment, the composition retains potency after storage for three months at 25° C. that is at least about 10%, 15%, or 20% greater than a formulation lacking the antioxidant.

Example 2 describes another study where liquid compositions comprised of a Clostridial toxin active ingredient, a tonicity agent, a surfactant, and an antioxidant were prepared. Liquid solutions of a Clostridial toxin active ingredient, using botulinum toxin as a model, were prepared with a disaccharide tonicity agent, a poloxamer surfactant, and an antioxidant were prepared. In this particular study, the disaccharide tonicity agent was trehalose and the poloxamer surfactant was poloxamer P188. Three formulations were prepared, each with the same amount of botulinum toxin, 8 w/w % trehalose, and 4 w/w % poloxamer P188 in histidine buffer. The target potency was 100 Units/ml. Formulation 10 had no antioxidant; Formulation 11 contained NAC, and Formulation 12 contained L-methionine. The liquid compositions were placed in glass vials and stored at −70° C., 5° C., 25° C. and 40° C. for one month. Potency of the botulinum toxin was measured prior to storage and after one month of storage using a cell-based potency assay. Results are shown in Table 4.

TABLE 4

| | Liquid formulations | | | | | |
|---|---|---|---|---|---|---|
| | | | Potency, U/mL | | | |
| Formulation No.* | Antioxidant | T0 | 1 mo. −70° C. | 1 mo. 5° C. | 1 mo. 25° C. | 1 mo. 40° C. |
| Formulation 10 | None | 128 | 135 | 135 | 106 | 0.225 |
| Formulation 11 | N-acetyl-L-cysteine, 0.2% w/w | 128 | 133 | 129 | 61 | 0.2 |
| Formulation 12 | L-methionine, 0.2% w/w | 133 | 146 | 146 | 145 | 138 |

*Each formulation contained the same amount of botulinum toxin, 8 w/w % trehalose, and 4 w/w % poloxamer P188 in histidine buffer.

The liquid composition comprising methionine (Formulation 12) retained its potency after one month storage at all four temperatures, including 40° C., whereas the liquid composition with no antioxidant (Formulation 10) lost approximately 17% potency after storage for 1 month at 25° C. and lost essentially all activity (i.e., complete inactivation of the toxin) after storage for 1 month at 40° C. The liquid composition comprising NAC lost over 50% potency after storage for 1 month at 25° C. and lost essentially all activity (i.e., complete inactivation of the toxin) after storage for 1 month at 40° C., suggesting that N-acetyl-L-cysteine can act as a pro-oxidant in this formulation. In contrast, as shown in Tables 1.1 and 1.2, the lyophilized compositions comprising NAC lost 7% ((98.6-91.9)/98.6) potency after storage for 3 months at 25° C. and lost 12% ((98.6-86.5)/98.6) potency after storage for 1 month at 40° C. This demonstrates that NAC by itself can function as a stabilizer in the lyophilized compositions.

Further studies were conducted to investigate the impact of antioxidant compounds on the liquid compositions. In Example 3, liquid compositions were prepared with 100 U/mL botulinum toxin, 8 w/w % trehalose, and 4 w/w % poloxamer P188 in histidine buffer at pH 6.0. Each formulation had a different antioxidant or a combination of antioxidants, as set forth in Table 5 below and in Example 3. The antioxidants tested included NAC, L-methionine, L-tryptophan, L-glutathione, sodium sulfite, propyl gallate, and EDTA sodium salt. Potency of the formulations was tested by a cell based potency assay after filling (time zero, t0) and after storage at 40° C. for 2 weeks and 1 month. Potency test results are shown in Table 5.

terminator antioxidant (e.g., methionine, cysteine, NAC or BHT) provides a stabilizing effect on the botulinum toxin. Accordingly, compositions in liquid or solution form comprising a Clostridial toxin active ingredient; a disaccharide; a surfactant; and an antioxidant selected from methionine, NAC, EDTA, EGTA, DTPA, analogs thereof, and combinations thereof, are contemplated. In one embodiment, the composition retains potency of the toxin for a period of at least about 2 weeks when stored at about 40° C., where the potency is measured in a cell-based potency assay. In another embodiment, the composition retains potency of the toxin for a period of at least about 1 month when stored at about 40° C., where the potency is measured in a cell-based potency assay. In a further embodiment, the composition is in liquid or solution form comprising a Clostridial toxin active ingredient; a disaccharide; a surfactant; and an anti-

TABLE 5

Liquid formulations

| Formulation No.[1] | Antioxidant[2] | | | | | | | Potency U/mL | | |
|---|---|---|---|---|---|---|---|---|---|---|
| | NAC % | Met % | TRP % | GSH % | NaSul % | PrpGal % | EDTA % | T0 | 2 wks 40° C. | 1 mo. 40° C. |
| Formulation 20 | | 0.2 | | | | | | 126 | 129 | 130 |
| Formulation 21 | | | 0.2 | | | | | 127 | 13.71 | NT[3] |
| Formulation 22 | | | | 0.2 | | | | 123 | 3.76 | NT |
| Formulation 23 | | | | | 0.2 | | | 23.7 | 0.161 | NT |
| Formulation 24 | | | | | | 0.2 | | 0.164 | 0.150 | NT |
| Formulation 25 | 0.2 | 0.2 | | | | | | 133 | 0.253 | NT |
| Formulation 26 | 0.2 | | | | | | 0.03 | 129 | 127 | 127 |
| Formulation 27 | 0.2 | | 0.2 | | | | 0.03 | 129 | 125 | 122 |
| Formulation 28 | | 0.2 | 0.2 | | | | | 126 | 2.45 | NT |

[1]Each formulation contained 100 U/mL botulinum toxin, 8 w/w % trehalose, and 4 w/w % poloxamer P188 in 20 mM histidine buffer, pH 6.0 and the specified antioxidant.
[2]NAC = N-acetyl-L-cysteine;
Met = L-methionine;
TRP = L-tryptophan;
GSH = L-glutathione;
NaSul = sodium sulfite;
PrpGal = propyl gallate;
EDTA = ethylene diamine tetraacetic acid, sodium salt.
[3]NT = not tested The stabilizing effect of the antioxidant, or lack of stabilizing effect for certain antioxidants, is apparent from this study. Compositions comprising methionine (Formulation 20) retained full potency after storage at 40° C. for 2 weeks and 1 month, in contrast to compositions comprising tryptophan (Formulation 21) or glutathione (Formulation 22), indicating that not all amino acids function to stabilize a Clostridial toxin active ingredient in a liquid composition. Compositions comprising sodium sulfite (Formulation 23) or propyl gallate (Formulation 24) lost essentially all potency after 2 weeks storage at 40° C. Liquid compositions comprising NAC and EDTA sodium salt (Formulation 26) retained full potency after storage at 40° C. for 2 weeks and 1 month, as did a composition comprising NAC, EDTA sodium salt and tryptophan (Formulation 27). In contrast, as shown in Table 4, liquid compositions comprising NAC but not EDTA (Formulation 25) lost essentially all potency after 2 weeks storage at 40° C. This demonstrates that the combination of antioxidants—a chelating agent (e.g., EDTA, EGTA, DTPA or analogs thereof) and/or a chain oxidant selected from (i) methionine, and (ii) NAC and a chelating agent selected from EDTA, EGTA, DTPA, and analogs thereof. In one embodiment, the composition retains potency of the toxin for a period of at least about 1 month when stored at about 40° C., where the potency is measured in a cell-based potency assay.

In another embodiment, a liquid composition comprises a Clostridial toxin active ingredient; a tonicity agent; a surfactant; and an antioxidant selected from the group consisting of a sacrificial antioxidant, a chelating agent antioxidant, a chain terminator antioxidant, and combinations thereof.

Example 4 details another study designed to investigate the effect of a tonicity agent on stability of the toxin in the composition. In this study liquid compositions were prepared with 100 U/mL botulinum toxin, 4 w/w % poloxamer P188, 0.2 w/w % methionine, and either 8 w/w % trehalose or sucrose, in histidine buffer at pH 6.0. The two compositions were stored at 25° C. and potency was tested by a cell based potency assay prior to storage (time zero, t0) and after storage. Potency test results are shown in Table 6.

TABLE 6

Liquid formulations

| Formulation No.* | Disaccharide | Potency, U/mL at T0 and after indicated time (in months) at 25° C. | | | | | |
|---|---|---|---|---|---|---|---|
| | | T0 | 1 mo | 5.5 mo | 6 mo | 8 mo | 10.5 mo |
| Formulation 30 | trehalose (8 w/w %) | 133 | 145 | — | 147 | 159 | 43 |
| Formulation 31 | sucrose (8 w/w %) | 117 | — | 10 | — | — | — |

*Each formulation contained 100 U/mL botulinum toxin, 4 w/w % poloxamer P188 and 0.2 w/w % methionine in histidine buffer.

Comparing the potency of the toxin in Formulation 30 after 6 months of storage at 25° C. with that in Formulation 31 after 5.5 months of storage at 25° C. it is apparent that trehalose affords a stabilizing effect in a composition with poloxamer and methionine, as Formulation 30 with trehalose retained 110% of its potency (147 U/mL/133 U/mL) after 6 months storage at 25° C., whereas Formulation 31 with sucrose had only 8.5% of the target toxin potency (10 U/mL/117 U/mL) after 5.5 months storage at 25° C. Accordingly, in one embodiment, a liquid composition comprised of a Clostridial toxin active ingredient, such as a botulinum toxin; trehalose; a poloxamer surfactant; and methionine is contemplated. In one embodiment, the composition retains at least about 80%, 85%, 90% or 95% potency after storage for 1, 2, 3, 4, 5, or 6 months at 25° C., where potency is measured in a cell-based potency assay. In an alternative embodiment, the composition retains at least about 80%, 85%, 90% or 95% potency after storage for 1, 2, 3, 4, 5, or 6 months at 25° C., where potency is measured using an in vivo $LD_{50}$ potency assay.

Further studies were conducted on liquid compositions as described in Example 5. In this study, compositions comprising a Clostridial toxin active ingredient, poloxamer P188 (4 w/w %) or polysorbate (TWEEN® 20, 0.04 w/w %), trehalose (8% w/w), and methionine (0.2 w/w %), in 20 mM histidine buffer at pH 6.0, were prepared. The composition with poloxamer P188 was identified as Formulation No. 30 and the composition with polysorbate was identified as Formulation No. 32. Potency was tested by a cell based potency assay prior to storage (time zero, t0) and after 1 month of storage 40° C. for 1 month. Potency test results are shown in Table 7.

TABLE 7

Liquid formulations

| Formulation No.* | Surfactant | Potency, U/mL at time zero and after 1 month storage at 40 ° C. | |
|---|---|---|---|
| | | T0 | 1 mo. |
| Formulation 30 | poloxamer P188 (4 w/w %) | 133 | 138 |
| Formulation 32 | polysorbate (TWEEN® 20, 0.04 w/w %) | 114 | 9 |

*Each formulation contained 100 U/mL botulinum toxin, 8 w/w % trehalose, and 0.2 w/w % methionine in histidine buffer.

Comparing the potency of the toxin in Formulation 30 after 1 month of storage at 40° C. with that in Formulation 32 it is apparent that a poloxamer surfactant affords a stabilizing effect in a composition with trehalose and methionine, as Formulation 30 with poloxamer P188 retained about 104% of its initial potency (138 U/mL/133 U/mL) after one month of storage at 40° C., whereas Formulation 32 with polysorbate had only about 8% of the initial toxin potency (9 U/mL/114 U/mL) after one month of storage at 40° C. Accordingly, in one embodiment, a liquid composition comprised of a Clostridial toxin active ingredient, such as a botulinum toxin; trehalose; a poloxamer surfactant; and methionine is provided. In one embodiment, the composition retains at least about 80%, 85%, or 90% potency after storage for 1 month at 40° C., where potency is measured in a cell-based potency assay.

In another study, five liquid compositions were prepared with botulinum toxin as a model Clostridial toxin active ingredient. The compositions were prepared with or without poloxamer surfactant, with or without trehalose, and with or without methionine. Details of the compositions are given in Example 6. Potency of Formulations 33-37 was tested by a cell based potency assay prior to storage (time zero, t0) and after 1 month of storage at −70° C. and 40° C. for 1 month. Potency test results are shown in Table 8.

TABLE 8

Liquid formulations

| Formulation No. | Composition Components* | | | | Potency U/mL | | |
|---|---|---|---|---|---|---|---|
| | Toxin U/mL | Trehalose % | Poloxamer P188 % | Methionine % | T0 | 1 mo. −70° C. | 1 mo. 40° C. |
| Formulation 33 | 100 | 8 | 4 | 0 | 128 | 135 | 0.225 |
| Formulation 34 | 150 | 0 | 0 | 0.2 | 52 | 13 | 0 |
| Formulation 35 | 150 | 8 | 0 | 0.2 | 131 | 145 | 30 |
| Formulation 36 | 100 | 0 | 4 | 0.2 | 128 | 142 | 103 |
| Formulation 37 | 100 | 8 | 4 | 0.2 | 126 | — | 130 |

*Each formulation was in 20 mM histidine buffer at pH 6.0.

The potency of the botulinum toxin in Formulation 36 and in Formulation 37 after 1 month of storage at −70° C. or at 40° C. reveals that liquid compositions with poloxamer and methionine, with or without a disaccharide such as trehalose, act to stabilize the toxin. This demonstrates that poloxamer and methionine can stabilize the botulinum toxin in liquid compositions without a disaccharide. The results from Formulation 33 suggest that methionine is a stabilizer, as Formulation 33 had little toxin potency after storage in contrast to Formulation 37 and Formulation 36. The results from Formulations 34 and 35 suggest that a surfactant also has a stabilizing effect on the toxin. Accordingly, in one embodiment, a liquid composition comprised of a Clostridial toxin active ingredient, such as a botulinum toxin; a poloxamer surfactant; and an antioxidant such as methionine is contemplated. In one embodiment, the composition retains at least about 70%, 75%, or 85%, potency after storage for 1 month at 40° C., where potency is measured in a cell-based potency assay. In another embodiment, a disaccharide is also included. In one embodiment, the composition retains at least about 80%, 85% or 90% potency after storage for 1 month at 40° C., where potency is measured in a cell-based potency assay. In an alternative embodiment, the composition retains at least about 80%, 85% or 90% potency after storage for 1 month at 40° C., where potency is measured using an in vivo $LD_{50}$ potency assay.

In another study, described in Example 7, liquid compositions were prepared with botulinum toxin as a model Clostridial toxin active ingredient. The compositions were prepared with a poloxamer surfactant or with a polysorbate surfactant, with or without a disaccharide. All formulations comprised methionine. Details of the compositions are given in Example 7. Potency of the compositions, identified as Formulations 31, 38, 39 and 40, was tested by a cell based potency assay prior to storage (time zero, t0) and after storage at 5° C. for 5.5 months, 7.5 months and 12 months. Potency test results are shown in Table 9.

The potency of the botulinum toxin in Formulation 31 and in Formulation 38 after 12 months of storage at 5° C. reveals that the histidine buffer is not acting to stabilize the composition, as Formulation 38 was prepared with water and was stabilized to the same extent by the surfactant, disaccharide and methionine as Formulation 31 which was prepared with histidine buffer. Formulation 40 prepared with trehalose, polysorbate and methionine successfully stabilized the botulinum toxin as evident from the 91 U/mL potency 12 months of storage at 5° C. Accordingly, in one embodiment, a liquid composition comprised of a Clostridial toxin active ingredient, such as a botulinum toxin; a poloxamer or polysorbate surfactant; trehalose or sucrose; and an antioxidant such as methionine is contemplated. In one embodiment, the composition retains at least about 75%, 80%, or 85%, potency after storage for 1, 3, 6, 9, or 12 months at 5° C., where potency is measured in a cell-based potency assay. In an alternative embodiment, the composition retains at least about 75%, 80%, or 85%, potency after storage for 1, 3, 6, 9, or 12 months at 5° C., where potency is measured using an in vivo $LD_{50}$ potency assay.

In another study, described in Example 8, liquid compositions with no tonicity agent were prepared. Botulinum toxin was used as a model Clostridial toxin active ingredient. The compositions were prepared with either a poloxamer surfactant or with a polysorbate surfactant, and with methionine as the antioxidant. Details of the compositions are given in Example 8. Potency of the compositions, identified as Formulations 41 and 42, was tested by a cell based potency assay prior to storage (time zero, t0) and after storage for two weeks at −70° C. and at 40° C. Potency test results are shown in Table 10.

TABLE 10

Liquid formulations

| Formulation No. | Toxin U/mL | P188 % | Polysorbate (TWEEN ®20) % | methionine % | Potency U/mL after storage for 2 weeks −70° C. | 40° C. |
|---|---|---|---|---|---|---|
| Formulation 41 | 100 | 0 | 0.04 | 0.2 | 25 | 1 |

Composition Components*

TABLE 9

Liquid formulations

| Formulation No. | Treh % | Suc % | NaCl % | P188 % | TWEEN ® 20% | Met % | Buffer[2] or water | T0 | 5.5 mo | 7.5 mo | 12 mo |
|---|---|---|---|---|---|---|---|---|---|---|---|
| Formulation 31 | | 8 | | 4 | | 0.2 | buffer | 117 | 88 | NT | 94 |
| Formulation 38 | | 8 | | 4 | | 0.2 | water | 114 | NT[3] | 108 | 91 |
| Formulation 39 | | | 0.9 | 4 | | 0.2 | buffer | 94 | NT | 80 | 62 |
| Formulation 40 | 8 | | | | 0.04 | 0.2 | buffer | 114 | NT | 117 | 91 |

Composition Components[1]

Potency U/mL after storage for indicated time (in months) at 5° C.

[1]All formulations contained 100 U/mL botulinum toxin;
Treh = trehalose;
Suc = sucrose;
P-188 = poloxamer P188;
TWEEN ® 20 = polysorbate;
Met = L-methionine;
[2]Buffer = 20 mM His, pH 6.0;
[3]NT-not tested TABLE 10-continued Liquid formulations

| Formulation No. | Toxin U/mL | P188 % | Polysorbate (TWEEN®20) % | methionine % | Potency U/mL after storage for 2 weeks −70° C. | 40° C. |
|---|---|---|---|---|---|---|
| Formulation 42 | 100 | 4 | 0 | 0.2 | 105 | 72 |

*Both formulations were in 20 mM histidine buffer at pH 6.0. P-188 = poloxamer P188; Met = L-methionine The potency of the botulinum toxin in Formulation 41 and in Formulation 42 after 2 weeks of storage at −70° C. and at 40° C. reveals higher potency recoveries were achieved in liquid compositions comprising poloxamer as the surfactant, as compared to liquid compositions comprising polysorbate as the surfactant.

In another study, liquid compositions were prepared comprising a Clostridial toxin active ingredient; poloxamer P188 (4% w/w or 0.6% w/w); trehalose (2% w/w or 8% w/w); and an antioxidant—(i) EDTA and NAC (0.03% w/w and 0.2% w/w, respectively), or (ii) methionine (0.2% w/w); in 20 mM histidine buffer at pH 6.0. Each formulation had between 30-200 U botulinum toxin per vial. A summary of the compositions is set forth in Table 11.

TABLE 11

Liquid formulations

| Toxin U/mL | Tonicity Agent | | Surfactant | Antioxidant | | | Buffer |
|---|---|---|---|---|---|---|---|
| | Trehalose or Sucrose wt % | NaCl wt % | Poloxamer P188 wt % | Methionine wt % | EDTA wt % | NAC wt % | |
| 30-200 | 8 | | 4 | 0.2 | | | 20 mM His, pH 6.0 |
| 30-200 | 8 | | 0.6 | 0.2 | | | 20 mM His, pH 6.0 |
| 30-200 | 2 | 0.6 | 4 | 0.2 | | | 20 mM His, pH 6.0 |
| 30-200 | 8 | | 4 | | 0.03 | 0.2 | 20 mM His, pH 6.0 |
| 30-200 | 8 | | 4 | 0.2 | 0.03 | | |

Accordingly, in one embodiment, a liquid pharmaceutical composition is contemplated. The composition comprises a Clostridial toxin active ingredient; a tonicity agent selected from trehalose, sucrose, sodium chloride, mannitol, sorbitol, glucose and combinations thereof; a surfactant selected from a poloxamer, a polysorbate and combinations thereof, and an antioxidant selected from methionine, NAC, EDTA, EGTA, DTPA, analogs thereof, and combinations thereof. In one embodiment, the composition excludes albumin, and in another embodiment, when the antioxidant is methionine the composition excludes a polysorbate.

In another embodiment, a liquid pharmaceutical composition is contemplated. The composition comprises a Clostridial toxin active ingredient; a surfactant selected from a poloxamer, a polysorbate and combinations thereof; and an antioxidant selected from methionine, NAC, EDTA, EGTA, DTPA, analogs thereof, and combinations thereof. In one embodiment, the composition excludes albumin. In one embodiment, the composition excludes a tonicity agent.

In another embodiment, a liquid pharmaceutical composition is contemplated. The composition comprises a Clostridial toxin active ingredient; a tonicity agent selected from trehalose, sucrose, sodium chloride, mannitol, sorbitol, glucose, and combinations thereof, a poloxamer; and methionine. In one embodiment, the composition excludes albumin.

In another embodiment, a liquid pharmaceutical composition is contemplated. The composition comprises a Clostridial toxin active ingredient; a disaccharide tonicity agent in an amount between 1-15 wt %; a poloxamer in an amount between 0.5-8 wt %; and an antioxidant in an amount between 0.05-5 wt %. In another embodiment, a composition comprises a Clostridial toxin active ingredient; trehalose in an amount between 1-15 wt %; a poloxamer in an amount between 0.5-8 wt %; and methionine in an amount between 0.05-5 wt %. In one embodiment, the composition excludes albumin. In another embodiment, a liquid pharmaceutical composition comprises a Clostridial toxin active ingredient; trehalose in an amount between 2-15 wt % or 1-10 wt %; a poloxamer in an amount between 0.5-8 wt %; and methionine in an amount between 0.05-5 wt %. In one embodiment, the composition excludes albumin.

In another embodiment, a liquid pharmaceutical composition is contemplated. The composition comprises a botulinum toxin; a tonicity agent selected from trehalose, sucrose, sodium chloride, mannitol, sorbitol, glucose, and combinations thereof, a poloxamer; and an antioxidant selected from methionine, NAC, EDTA, EGTA, DTPA, analogs thereof, and combinations thereof. In one embodiment, the composition excludes albumin.

In any of the foregoing embodiments, it is contemplated that the composition is not, in some embodiments, an emulsion and/or excludes nanoparticles comprising an amphiphilic entity.

Lyophilized compositions were prepared for a study described in Example 9. The compositions that were prepared comprised botulinum toxin as a model Clostridial toxin; a disaccharide; a surfactant; and methionine as an antioxidant. The formulations were lyophilized and stored for two weeks at −20° C. or at 40° C. Potency of the lyophilized formulations after storage and reconstitution with saline was tested by a cell based potency assay. The potencies of the solid compositions are shown in Table 12.

TABLE 12

Lyophilized formulations

| Formulation No. | Composition Components* | | | | | Potency U/mL | |
|---|---|---|---|---|---|---|---|
| | Trehalose % | Sucrose % | TWEEN® 20% | Poloxamer P188 % | Methionine % | 2 weeks −20° C. | 2 weeks 40° C. |
| Formulation 43 | 8 | 0 | 0 | 4 | 0.2 | 166 | 162 |
| Formulation 44 | 8 | 0 | 0.04 | 0 | 0.2 | 147 | 137 |

TABLE 12-continued

Lyophilized formulations

| | Composition Components* | | | | | Potency U/mL | |
|---|---|---|---|---|---|---|---|
| Formulation No. | Trehalose % | Sucrose % | TWEEN® 20% | Poloxamer P188 % | Methionine % | 2 weeks −20° C. | 2 weeks 40° C. |
| Formulation 45 | 0 | 8 | 0 | 4 | 0.2 | 149 | 134 |
| Formulation 46 | 0 | 8 | 0.04 | 0 | 0.2 | 150 | 142 |

*Each formulation comprised 200 U/vial BoNT/A and was in 20 mM histidine buffer at pH 6.0.

A comparison of the potency data for lyophilized Formulation 43 and Formulation 45 permits analysis of the impact of trehalose versus sucrose as the lyoprotector on stability of botulinum toxin in lyophilized compositions, with a poloxamer as the surfactant, and methionine as an antioxidant. Formulations 43 and 45 differ only in that the former has trehalose and the latter has sucrose; both formulations comprised a poloxamer and methionine. The potency of the botulinum toxin in Formulation 43 and in Formulation 45 after 2 weeks of storage at −20° C. and at 40° C. reveals a higher potency recovery was achieved in lyophilized compositions comprising trehalose, as compared to lyophilized compositions comprising sucrose. Accordingly, in one embodiment, a lyophilized composition is provided, where the composition comprises a Clostridial toxin active ingredient, a poloxamer, methionine, and trehalose. In one embodiment, the toxin has a potency recovery of at least about 75% or at least about 80% after storage at two weeks at −20° C. and/or at 40° C.

A comparison of the potency data for Formulation 43 and Formulation 44 permits analysis of polysorbate and poloxamer as surfactants on stability of botulinum toxin in lyophilized compositions, with trehalose as a lyoprotector, and methionine as an antioxidant. Formulations 43 and 44 differ only in that the former has a poloxamer surfactant and the latter has polysorbate as the surfactant. The potency of the botulinum toxin in Formulation 43 and in Formulation 44 after 2 weeks of storage at −20° C. and at 40° C. reveals a higher potency recovery was achieved in lyophilized compositions comprising a poloxamer surfactant, as compared to lyophilized compositions comprising a polysorbate surfactant, when trehalose and methionine are present. Accordingly, in one embodiment, a lyophilized composition is provided, where the composition comprises a Clostridial toxin active ingredient, a poloxamer, methionine, and trehalose. In one embodiment, the toxin has a potency recovery of at least about 75% or at least about 80% after storage at two weeks at −20° C. and/or at 40° C.

Accordingly, in one embodiment, a solid or lyophilized pharmaceutical composition is contemplated. The composition comprises a Clostridial toxin active ingredient; a tonicity agent and/or lyoprotector selected from trehalose, sucrose, mannitol, sorbitol, glucose, and combinations thereof; a surfactant selected from a poloxamer, a polysorbate and combinations thereof; and an antioxidant selected from methionine, NAC, EDTA, EGTA, DTPA, analogs thereof, and combinations thereof. In some embodiments, the solid composition comprises a lyoprotector. In some embodiments, the lyoprotector includes sucrose, trehalose, mannitol, sorbitol, glucose, or combinations thereof. In certain embodiments, the lyophilized composition is reconstituted with a tonicity agent selected from trehalose, sucrose, sodium chloride, mannitol, sorbitol, glucose, and combinations thereof. In at least one embodiment, the lyophilized composition is reconstituted with a reconstitution vehicle comprising NaCl prior to administration to a patient. In at least one embodiment, NaCl is present in an amount of 0.9% (w/w) in the reconstitution vehicle. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, a solid or lyophilized pharmaceutical composition is contemplated. The composition comprises a Clostridial toxin active ingredient; trehalose or sucrose; a poloxamer; and methionine. In one embodiment, the composition excludes albumin, a hydroxyalkyl starch, glutamic acid, glutamine, aspartic acid, asparagine, a polyalcohol, glycine, and/or polyvinylpyrrolidone. In one embodiment, the lyophilized pharmaceutical composition comprises botulinum toxin as the Clostridial toxin active ingredient, trehalose, a poloxamer, and methionine.

In another embodiment, a solid or lyophilized pharmaceutical composition is contemplated. The composition comprises a Clostridial toxin active ingredient; trehalose in an amount between 1-15 wt %; a poloxamer in an amount between 0.5-8 wt %; and methionine in an amount between 0.05-5 wt %. In another embodiment, the composition comprises a Clostridial toxin active ingredient, such as botulinum toxin; 8 wt % trehalose; 4 wt % poloxamer; and 0.2 wt % methionine. In one embodiment, the botulinum toxin is present in an amount of about 200 units. In another embodiment, the botulinum toxin is present in an amount of about 50 units. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, a solid or lyophilized pharmaceutical composition is contemplated. The composition comprises a botulinum toxin; a disaccharide; a poloxamer; and an antioxidant selected from methionine, NAC, EDTA, EGTA, DTPA, analogs thereof, and combinations thereof. In one embodiment, the composition excludes albumin, a hydroxyalkyl starch, glutamic acid, glutamine, aspartic acid, asparagine, a polyalcohol, glycine, and/or polyvinylpyrrolidone.

In another embodiment, a lyophilized composition comprises a Clostridial toxin active ingredient; a tonicity agent and/or a lyoprotector; a surfactant; and an antioxidant selected from the group consisting of a sacrificial antioxidant, a chelating agent antioxidant, a chain terminator antioxidant, and combinations thereof. In some embodiments, the lyophilized Clostridial pharmaceutical composition comprises a lyoprotector. In some embodiments, the lyoprotector includes sucrose, trehalose, mannitol, sorbitol, glucose, or combinations thereof.

In any of the foregoing embodiments of solid or liquid compositions, it is contemplated that one or more, in any combination, of these ingredients are excluded: polyvinylpyrrolidone, diblock copolymers of polypropylene glycol and polyethylene glycol, and/or a polyalcohol such as inositol, lactitol, isomalt, xylitol, or erythritol.

Pharmaceutical Composition Components

The present pharmaceutical compositions include a Clostridial toxin or a Clostridial toxin active ingredient. A skilled artisan will appreciate that the description herein refers to a Clostridial toxin active ingredient, however, a Clostridial toxin may also be used in the compositions described herein. Accordingly, the term Clostridial toxin active ingredient will be used; however it should be understood that a Clostridial toxin is equally contemplated. In one embodiment, a therapeutically effective concentration of a Clostridial toxin active ingredient is present in the composition. In one embodiment, the Clostridial toxin active ingredient reduces a symptom associated with the aliment being treated by, e.g., at least 10%, at least 20%, at least 30%, at least 40%, at least 50%, at least 60%, at least 70%, at least 80%, at least 90% or at least 100%. In other aspects of this embodiment, a therapeutically effective concentration of a Clostridial toxin active ingredient reduces a symptom associated with the aliment being treated by, e.g., at most 10%, at most 20%, at most 30%, at most 40%, at most 50%, at most 60%, at most 70%, at most 80%, at most 90% or at most 100%.

It is envisioned that any amount of Clostridial toxin active ingredient can be added in formulating a Clostridial toxin active ingredient pharmaceutical compositions disclosed herein, with the proviso that a therapeutically effective amount of Clostridial toxin active ingredient is recoverable. In aspects of this embodiment, the amount of Clostridial toxin active ingredient added to the formulation is at least 0.1 U/ml, at least 1.0 U/ml, at least 10 U/ml, at least 50 U/ml, at least 100 U/ml, at least 200 U/ml, or at least 1000 U/ml. In other aspects of this embodiment, the amount of Clostridial toxin active ingredient added to the formulation is at most 0.1 U/ml, at most 1.0 U/ml, at most 10 U/ml, at most 50 U/ml, at most 100 U/ml, at most 200 U/ml, or at most 1000 U/ml. In yet other aspects of this embodiment, the amount of Clostridial toxin active ingredient added to the formulation is from about 0.1 U/ml to about 1000 U/ml, or about 1.0 U/ml to about 1000 U/ml. In still other aspects of this embodiment, the amount of Clostridial toxin active ingredient added to the formulation is from about 0.001 U/ml to about 100 U/ml, about 0.01 U/ml to about 100 U/ml, about 0.1 U/ml to about 100 U/ml, or about 1.0 U/ml to about 100 U/ml.

In other aspects of this embodiment, the amount of Clostridial toxin active ingredient added to the formulation is at least 1.0 µg, at least 10 µg, at least 100 µg, at least 1.0 ng, at least 10 ng, at least 100 ng, at least 1.0 µg, at least 10 µg, at least 100 µg, or at least 1.0 mg. In still other aspects of this embodiment, the amount of Clostridial toxin active ingredient added to the formulation is at most 1.0 µg, at most 10 µg, at most 100 µg, at most 1.0 ng, at most 10 ng, at most 100 ng, at most 1.0 µg, at most 10 µg, at most 100 µg, or at most 1.0 mg. In still other aspects of this embodiment, the amount of Clostridial toxin active ingredient added to the formulation is about 1.0 µg to about 10 µg, about 10 µg to about 10 µg, about 100 µg to about 10 g, about 1.0 ng to about 10 µg, about 10 ng to about 10 µg, or about 100 ng to about 10 µg. In still other aspects of this embodiment, the amount of Clostridial toxin active ingredient added to the formulation is about 1.0 pg to about 1.0 µg, about 10 pg to about 1.0 µg, about 100 pg to about 1.0 µg, about 1.0 ng to about 1.0 µg, about 10 ng to about 1.0 µg, or about 100 ng to about 1.0 µg. In further aspects of this embodiment, the amount of Clostridial toxin active ingredient added to the formulation is about 1.0 pg to about 5.0 µg, about 10 pg to about 5.0 µg, about 100 pg to about 5.0 µg, about 1.0 ng to about 5.0 µg, about 10 ng to about 5.0 µg, or about 100 ng to about 5.0 µg. In further aspects of this embodiment, the amount of Clostridial toxin active ingredient added to the formulation is about 1.0 pg to about 10 µg, about 10 pg to about 10 ag, about 100 pg to about 10 g, about 1.0 ng to about 10 ag, about 10 ng to about 10 ag, or about 100 ng to about 10 ag.

In aspects of this embodiment, a Clostridial toxin pharmaceutical composition comprises a BoNT/A, a BoNT/B, a BoNT/C$_1$, a BoNT/D, a BoNT/E, a BoNT/F, a BoNT/G, a mosaic BoNT such as for example BoNT/DC, a TeNT, a BaNT, or a BuNT. In another embodiment, a Clostridial toxin pharmaceutical composition comprises a Clostridial toxin variant as the Clostridial toxin. In aspects of this embodiment, a Clostridial toxin pharmaceutical composition comprises naturally-occurring Clostridial toxin active ingredient variant or a non-naturally-occurring Clostridial toxin variant. In other aspects of this embodiment, a Clostridial toxin pharmaceutical composition comprises a BoNT/A variant, a BoNT/B variant, a BoNT/C$_1$ variant, a BoNT/D variant, a BoNT/E variant, a BoNT/F variant, a BoNT/G variant, a TeNT variant, a BaNT variant, or a BuNT variant, where the variant is either a naturally-occurring variant or a non-naturally-occurring variant.

Aspects of the present pharmaceutical compositions provide, in part, a Clostridial toxin complex as a Clostridial toxin active ingredient. As used herein, the term "Clostridial toxin complex" refers to a complex comprising a Clostridial toxin and associated NAPs, such as, e.g., a Botulinum toxin complex, a Tetanus toxin complex, a Baratii toxin complex, and a Butyricum toxin complex. Non-limiting examples of Clostridial toxin complexes include those produced by a *Clostridium botulinum*, such as, e.g., a 900-kDa BoNT/A complex, a 500-kDa BoNT/A complex, a 300-kDa BoNT/A complex, a 500-kDa BoNT/B complex, a 500-kDa BoNT/C$_1$ complex, a 500-kDa BoNT/D complex, a 300-kDa BoNT/D complex, a 300-kDa BoNT/E complex, and a 300-kDa BoNT/F complex. Clostridial toxin complexes can be purified using the methods described in Schantz, supra, (1992); Hui Xiang et al., *Animal Product Free System* and *Process for Purifying a Botulinum* Toxin, U.S. Pat. No. 7,354,740, each of which is hereby incorporated by reference in its entirety. Clostridial toxin complexes can be obtained from, e.g., List Biological Laboratories, Inc. (Campbell, California), the Centre for Applied Microbiology and Research (Porton Down, U.K), Wako (Osaka, Japan), and Sigma Chemicals (St Louis, Missouri).

Aspects of the present pharmaceutical compositions provide, in part, a non-protein excipient. As used herein, the term "non-protein excipient" refers to any excipient that is not a polypeptide comprising at least fifteen amino acids. It is envisioned that any non-protein excipient is useful in formulating a Clostridial toxin active ingredient pharmaceutical compositions disclosed in the present specification, with the proviso that a therapeutically effective amount of the Clostridial toxin active ingredient is recovered using this non-protein excipient.

Aspects of the present pharmaceutical compositions provide, in part, a sugar. As used herein, the term "sugar" refers to a compound comprising one to 10 monosaccharide units, e.g., a monosaccharide, a disaccharide, a trisaccharide, and an oligosaccharide comprising four to ten monosaccharide units. It is envisioned that any sugar is useful in formulating a Clostridial toxin active ingredient pharmaceutical compositions disclosed in the present specification, with the proviso that a therapeutically effective amount of the Clostridial toxin active ingredient is recovered using this sugar. In some embodiments, for example in a lyophilized composition, the sugar can function as a lyoprotector. In some other embodiments, for example in a lyophilized formulation or in a liquid formulation, the sugar can function as a tonicity agent. Monosaccharides are polyhydroxy aldehydes or polyhydroxy ketones with three or more carbon atoms, including aldoses, dialdoses, aldoketoses, ketoses and diketoses, as well as cyclic forms, deoxy sugars and amino sugars, and their derivatives, provided that the parent monosaccharide has a (potential) carbonyl group. Monosacchrides include trioses, like glyceraldehyde and dihydroxyacetone; tetroses, like erythrose, erythrulose and threose; pentoses, like arabinose, lyxose, ribose, ribulose, xylose, xylulose; hexoses, like allose, altrose, fructose, fucose, galactose, glucose, gulose, idose, mannose, psicose, rhamnose, sorbose, tagatose, talose and trehalose; heptoses, like sedoheptulose and mannoheptulose; octooses, like octulose and 2-keto-3-deoxy-manno-octonate; nonoses like sialose; and decose. Oligosaccharides are compounds in which at least two monosaccharide units are joined by glycosidic linkages. According to the number of units, they are called disaccharides, trisaccharides, tetrasaccharides, pentasaccharides, hexasaccharides, heptosaccharides, octosaccharides, monosaccharides, decosaccharides, etc. An oligosaccharide can be unbranched, branched or cyclic. Common disaccharides include, without limitation, sucrose, lactose, maltose, trehalose, cellobiose, gentiobiose, kojibiose, laminaribiose, mannobiose, melibiose, nigerose, rutinose, and xylobiose. Common trisaccharides include, without limitation, raffinose, acarbose, maltotriose, and melezitose. Other non-limiting examples of specific uses of sugar excipients can be found in, e.g., Ansel, supra, (1999); Gennaro, supra, (2000); Hardman, supra, (2001); and Rowe, supra, (2003), each of which is hereby incorporated by reference in its entirety In an embodiment, a Clostridial toxin active ingredient pharmaceutical composition comprises a sugar. In aspects of this embodiment, a Clostridial toxin active ingredient pharmaceutical composition comprises a monosaccharide. In other aspects of this embodiment, a Clostridial toxin active ingredient pharmaceutical composition comprises a disaccharide, a trisaccharide, a tetrasaccharide, a pentasaccharide, a hexasaccharide, a heptosaccharide, an octosaccharide, a monosaccharide, or a decosaccharide. In yet other aspects of this embodiment, a Clostridial toxin active ingredient pharmaceutical composition comprises an oligosaccharide comprising two to ten monosaccharide units.

It is envisioned that any amount of sugar is useful in formulating a Clostridial toxin active ingredient pharmaceutical compositions disclosed in the present specification, with the proviso that a therapeutically effective amount of the Clostridial toxin active ingredient is recovered using this sugar amount. In aspects of this embodiment, the amount of sugar added to the formulation is about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), about 10% (w/w), about 15% (w/w), about 20% (w/w), about 25% (w/w), about 30% (w/w), or about 35% (w/w). In other aspects of this embodiment, the amount of sugar added to the formulation is at least 0.1% (w/w), at least 0.5% (w/w), at least 1.0% (w/w), at least 1.5% (w/w), at least 2.0% (w/w), at least 2.5% (w/w), at least 3.0% (w/w), at least 3.5% (w/w), at least 4.0% (w/w), at least 4.5% (w/w), at least 5.0% (w/w), at least 5.5% (w/w), at least 6.0% (w/w), at least 6.5% (w/w), at least 7.0% (w/w), at least 7.5% (w/w), at least 8.0% (w/w), at least 8.5% (w/w), at least 9.0% (w/w), at least 9.5% (w/w), at least 10% (w/w), at least 15% (w/w), at least 20% (w/w), at least 25% (w/w), at least 30% (w/w), or at least 35% (w/w). In yet other aspects of this embodiment, the amount of sugar added to the formulation is at most 0.1% (w/w), at most 0.5% (w/w), at most 1.0% (w/w), at most 1.5% (w/w), at most 2.0% (w/w), at most 2.5% (w/w), at most 3.0% (w/w), at most 3.5% (w/w), at most 4.0% (w/w), at most 4.5% (w/w), at most 5.0% (w/w), at most 5.5% (w/w), at most 6.0% (w/w), at most 6.5% (w/w), at most 7.0% (w/w), at most 7.5% (w/w), at most 8.0% (w/w), at most 8.5% (w/w), at most 9.0% (w/w), at most 9.5% (w/w), at most 10% (w/w), at most 15% (w/w), at most 20% (w/w), at most 25% (w/w), at most 30% (w/w), or at most 35% (w/w).

In an embodiment, the present Clostridial toxin active ingredient pharmaceutical composition comprises a disaccharide. Common disaccharides include, without limitation, sucrose, lactose, maltose, trehalose, cellobiose, gentiobiose, kojibiose, laminaribiose, mannobiose, melibiose, nigerose, rutinose, and xylobiose. In aspects of this embodiment, the Clostridial toxin active ingredient pharmaceutical composition comprises sucrose. In one specific embodiment, the Clostridial toxin active ingredient pharmaceutical composition comprises trehalose. In aspects of this embodiment, the amount of disaccharide added to the formulation added to the formulation is about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), about 10% (w/w), about 15% (w/w), about 20% (w/w), about 25% (w/w), about 30% (w/w), or about 35% (w/w).

Aspects of the present pharmaceutical compositions provide, in part, a surfactant. It is envisioned that any surfactant is useful in formulating a Clostridial toxin active ingredient pharmaceutical compositions disclosed in the present specification, with the proviso that a therapeutically effective amount of the Clostridial toxin active ingredient is recovered using this surfactant amount. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); solutol HS15; 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001);

and Rowe, supra, (2003), each of which is hereby incorporated by reference in its entirety.

Thus in an embodiment, a Clostridial toxin active ingredient pharmaceutical composition comprises a surfactant. In aspects of this embodiment, a Clostridial toxin active ingredient pharmaceutical composition comprises a polysorbate, a poloxamer, a polyoxyethyleneglycol dodecyl ether, 2-dodecoxyethanol, polyoxyethylene octyl phenyl ether, sodium dodecyl sulfate, 3-[(3-Cholamidopropyl)dimethylammonio]-1-propanesulfonate, 3-[(3-Cholamidopropyl) dimethylammonio]-2-hydroxy-1-propanesulfonate, sucrose monolaurate; or sodium cholate.

It is envisioned that any amount of surfactant is useful in formulating a Clostridial toxin active ingredient pharmaceutical compositions disclosed in the present specification, with the proviso that a therapeutically effective amount of the Clostridial toxin active ingredient is recovered using this surfactant amount. In aspects of this embodiment, the amount of surfactant added to the formulation is about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), about 10% (w/w), about 15% (w/w), about 20% (w/w), about 25% (w/w), about 30% (w/w), or about 35% (w/w). In other aspects of this embodiment, the amount of surfactant added to the formulation is at least 0.01% (w/w), at least 0.02% (w/w), at least 0.03% (w/w), at least 0.04% (w/w), at least 0.05% (w/w), at least 0.06% (w/w), at least 0.07% (w/w), at least 0.08% (w/w), at least 0.09% (w/w), at least 0.1% (w/w), at least 0.5% (w/w), at least 1.0% (w/w), at least 1.5% (w/w), at least 2.0% (w/w), at least 2.5% (w/w), at least 3.0% (w/w), at least 3.5% (w/w), at least 4.0% (w/w), at least 4.5% (w/w), at least 5.0% (w/w), at least 5.5% (w/w), at least 6.0% (w/w), at least 6.5% (w/w), at least 7.0% (w/w), at least 7.5% (w/w), at least 8.0% (w/w), at least 8.5% (w/w), at least 9.0% (w/w), at least 9.5% (w/w), at least 10% (w/w), at least 15% (w/w), at least 20% (w/w), at least 25% (w/w), at least 30% (w/w), or at least 35% (w/w). In yet other aspects of this embodiment, the amount of surfactant added to the formulation is at most 0.01% (w/w), at most 0.02% (w/w), at most 0.03% (w/w), at most 0.04% (w/w), at most 0.05% (w/w), at most 0.06% (w/w), at most 0.07% (w/w), at most 0.08% (w/w), at most 0.09% (w/w), at most 0.1% (w/w), at most 0.5% (w/w), at most 1.0% (w/w), at most 1.5% (w/w), at most 2.0% (w/w), at most 2.5% (w/w), at most 3.0% (w/w), at most 3.5% (w/w), at most 4.0% (w/w), at most 4.5% (w/w), at most 5.0% (w/w), at most 5.5% (w/w), at most 6.0% (w/w), at most 6.5% (w/w), at most 7.0% (w/w), at most 7.5% (w/w), at most 8.0% (w/w), at most 8.5% (w/w), at most 9.0% (w/w), at most 9.5% (w/w), at most 10% (w/w), at most 15% (w/w), at most 20% (w/w), at most 25% (w/w), at most 30% (w/w), or at most 35% (w/w).

In some embodiments, the Clostridial toxin active ingredient pharmaceutical composition comprises a poloxamer. Poloxamers which can be used with the present pharmaceutical composition include Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (e.g., PLURONIC® F68, KOLLIPHOR® P 188), Poloxamer 237 (PLURONIC® F87), Poloxamer 338 (PLURONIC® L108), Poloxamer 407 (PLURONIC® F127). In some embodiments, poloxamer 188 may be more advantageous.

In some embodiments, the Clostridial toxin active ingredient pharmaceutical composition comprises a polysorbate. Polysorbates which can be used with the present pharmaceutical composition includes polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81). In some embodiments, polysorbate 20 may be more advantageous than some other polysorbates.

Aspects of the present pharmaceutical compositions provide, in part, at least an antioxidant. Non-limiting examples of antioxidant include, without limitation, methionine, cysteine, NAC, glutathionine, lipoic acid, sodium metabisulfite, sodium thiosulfate, ascorbic acid, butylated hydroxyanisole, butylated hydroxytoluene, vitamin E and analogs including Trolox C; chelators such as EDTA (ethylene diamine tetraacetic acid sodium salt), EGTA (ethylene glycol-bis(2-aminoethylether)-N,N,N',N'-tetraacetic acid), DTPA (diethylenetriaminepentaacetic acid), analogs or derivatives thereof; and combinations thereof. In aspects of this embodiment, the amount of antioxidant added to the formulation ranges from about 0.01% (w/w) to about 0.10% (w/w).

It is further envisioned that a Clostridial toxin active ingredient pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, emulsifying agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a pharmaceutical composition as needed. It is envisioned that any buffered pH level can be useful in formulating a Clostridial toxin active ingredient pharmaceutical composition, with the proviso that a therapeutically effective amount of the Clostridial toxin active ingredient is recovered using this effective pH level. In an aspect of this embodiment, an effective pH level is at least about pH 5.0, at least about pH 5.5, at least about pH 6.0, at least about pH 6.5, at least about pH 7.0 or at about pH 7.5. In another aspect of this embodiment, an effective pH level is at most about pH 5.0, at most about pH 5.5, at most about pH 6.0, at most about pH 6.5, at most about pH 7.0 or at most about pH 7.5. In yet another aspect of this embodiment, an effective pH level is about pH 5.0 to about pH 8.0, an effective pH level is about pH 5.0 to about pH 7.0, an effective pH level is about pH 5.0 to about pH 6.0, is about pH 5.5 to about pH 8.0, an effective pH level is about pH 5.5 to about pH 7.0, an effective pH level is about pH 5.5 to about pH 5.0, is about pH 5.5 to about pH 7.5, an effective pH level is about pH 5.5 to about pH 6.5.

The pharmaceutical compositions disclosed herein can have a pH of between about 5 and 8 when reconstituted or upon injection. In certain embodiments, the composition will have a pH below 8, such as, for example, 7.9, or 7.8, or 7.7, or 7.6, or 7.5, or 7.4, or 7.3, or 7.2, or 7.1, or 7.0, or 6.9, or 6.8, or 6.7, or 6.6, or 6.5, or 6.4, or 6.3, or 6.2, or 6.1, or 6.0, or 5.9, or 5.8, or 5.7, or 5.6, or 5.5, or 5.4, or 5.3, or 5.2, or 5.1, or the like. In some embodiments, the pH ranges from 5 to 7.

It is envisioned that any concentration of a buffer can be useful in formulating a Clostridial toxin active ingredient pharmaceutical composition, with the proviso that a therapeutically effective amount of the Clostridial toxin active ingredient is recovered using this effective concentration of buffer. In aspects of this embodiment, an effective concentration of buffer is at least 0.1 mM, at least 0.2 mM, at least 0.3 mM, at least 0.4 mM, at least 0.5 mM, at least 0.6 mM, at least 0.7 mM, at least 0.8 mM, or at least 0.9 mM. In other aspects of this embodiment, an effective concentration of buffer is at least 1.0 mM, at least 2.0 mM, at least 3.0 mM, at least 4.0 mM, at least 5.0 mM, at least 6.0 mM, at least 7.0 mM, at least 8.0 mM, or at least 9.0 mM. In yet other aspects of this embodiment, an effective concentration of buffer is at least 10 mM, at least 20 mM, at least 30 mM, at least 40 mM, at least 50 mM, at least 60 mM, at least 70 mM, at least 80 mM, or at least 90 mM. In still other aspects of this embodiment, an effective concentration of buffer is at least 100 mM, at least 200 mM, at least 300 mM, at least 400 mM, at least 500 mM, at least 600 mM, at least 700 mM, at least 800 mM, or at least 900 mM. In further aspects of this embodiment, an effective concentration of buffer is at most 0.1 mM, at most 0.2 mM, at most 0.3 mM, at most 0.4 mM, at most 0.5 mM, at most 0.6 mM, at most 0.7 mM, at most 0.8 mM, or at most 0.9 mM. In still other aspects of this embodiment, an effective concentration of buffer is at most 1.0 mM, at most 2.0 mM, at most 3.0 mM, at most 4.0 mM, at most 5.0 mM, at most 6.0 mM, at most 7.0 mM, at most 8.0 mM, or at most 9.0 mM. In yet other aspects of this embodiment, an effective concentration of buffer is at most 10 mM, at most 20 mM, at most 30 mM, at most 40 mM, at most 50 mM, at most 60 mM, at most 70 mM, at most 80 mM, or at most 90 mM. In still other aspects of this embodiment, an effective concentration of buffer is at most 100 mM, at most 200 mM, at most 300 mM, at most 400 mM, at most 500 mM, at most 600 mM, at most 700 mM, at most 800 mM, or at most 900 mM. In still further aspects of this embodiment, an effective concentration of buffer is about 0.1 mM to about 900 mM, 0.1 mM to about 500 mM, 0.1 mM to about 100 mM, 0.1 mM to about 90 mM, 0.1 mM to about 50 mM, 1.0 mM to about 900 mM, 1.0 mM to about 500 mM, 1.0 mM to about 100 mM, 1.0 mM to about 90 mM, or 1.0 mM to about 50 mM.

Embodiments described herein can be practiced with a composition that comprises a plurality of botulinum toxin serotypes, such as botulinum toxin serotypes selected from the group consisting of botulinum toxin serotypes A, B, $C_1$ D, E, F and G. In certain embodiments, purified botulinum toxins, can be used. In other embodiments, modified botulinum toxins may be used.

In some embodiments, the composition may optionally also include NaCl. NaCl may particularly preferably be included in compositions comprising botulinum toxin, trehalose or sucrose, poloxamer 188, and methionine, and is particularly preferably included in liquid compositions comprising botulinum toxin, trehalose or sucrose, poloxamer 188, and methionine. In some lyophilized formulations, NaCl may function as a tonicity agent in a reconstitution vehicle. In one embodiment, NaCl may be present in an amount of 0.9% (w/w) in the reconstitution vehicle.

In some embodiments, the Clostridial toxin active ingredient pharmaceutical composition can be formulated as a lyophilized (i.e. freeze dried) or vacuum dried powder which can be reconstituted with a suitable fluid, such as saline or water, prior to administration to a patient. In alternative embodiments, the pharmaceutical composition can be formulated as an aqueous solution or suspension.

In some embodiments, the solid Clostridial toxin active ingredient pharmaceutical composition comprises a botulinum toxin, a tonicity agent and/or a lyoprotector, a poloxamer and/or a polysorbate and an antioxidant. In some embodiments, the Clostridial toxin active ingredient pharmaceutical composition comprises a botulinum toxin. In some embodiments, the Clostridial toxin active ingredient pharmaceutical composition comprises trehalose. In some embodiments, the Clostridial toxin active ingredient pharmaceutical composition comprises poloxamer 188 or polysorbate 20. In some embodiments, the composition comprises EDTA EGTA, DTPA, or analogs thereof. In alternative embodiments, the composition comprises methionine and/or NAC. In aspects of these alternative embodiments, the composition further comprises EDTA, EGTA, DTPA, or analogs thereof. In some embodiments, the composition further comprises a buffering agent. In one embodiment, the composition comprises histidine buffer. In some embodiments, the relative weight amounts of disaccharide, poloxamer and antioxidant are within the following ranges: trehalose: 1 to 15%, 1 to 10%, or 2-15% or 2-10%; poloxamer: 0.5-8% or 0.5 to 5%; methionine: 0.01 to 5%, 0.02 to 3%, 0.05 to 1%, 0.05 to 0.5%. In some embodiments, the relative weight amounts of trehalose, poloxamer and methionine are within the following ranges: trehalose: 1 to 15%, 1 to 10%, or 2-15% or 2-10%; poloxamer: 0.5-8% or 0.5 to 5%; methionine: 0.01 to 5%, 0.02 to 3%, 0.05 to 1%, 0.05 to 0.5%. In some embodiments, the relative weight amounts of trehalose, poloxamer and methionine are within the following ranges respectively: 1 to 10%; 0.5 to 5% and 0.1 to 0.3%. In other embodiments, the relative weight amounts of trehalose, polysorbate and methionine are within the following ranges respectively: 1 to 15%; 0.02% to 0.06%; and 0.1 to 0.3%. In other embodiments, the relative weight amounts of trehalose, polysorbate and methionine are within the following ranges respectively: 1 to 10%; 0.02% to 0.06%; and 0.1 to 0.3%. In some embodiments, the relative weight amount of EDTA or an EDTA analog is from about 0.01 to 0.10%. In some embodiments, the relative weight amount of NAC ranges from 0.01 to 0.5%.

In aspects of these embodiments, the Clostridial toxin active ingredient pharmaceutical composition is formulated as a solid (i.e., lyophilized or vacuum dried) composition. In some embodiments, the solid Clostridial pharmaceutical composition comprises a lyoprotector. In some embodiments, the preferred lyoprotector includes sucrose, trehalose, mannitol, sorbitol, glucose, or combinations thereof. In some embodiments, the solid pharmaceutical composition comprises NAC in a relative weight amount of 0.01 to 0.5%. In some embodiments, the pharmaceutical composition further comprises EDTA, EGTA, DTPA, or analogs thereof. In alternative embodiments, the solid pharmaceutical composition comprises methionine and EDTA, EGTA, DTPA, or analogs thereof.

In one embodiment, the composition is a solid composition consisting of botulinum toxin type A, 8% (w/w) trehalose, 4% (w/w) poloxamer 188, 0.2% (w/w) methionine, and a Histidine buffer. In one embodiment, the solid composition is reconstituted with a reconstitution vehicle comprising NaCl prior to administration to a patient. In one embodiment, NaCl may be present in an amount of 0.9% (w/w) in the reconstitution vehicle.

In an alternative aspect of these embodiments, the Clostridial toxin active ingredient pharmaceutical composition is formulated as a liquid. In some embodiments, the liquid pharmaceutical composition comprises a tonicity agent selected from trehalose, sucrose, sodium chloride, mannitol, sorbitol, glucose, and combinations thereof. In some embodiments, the liquid pharmaceutical composition comprises NAC in a relative weight amount of 0.1 to 0.5%. In some embodiments, the liquid pharmaceutical composition comprises NAC and a chelating agent selected from EDTA, EGTA, DTPA, and analogs thereof. In some embodiments, the liquid pharmaceutical composition comprises histidine buffer. In some embodiments, the liquid pharmaceutical composition has a pH from 5 to 7.

Methods of Treatment

In embodiments, methods of treating diseases, disorders, conditions, and the like, are described which comprise administering a pharmaceutical composition as described herein to a subject in need thereof in an amount sufficient to produce improved patient function. In certain embodiments, the diseases are of a neuromuscular nature, such as, for example, those diseases that affect muscles and nerve control thereof, such as, for example, overactive bladder, and the like. Certain embodiments relate to the treatment of pain, such as, for example, treatment of headache pain, or back pain, or muscle pain, or the like. In certain embodiments, methods encompass the treatment of psychological disorders, including, for example, depression, anxiety, and the like.

Compositions and methods described herein can be useful for the treatment, reduction of symptoms, and/or prevention of, for example, achalasia, anal fissure, anismus, blepharospasm, cerebral palsy, cervical dystonia, cervicogenic headache, hemifacial spasm, dyshidrotic eczema, dysphagia, dysphonia, esophageal dysmotility, esophageal muscular ring, esotropia (infantile), eyelift, facial myokymia, gait disturbances (idiopathic toe-walking), generalized dystonia, hemifacial spasm, hyperfunctional facial lines (glabellar, forehead, crows' feet, down-turned angles of the mouth), hyperhidrosis, incontinence (idiopathic or neurogenic), medication overuse headache, migraine headache, myoclonus, muscle mass or activity reduction, involving, for example, the masseter or the like, myofascial pain syndrome, obstructive urinary symptoms, pancreas divisum pancreatitis, Parkinson's disease, puborectalis syndrome, reduction of surgical scar tension, salivary hypersecretion, sialocele, sixth nerve palsy, spasticity, speech/voice disorders, strabismus, surgery adjunct (ophthalmic), tardive dyskinesia, temporomandibular joint disorders, tension headache, thoracic outlet syndrome, torsion dystonia, torticollis, Tourette's syndrome, tremor, whiplash-associated neck pain, pain, itching, inflammation, allergy, cancer and benign tumors, fever, obesity, infectious diseases, viral and bacterial, hypertension, cardiac arrhythmias, vasospasm, atherosclerosis, endothelial hyperplasia, venous thrombosis, varicose veins, aphthous stomatitis, hypersalivation, temporomandibular joint syndrome, hyperhidrosis, bromhidrosis, acne, rosacea, hyperpigmentation, hypertrophic scars, keloids, calluses and corns, skin wrinkling, excessive sebum production, psoriasis, dermatitis, allergic rhinitis, nasal congestion, post nasal drip, sneezing, ear wax, serous and suppurative otitis media, tonsil and adenoid hypertrophy, tinnitus, dizziness, vertigo, hoarseness, cough, sleep apnea, snoring, glaucoma, conjunctivitis, uveitis, strabismus, Grave's disease, excessive hair growth, hair loss, asthma, bronchitis, emphysema, mucus production, pleuritis, coagulation disorders, myeloproliferative disorders, disorders involving eosinophils, neutrophils, macrophages and lymphocytes, immune tolerance and transplantation, autoimmune disorders, dysphagia, acid reflux, hiatal hernia, gastritis and hyperacidity, diarrhea and constipation, hemorrhoids, urinary incontinence, prostatic hypertrophy, erectile dysfunction, priapism and Peyronie's disease, epididymitis, contraception, menstrual cramps, preventing premature delivery, endometriosis and fibroids, arthritis, osteoarthritis, rheumatoid, bursitis, tendonitis, tenosynovitis, fibromyalgia, seizure disorders, spasticity, headache, and neuralgias.

In certain embodiments, patients are limited to a maximum of 360 U of botulinum toxin administered over any 90-day period.

Treatment of Nerve/Muscle Conditions

In an embodiment, the neuromuscular disease is hyperhidrosis. A subject suffering from hyperhidrosis, for example, receives about 59 U per axilla, or about 58 U per axilla, or about 57 U per axilla, or about 56 U per axilla, or about 55 U per axilla, or about 54 U per axilla, or about 53 U per axilla, or about 52 U per axilla, or about 51 U per axilla, or about 50 U per axilla, or about 49 U per axilla, or about 48 U per axilla, or about 47 U per axilla, or about 46 U per axilla, or about 45 U per axilla, or about 44 U per axilla, or about 43 U per axilla, or about 42 U per axilla, or about 41 U per axilla, or about 40 U per axilla, or about 39 U per axilla, or about 38 U per axilla, or about 37 U per axilla, or about 36 U per axilla, or less, per treatment of a pharmaceutical composition described herein. In an embodiment, 50 U total are injected intradermally into 10-15 sites spaced approximately 1-2 cm apart.

In an embodiment, the neuromuscular disease is hemifacial spasm. A subject suffering from hemifacial spasm, for example receives between about 1.5 to 15 U per treatment of a pharmaceutical composition described herein. In a further example, the subject receives between about 1.5 to 3 U, 1.5 to 5 U, 1.5 to 7 U, 1.5 to 10 U, 1.5 to 12 U, 1.5 to 15 U, 5 to 10 U, 5 to 15 U, or 10 to 15 U per treatment are administered to a patient with hemifacial spasm. In a still further example, the subject receives about 1.5 U, about 2 U, about 2.5 U, about 3 U, about 3.5 U, about 4 U, about 4.5 U about 5 U, about 5.5 U, about 6 U, about 6.5 U, about 7 U, about 7.5 U, about 8 U, about 8.5 U, about 9 U, about 9.5 U, about 10 U, about 10.5 U, about 11 U, about 11.5 U, about 12 U, about 12.5 U, about 13 U, about 13.5 U, about 14 U, about 14.5 U, or about 15 U per treatment are administered to a patient with hemifacial spasm. Dosages greater than 15 U per treatment may also be administered to patients with hemifacial spasm to achieve a therapeutic response. A treatment session can comprise multiple treatments.

In an embodiment, the neuromuscular disease is cervical dystonia. A subject suffering from cervical dystonia, for example, receives between about 15 to 300 U per treatment of a pharmaceutical composition described herein. In a further example, the subject receives between about 35 to 250 U, 65 to 200 U, 85 to 175 U, 105 to 160 U, or 125 to 145 U are administered to a patient with cervical dystonia. In an embodiment, dosages to the sternocleidomastoid muscle is limited to 100 U or less. Dosages greater than 300 U per treatment may also be administered to patients with cervical dystonia to achieve a therapeutic response. A treatment session can comprise multiple treatments.

In an embodiment, the neuromuscular disease is blepharospasm. A subject suffering from blepharospasm, for example, receives between about 1.25 to 2.5 U of a pharmaceutical composition described herein injected into the medial and lateral pretarsal orbicularis oculi of the upper lid and into the lateral pretarsal orbicularis oculi of the lower lid. In a further example, the subject receives about 1.5 U, about 1.6 U, about 1.7 U, about 1.8 U, about 1.9 U, about 2.0 U, about 2.1 U, about 2.2 U, about 2.3 U, about 2.4 U, about 2.5 U, or more, per injection site. A treatment session can comprise multiple treatments.

In an embodiment, the neuromuscular disease is strabismus. A subject suffering from strabismus, for example, receives between about 1.25 to 2.5 U per injection site of a pharmaceutical composition described herein. In a further example, the subject receives about 1.5 U, about 1.6 U, about 1.7 U, about 1.8 U, about 1.9 U, about 2.0 U, about 2.1 U, about 2.2 U, about 2.3 U, about 2.4 U, about 2.5 U, or more, per injection site to achieve a therapeutic response. In embodiments, lower doses are used for treatment of small deviations. In embodiments, vertical muscles and horizontal strabismus of less than 20 prism diameters can be treated with 1.25 to 2.5 U per injection site. A treatment session can comprise multiple treatments.

In an embodiment, the neuromuscular disease is muscle spasticity. A subject suffering from muscle spasticity, for example, receives between about 20 to 200 U per treatment of a pharmaceutical composition described herein. In a further example, the subject receives between about 20 to 30 U, 20 to 40 U, 20 to 60 U, 20 to 80 U, 20 to 100 U, 20 to 125 U, 20 to 150 U, or 20 to 175 U per treatment are administered to a patient with muscle spasticity. In a still further example, the subject receives about 20 U, about 25 U, about 30 U, about 35 U, about 40 U, about 45 U, about 50 U, about 55 U, about 60 U, about 65 U, about 70 U, about 75 U, about 80 U, about 85 U, about 90 U, about 95 U, about 100 U, about 105 U, about 110 U, about 115 U, about 120 U, about 125 U, about 130 U, about 135 U, about 140 U, about 145 U, about 150 U, about 155 U, about 160 U, about 165 U, about 170 U, about 175 U, about 180 U, about 185 U, about 190 U, about 195 U, or about 200 U per treatment are administered to a patient with muscle spasticity. In an embodiment, the biceps brachii can be injected with between 100 U and 200 U divided into 4 injection sites. In an embodiment, the flexor carpi radialis can be injected with between 12.5 U and 50 U in 1 injection site. In an embodiment, the flexor carpi ulnaris can be injected with between 12.5 U and 50 U in 1 injection site. In an embodiment, the flexor digitorum *profundus* can be injected with between 30 U and 50 U in one injection site. In an embodiment, the flexor digitorum sublimis can be injected with between 30 U and 50 in a single injection site. Dosages greater than 200 U per treatment may also be administered to patients with muscle spasticity to achieve a therapeutic response. A treatment session can comprise multiple treatments.

Treatment of Pain

In another embodiment, methods for treating pain comprising the step of administering a pharmaceutical composition described herein to a subject in need thereof in an amount sufficient to reduce pain. In another embodiment, the patient suffers from myofascial pain, migraine headache pain, tension headache pain, neuropathic pain, facial pain, lower-back pain, sinus-headache pain, pain associated with temporomandibular joint disease, pain associated with spasticity or cervical dystonia, post-surgical wound pain, or neuralgia. A treatment session can comprise multiple treatments.

In an embodiment, the patient suffers from facial pain. A subject suffering from facial pain, for example, receives between about 4 to 40 U per treatment of a pharmaceutical composition described herein. In a further example, the subject receives between about 4 to 10 U, 4 to 15 U, 4 to 20 U, 4 to 25 U, 4 to 30 U, 4 to 35 U, 7 to 15 U, 7 to 20 U, 7 to 25 U, 7 to 30 U, 7 to 35 U, or 7 to 40 U per treatment are administered to a patient suffering from facial pain. In a still further example, the subject receives about 4 U, about 5 U, about 7.5 U, about 10 U, about 12.5 U, about 15 U, about 17.5 U, about 20.0 U, about 22.5 U, about 25.0 U, about 27.5 U, about 30.0 U, about 32.5 U, about 35 U, about 37.5 U, or about 40 U per treatment are administered to a patient with facial pain. Dosages greater than 40 U per treatment may also be administered to patients with facial pain to achieve a therapeutic response. A treatment session can comprise multiple treatments.

In an embodiment, the patient suffers from myofascial pain. A subject suffering from myofascial pain, for example, receives between about 5 to 100 U per treatment of a pharmaceutical composition described herein. In a further example, the subject receives between about 5 to 10 U, 5 to 20 U, 5 to 30 U, 5 to 40 Units, 5 to 50 Units, 5 to 60 Units, 5 to 70 Units, 5 to 80 Units, 5 to 90 U, 10 to 20 U, 10 to 30 U, 10 to 50 U, or 10 to 60 U, or 10 to 70 U, or 10 to 80 U, 10 to 90 U, or 10 to 100 U per treatment are administered to a patient suffering from myofascial pain. In a further example, the subject receives about 5 U, about 10 U, about 15 U, about 20 U, about 25 U, about 30 U, about 35 U, about 40 U, about 45 U, about 50 U, about 55 U, about 60 U, about 65 U, about 70 U, about 75 U, about 80 U, about 85 U, about 90 U, about 95 U, or about 100 U per treatment. Dosages greater than 100 U per treatment may also be administered to patients with myofascial pain to achieve a therapeutic response. A treatment session can comprise multiple treatments.

In an embodiment, the subject suffers from lower-back pain. A subject suffering from lower-back pain, for example, receives between about 15 to 150 U per treatment of a pharmaceutical composition described herein. In a further example, the subject receives between about 15 to 30 U, 15 to 50 U, 15 to 75 U, 15 to 100 U, 15 to 125 U, 15 to 150 U, 20 to 100 U, 20 to 150 U, or 100 to 150 U per treatment. In a still further example, the subject receives about 15 U, about 20 U, about 25 U, about 30 U, about 35 U, about 40 U, about 45 U, about 50 U, about 55 U, about 60 U, about 65 U, about 70 U, about 75 U, about 80 U, about 85 U, about 90 U, about 95 U, about 100 U, about 105 U, about 110 U, about 115 U, about 120 U, about 125 U, about 130 U, about 135 U, about 140 U, about 145 U, or about 150 U per treatment to alleviate lower-back pain. Dosages greater than 150 U per treatment may also be administered to patients with lower-back pain to achieve a therapeutic response. A treatment session can comprise multiple treatments.

In an embodiment, the patient suffers from migraine headache pain, including wherein the patient suffers from migraine headaches of 4 hours or more 15 or more days per month. A subject suffering from migraine-headache pain, for example, receives between about 0.5 to 200 U per treatment of a pharmaceutical composition described herein. In a further example, the subject receives between about 5 to 190 U, 15 to 180 U, 25 to 170 U, 35 to 160 U, 45 to 150 U, 55 to 140 U, 65 to 130 U, 75 to 120 U, 85 to 110 U, or 95 to 105 U per treatment to alleviate migraine headache pain. A treatment session can comprise multiple treatments.

For example, about 0.5 U, about 1.0 U, about 1.5 U, about 2.0 U, about 2.5 U, about 3.0 U, about 3.5 U, about 4.0 U, about 4.5 U, about 5.0 U, about 5.5 U, about 6.0 U, about 6.5 U, about 7.0 U, about 7.5 U, about 8.0 U, about 8.5 U, about 9.0 U, about 9.5 U, about 10.0 U, about 12 U, about 15 U, about 17 U, about 20 U, about 22 U, about 25 U, about 27 U, about 30 U, about 32 U, about 35 U, about 37 U, about 40 U, about 42 U, about 45 U, about 47 U, or about 50 U per treatment site are administered to a patient with migraine-headache pain. A patient can be treated at multiple sites, such as, for example, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites, 18 sites, 19 sites, 20 sites, 21 sites, 22 sites, 23 sites, 24 sites, 25 sites, 26 sites, 27 sites, 28 sites, 29 sites, 30 sites, 31 sites, 32 sites, or more, or the like. In an embodiment, a patient suffering from migraine is injected 31 times with 5 U per 0.1 mL injection, across the corrugator (2 injections of 5 U each), procerus (1 injection of 5 U), frontalis (4 injections of 5 U each), temporalis (8 injections of 5 U each), occipitalis (6 injections of 5 U each), cervical paraspinal (4 injections of 5 U each), and trapezius (6 injections of 5 U each) muscles. With the exception of the procerus muscle which can be injected at the midline, all muscles can, in certain embodiments, be injected bilaterally with half of the injection sites to the left and half to the right side of the head and neck. Dosages greater than 200 U per treatment may also be administered to patients with migraine-headache pain to achieve a therapeutic response. A treatment session can comprise multiple treatments.

In an embodiment, the patient suffers from sinus-headache pain. A subject suffering from sinus-headache pain, for example, receives between about 4 to 40 U per treatment of a pharmaceutical composition described herein. In a further example, the subject receives between about 4 to 10 U, 4 to 15 U, 4 to 20 U, 4 to 25 U, 4 to 30 U, 4 to 35 U, 7 to 15 U, 7 to 20 U, 7 to 25 U, 7 to 30 U, 7 to 35 U, or 7 to 40 U per treatment to alleviate sinus-headache pain. In a still further example, the subject receives about 4 U, about 5 U, about 7.5 U, about 10 U, about 12.5 U, about 15 U, about 17.5 U, about 20.0 U, about 22.5 U, about 25.0 U, about 27.5 U, about 30.0 U, about 32.5 U, about 35 U, about 37.5 U, or about 40 U per treatment. Dosages greater than 40 U per treatment may also be administered to patients with sinus headache-pain to achieve a therapeutic response. A treatment session can comprise multiple treatments.

In an embodiment, the patient suffers from tension-headache pain. A subject suffering from tension-headache pain, for example, receives between about 5 to 50 U per treatment of a pharmaceutical composition described herein. In a further example, between about 5 to 10 U, 5 to 15 U, 5 to 20 U, 5 to 25 U, 5 to 30 U, 5 to 35 U, 5 to 40 U, 5 to 45 U, 10 to 20 U, 10 to 25 U, 10 to 30 U, 10 to 35 U, 10 to 40 U, or 10 to 45 U per treatment are administered to a patient with tension-headache pain. In a still further example, the subject receives about 5 U, about 10 U, about 20 U, about 25 U, about 30 U, about 35 U, about 40 U, about 45 U, or about 50 U per treatment administered to alleviate tension-headache pain. In an embodiment, a patient suffering from tension headache is injected 31 times with 5 U per 0.1 mL injection, across the corrugator (2 injections of 5 U each), procerus (1 injection of 5 U), *frontalis* (4 injections of 5 U each), temporalis (8 injections of 5 U each), occipitalis (6 injections of 5 U each), cervical paraspinal (4 injections of 5 U each), and trapezius (6 injections of 5 U each) muscles. With the exception of the procerus muscle which can be injected at the midline, all muscles can, in certain embodiments, be injected bilaterally with half of the injection sites to the left and half to the right side of the head and neck. Dosages greater than 200 U per treatment may also be administered to patients with tension headache pain to achieve a therapeutic response. A treatment session can comprise multiple treatments.

In an embodiment, the patient suffers from sinus headache pain or facial pain associated with acute or recurrent chronic sinusitis. For example, a pharmaceutical composition as described herein can be administered to the nasal mucosa or to the subcutaneous structures overlying the sinuses, wherein the administration of the formulation reduces the headache and/or facial pain associated with acute recurrent or chronic sinusitis. In further embodiments, any of the pharmaceutical formulations described herein can be administered to the nasal mucosa or to the subcutaneous structures overlying the sinuses, such as over one or more of the sinuses selected from the group consisting of: ethmoid; maxillary; mastoid; frontal; and sphenoid. In another embodiment, subcutaneous structures overlying the sinuses lie within one or more of the areas selected from the group consisting of: forehead; malar; temporal; post auricular; and lip. In embodiments, multiple injections of 5 U each are administered to treat the sinus headache pain or facial pain associated with acute or recurrent chronic sinusitis.

In another embodiment, a patient suffering from sinus headache pain or facial pain associated with acute or recurrent chronic sinusitis is treated by administering any of the pharmaceutical formulations described herein to an afflicted area of the patient. In a further embodiment, the pharmaceutical formulations disclosed herein are administered to the projections of a trigeminal nerve innervating a sinus.

Patients suffering from sinus headache pain or facial pain associated with acute or recurrent chronic sinusitis often exhibit symptoms including rhinitis, sinus hypersecretion and/or purulent nasal discharge. In one embodiment, patients treated with the pharmaceutical compositions described herein exhibit, prior to treatment, symptoms of sinus hypersecretion and purulent nasal discharge.

Embodiments contemplated herein provide methods for treating a patient suffering from sinus headache pain or facial pain associated with acute or recurrent chronic sinusitis, wherein the subject suffers from neuralgia. In certain embodiments, the neuralgia is trigeminal neuralgia. In another embodiment, the neuralgia is: associated with compressive forces on a sensory nerve; associated with intrinsic nerve damage, demyelinating disease, or a genetic disorder; associated with a metabolic disorder; associated with central neurologic vascular disease; or associated with trauma. In another embodiment, the pain is associated with dental extraction or reconstruction.

Treatment of Urological Disorders

In an embodiment, methods for treating a patient suffering from overactive bladder (OAB), such as, for example, that due to a neurologic condition (NOAB), or idiopathic OAB (IOAB) are provided. For example, pharmaceutical formulations described herein can be administered to the bladder or its vicinity, e.g. the detrusor, wherein the administration of the formulation reduces the urge incontinence associated with overactive bladder. In certain embodiments, the dosage can be, for example, 200 U, or more, or less, or the like. For example, the dosage can be about 15 U, about 20 U, about 25 U, about 30 U, about 35 U, about 40 U, about 45 U, about 50 U, about 55 U, about 60 U, about 65 U, about 70 U, about 75 U, about 80 U, about 85 U, about 90 U, about 95 U, about 100 U, about 105 U, about 110 U, about 115 U, about 120 U, about 125 U, about 130 U, about 135 U, about 140 U, about 145 U, about 150 U, about 160 U, about 170 U, about 180 U, about 190 U, about 200 U, about 210 U, about 220, about 230 U, about 240 U, or more, or the like, per treatment. A patient can be injected at multiple sites, such as, for example, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites, 18 sites, 19 sites, 20 sites, 21 sites, 22 sites, 23 sites, 24 sites, 25 sites, 26 sites, 27 sites, 28 sites, 29 sites, 30 sites, 31 sites, 32 sites, 33 sites, 34 sites, 35 sites, 36 sites, 37 sites, 38 sites, or more, or the like. In an embodiment, patients suffering from OAB are treated with 30 1 mL injections of approximately 6.7 U per injection into the detrusor muscle.

In an embodiment, methods for treating a patient suffering from neurogenic detrusor overactivity (NDO), such as that due to a neurologic condition, are provided. For example, pharmaceutical formulations can be administered to the bladder or its vicinity, e.g. the detrusor, wherein the administration of the formulation reduces the urge incontinence associated with overactive bladder. In certain embodiments, the dosage can be, for example, 200 U, or more, or less, or the like. For example, the dosage can be about 15 U, about 20 U, about 25 U, about 30 U, about 35 U, about 40 U, about 45 U, about 50 U, about 55 U, about 60 U, about 65 U, about 70 U, about 75 U, about 80 U, about 85 U, about 90 U, about 95 U, about 100 U, about 105 U, about 110 U, about 115 U, about 120 U, about 125 U, about 130 U, about 135 U, about 140 U, about 145 U, about 150 U, about 160 U, about 170 U, about 180 U, about 190 U, about 200 U, about 210 U, about 220, about 230 U, about 240 U, or more, or the like, per treatment. A patient can be injected at multiple sites, such as, for example, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites, 18 sites, 19 sites, 20 sites, 21 sites, 22 sites, 23 sites, 24 sites, 25 sites, 26 sites, 27 sites, 28 sites, 29 sites, 30 sites, 31 sites, 32 sites, or more, or the like. In an embodiment, patients suffering from NDO are treated with 30 1 mL injections of approximately 6.7 U per injection into the detrusor muscle.

Treatment of Cosmetic Features

In another embodiment, methods for cosmetically modifying soft-tissue features comprising the step of administering at least one pharmaceutical composition as described herein to a subject in need thereof in an amount sufficient to modify said features are provided. In a further embodiment, the pharmaceutical composition is administered via transcutaneous or transmucosal injection either at a single focus or multiple foci.

In embodiments, pharmaceutical formulations are administered to the face or neck of the subject. In a further embodiment, the pharmaceutical formulations are administered to the subject in an amount sufficient to reduce rhytides. For example, the formulation can be administered between eyebrows of the subject in an amount sufficient to reduce vertical lines between the eyebrows and on a bridge of a nose. The pharmaceutical formulations can also be administered near either one or both eyes of the subject in an amount sufficient to reduce lines at corners of the eyes. In an embodiment, compositions can be injected locally to smooth skin. In another embodiment, the pharmaceutical formulations can also be administered to a forehead of the subject in an amount sufficient to reduce horizontal lines on said forehead. In yet another embodiment, the pharmaceutical formulation is administered to the neck of the subject in an amount sufficient to reduce muscle bands in the neck. In an embodiment, a pharmaceutical composition is applied to the masseter muscle to relax the muscle and/or decrease masseter mass.

In a further embodiment, the patient suffers from facial wrinkles. A subject suffering from facial wrinkles, for example, can receive between about 1 to 100 U per treatment of a pharmaceutical formulation. In a further example, the subject receives between about 1 to 10 U, 1 to 20 U, 1 to 30 U, 1 to 40 U, 1 to 50 U, 1 to 60 U, 1 to 70 U, 1 to 80 U, 1 to 90 U, 5 to 20 U, 5 to 30 U, 5 to 40 U, 5 to 50 U, 5 to 60 U, 5 to 70 U, 5 to 80 U, 5 to 90 U, or 5 to 100 U per treatment. In a still further example, the subject receives about 1 U, about 10 U, about 20 U, about 30 U, about 40 U, about 50 U, about 60 U, about 70 U, about 80 U, about 90 U, or about 100 U per treatment. Dosages greater than 100 U per treatment may also be administered to patients suffering from inflammation or an inflammatory disorder to achieve a therapeutic response.

Treatment of Inflammation

In another embodiment, methods for treating inflammation comprising the step of administering a pharmaceutical composition as described herein to a subject in need thereof in an amount sufficient to reduce inflammation. In certain embodiments, pharmaceutical formulations are administered to a patient without producing muscle weakness. In an embodiment, the pharmaceutical formulations are administered to patients with an inflammatory condition. In certain embodiments, the inflammatory condition is neurogenic inflammation. In another embodiment, the subject suffers from rheumatoid arthritis or a gastro-intestinal inflammatory disease.

In a further embodiment, the patient suffers from an inflammatory disorder. A subject suffering from an inflammatory disorder, for example, receives between about 1 to 100 U per treatment of a pharmaceutical composition as described herein. In a further example, the subject receives between about 1 to 10 U, 1 to 20 U, 1 to 30 U, 1 to 40 U, 1 to 50 U, 1 to 60 U, 1 to 70 U, 1 to 80 U, 1 to 90 U, 5 to 20 U, 5 to 30 U, 5 to 40 U, 5 to 50 U, 5 to 60 U, 5 to 70 U, 5 to 80 U, 5 to 90 U, or 5 to 100 U per treatment. In a still further example, the subject receives about 1 U, about 10 U, about 20 U, about 30 U, about 40 U, about 50 U, about 60 U, about 70 U, about 80 U, about 90 U, or about 100 U per treatment. Dosages greater than 100 U per treatment may also be administered to patients suffering from inflammation or an inflammatory disorder to achieve a therapeutic response.

Treatment of Skin Conditions

A method for treating a skin disorder can have the step of local administration of a botulinum neurotoxin to a location of a skin disorder of a patient, such as to a face, hand or foot of a patient. The neurotoxin can be locally administered in an amount of between about 10-3 units/kg of patient weight and about 35 units/kg of patient weight. For example, the neurotoxin is locally administered in an amount of between about $10^2$ U/kg and about 25 U/kg of patient weight. In a further example, the neurotoxin is administered in an amount of between about $10^4$ U/kg and about 15 U/kg. In one method, the neurotoxin is locally administered in an amount of between about 1 U/kg and about 10 U/kg in a composition as described herein. In a clinical setting, it can be advantageous to administer from 1 U to 3000 U of a neurotoxin, such as botulinum toxin type A or B, to a skin disorder location by topical application or by subdermal administration, to effectively treat the skin disorder.

Administration of botulinum toxin can be carried out at multiple sites in the skin, wherein the sites of adjacent injections are separated by about 0.1 to 10 cm, or about 0.5 to about 5 cm, for example, by about 1.5 to about 3 cm. The toxins may be any of the botulinum toxins A, B, C, D, E, F, G or a mosaic toxin. The amounts administered may vary between 0.1 and 1000 U, or about 1 to about 40, or from about 5 to about 10 U, depending on the manufactures specifications, the class of the toxin and the mode of administration. The repeat time range for these administrations for maintenance of the desired change varies substantially according to the location of the injection, the condition to be adjusted and the condition of the patient. Thus, the repeat time may vary from about 1 week to about 50 weeks, however, a common range is about 4 to about 25 weeks, or even about 12 weeks to about 16 weeks.

The distances between administration sites, such as, for example, injection sites, can vary from about 1 mm to about 10 cm, suitably from about 5 mm to about 5 cm, and more usually from about 1 cm to about 3 cm. Thus, for example botulinum A may be suitably administered by intradermal injection between about 0.1 to about 10 U at a separation of from about 0.5 to about 10 cm.

In another embodiment, methods for treating cutaneous disorders comprising the step of administering a pharmaceutical composition as described herein to a subject in need thereof in an amount sufficient to reduce a sebaceous or mucous secretion is provided. In further embodiments, the pharmaceutical compositions as described herein are administered to a patient without producing muscle weakness. In certain embodiments, the pharmaceutical composition as described herein are injected into one or more sites of an eyelid or conjunctiva. In another embodiment, the formulations are administered to a body surface.

In another embodiment, the pharmaceutical formulations are administered in an amount sufficient to reduce cutaneous bacterial or fungal growth, including but not limited to *Staphylococcus;* *Streptococcus* and *Moraxella.* For example, the pharmaceutical compositions as described herein are administered to an area selected from the group consisting of: eyelid; scalp; feet; groin; and armpit to reduce cutaneous infection.

Treatment of Depression

In another embodiment, a method for treating depression is provided. Depression is a general term for recognized forms of depression that are defined and are separately diagnosed according to criteria given in handbooks for psychiatry, for example in the *Diagnostic and Statistical Manual of Mental Disorders* 4th edition (DSM-IV) published by the American Psychiatric Association, Washington, D.C. (1994). In the DSM-IV, depressive disorders are classified under mood disorders and are divided into three types: major depressive disorder, dysthymic disorder and depressive disorder not otherwise specified (or "atypical"). In general, regardless of whether or not the depressive syndrome is melancholic, atypical, or some admixture of the two, a diagnosis of major depression is given when depressed mood is present, or loss of interest or pleasure in all activities is present, for at least two weeks.

Depression is often associated with psychomotor abnormalities, such as increased or retarded motor activity. Many depressed persons can also be recognized by their "depressed facies" in which the muscles of facial expression assume a distressed or sad appearance. For example, the brow may be furrowed, the inner ends of the eyebrows raised, and the angles of the mouth lowered such that the facial appearance is recognizably sad and/or anxious. Four major muscle groups are involved in frowning: the frontal, procerus, corrugator supercilii and orbicularis oculi (Weider et al. *Derm Surg.* 24:1172-1174, 1998. The corrugator supercilii is also known as the "scowl" muscle.

A subject diagnosed with depression or experiencing a depressive episode is treated by administering any of the pharmaceutical compositions described herein. In a further embodiment, the pharmaceutical formulations disclosed herein are administered to the patient via injection subcutaneously. Example 10 describes treatment of a person with a form of depression by administering a therapeutically effective amount of botulinum toxin in a composition comprising botulinum toxin, trehalose, a poloxamer surfactant, and methionine. The composition is administered to a facial muscle involved in frowning or scowling. The neurotoxin affects the ability of the subject to frown and/or scowl, thereby treating depression. More generally, a therapeutically effective amount of Botulinum toxin A can be injected into one or more of the frontalis, procerus, the corrugator supercilii, orbicularis oculi, or the depressor anguli oris (triangularis muscle).

In another embodiment, the method comprises administering a therapeutically effective amount of a Clostridial toxin active ingredient in a composition as described herein to a facial muscle involved in frowning, scowling, or a sad appearance. The Clostridial toxin active ingredient causes partial or complete paralysis of the facial muscle, thereby affecting the ability of the subject to frown and/or scowl, or appear sad, and thereby treat depression. For example, a therapeutically effective amount of a composition comprising the Clostridial toxin active ingredient botulinum toxin, along with a surfactant, an antioxidant, and optionally a tonicity modifier, can be injected into one or more of the orbicularis oculi, frontalis, procerus, the corrugator supercilii, or the depressor anguli oris (triangularis muscle). In a specific example, the composition comprising Botulinum toxin A is injected into the procerus muscle over the glabella. Other administration points and paradigms are disclosed, for example, in U.S. Pat. No. 7,758,872, which is incorporated by reference herein.

In other embodiments of the method, adult subjects with moderate to severe major depressive disorder (MDD), either single episode or recurrent are contemplated for treatment, where the MDD diagnosis is based upon the DSM-IV-TR criteria. In one embodiment, a single treatment is contemplated, and in other embodiments, a single, repeated treatment is contemplated, with the treatment is repeated at intervals of 2-6, 2-4, or 3-6 months. The amount of Clostridial toxin active ingredient dosed is, for example, 30 U or 50 U, where, in some embodiments, the dose is divided into a plurality of injections. In one embodiment, the plurality of injections is 6 and in another embodiment, is 8. In one embodiment, 30 U is divided into 6 injections to the glabellar region of the forehead (procerus and corrugator muscles). In one embodiment, 50 U is divided into 8 injections to the glabellar region of the forehead (procerus and corrugator muscles).

Effective treatment is indicated by, for example, a primary efficacy measure known in the art, such as the clinical assessment known as Montgomery-Asberg Depression Rating scale. Additional efficacy measures: clinic CGI-S score (Clinical Global Impression of Change scores), clinic HAM-D17 total score (Hamilton Rating Scale for Depression).

Treatment of Cardiac Arrhythmia

In another embodiment, a method for treating cardiac arrhythmia is provided. Arrhythmias are caused by a disruption of the normal functioning of the electrical conduction system of the heart. Normally, the chambers of the heart (atria and ventricles) contract in a coordinated manner. The signal to contract is an electrical impulse that begins in the sinoatrial nod, and the impulse is conducted through the atria and stimulates them to contract. The impulse passes through the atrioventricular node, then travels through the ventricles and stimulates them to contract. Problems can occur anywhere along the conduction system, causing various arrhythmias. Problems can also occur in the heart muscle itself, causing it to respond differently to the signal to contract, also causing arrhythmias, or causing the ventricles to contract independently of the normal conduction system.

Arrhythmias include tachycardias, bradycardias and true arrhythmias of disturbed rhythm. Arrhythmias are classified as lethal if they cause a severe decrease in the pumping function of the heart. When the pumping function is severely decreased for more than a few seconds, blood circulation is essentially stopped, and organ damage (such as brain damage) can occur within a few minutes. Lethal arrhythmias include ventricular fibrillation, also ventricular tachycardia that is rapid and sustained, or pulseless, and may include sustained episodes of other arrhythmias. Additional types of arrhythmias include atrial fibrillation or flutter, multifocal atrial tachycardia, paroxysmal supraventricular tachycardia, Wolff-Parkinson-White syndrome, sinus tachycardia, sinus bradycardia, bradycardia associated with heart block, sick sinus syndrome, and ectopic heartbeat.

Accordingly, a method for treating cardiac arrhythmia is provided, the method comprising the step of administering a composition as described herein that comprises a therapeutically effective amount of Clostridial toxin active ingredient, the composition administered locally to the heart of a patient with a cardiac arrhythmia or at risk of a cardiac arrhythmia. Particular arrhythmias treatable include bradycardia and tachycardia. In one embodiment, the composition is locally administered, by which is meant administration directly to, in, or to the vicinity of, the cardiac muscle to be treated. Local administration includes intrapericardial, intracardiac cardiac catheterization and direct cardiac muscle injection routes of administration for the composition.

Example 11 describes treatment of a person undergoing cardiac surgery by administering a therapeutically effective amount of botulinum toxin in a composition comprising botulinum toxin, trehalose, a poloxamer surfactant, and NAC. In one embodiment, the composition is administered via injection into one or more epicardial fat pads of the heart. The dose administered, in one exemplary embodiment, 25 U per epicardial fat pad, to a total dose of 125 U. In another exemplary embodiment, 50 U per epicardial fat pad, to a total dose of 250 U, is administered.

Effective treatment is indicated by, for example, a primary efficacy endpoint of, for example, incidence of atrial fibrillation (AF) as measured by ECG for 4 weeks or at 4 weeks post treatment. Additional efficacy endpoints include length of hospital stay, length of stay in ICU, rehospitalization rate, anticoagulant medication use, need for interventional procedures for post operative atrial fibrillation, such as ablation, pacemaker implantation, electrical or pharmacologic cardioversion.

EXAMPLES

The following examples illustrate embodiments and aspects of the present compositions and methods and are not intended to limit the scope thereof.

Example 1

Activities and Stabilities of Exemplary Solid Clostridial Pharmaceutical Compositions Bulk solutions of botulinum toxin were prepared by mixing an appropriate aliquot of a botulinum toxin type A with a solution having the ingredients set forth in Tables 1-3. Four formulations were prepared for testing, referred to as Formulation 1, Formulation 2, Formulation 3 and Formulation 4, and three comparative formulations were prepared, referred to as Comparator 1, Comparator 2, and Comparator 3. Formulations 1, 2, 3 and 4 were composed of a disaccharide, a surfactant, an antioxidant and a histidine buffer. Each formulation was filled into a glass vial and lyophilized using conventional freeze-drying conditions. Portions of the lyophilized formulations were stored under several conditions; for example, at 25° C. and at 40° C. for six months (Tables 1.1 and 1.2), or at −20° C. and 40° C. for 1 month (Table 2), or at 25° C. for 7.5 months (Table 3). Potency of the lyophilized formulations after storage and reconstitution with saline was tested by a cell based potency assay, as described in U.S. Pat. No. 8,618,261, the assay details of which are incorporated by reference herein. The results were normalized to target. The potencies of the solid compositions are shown in Tables 1-3.

Example 2

Activities of Liquid Clostridial Pharmaceutical Compositions in the Presence or Absence of Antioxidants Bulk drug product solutions were prepared by mixing an appropriate aliquot of a botulinum toxin type A with three different vehicle solutions as shown in Table 4. All three formulations contained 8% w/w trehalose, 4% w/w poloxamer P188 and 20 mM histidine buffer at pH 6.0. Formulation 10 contained no antioxidant. Formulations 11 and 12 contained NAC and methionine, respectively. The bulk solutions were filled into 2 mL glass vials (1.25 mL fill), and sealed with rubber stopper and aluminum shell. Potency of the formulations was tested by a cell based potency assay after filling (time zero, t0) and after storage for one month at four temperatures (−70° C., 5° C., 25° C. and 40° C.). The target potency was 100 Units/mL. Potency test results are given in Table 4.

Example 3

Impact of Exemplary Antioxidants on the Stability of Exemplary Liquid Formulations Bulk drug product solutions were prepared by mixing an appropriate aliquot of the BoNT/A drug substance with different antioxidants as shown in Table 3.1. All compositions contained 8% w/w trehalose, 4% w/w poloxamer P188, 20 mM histidine buffer at pH 6.0 and 0.2 wt % of one or more of the following antioxidants: NAC, L-methionine, L-tryptophan, L-glutathione, sodium sulfite, and/or propyl gallate, and/or EDTA. The formulations are specified in Table 3.1. Target potency was 100 U/mL. The bulk solutions were filled into 2 mL glass vials (1.25 mL fill), and sealed with rubber stopper and aluminum shell. Potency of the formulations was tested by a cell based potency assay after filling (time zero, t0) and after storage at 40° C. for 2 weeks and 1 month. Potency test results are given in Table 5, above.

TABLE 3.1

| Formulation No. | Toxin U/mL | Tre % | P188 % | Buffer | NAC % | Met % | TRP % | GSH % | NaSul % | PrpGal % | EDTA % |
|---|---|---|---|---|---|---|---|---|---|---|---|
| Formulation 20 | 100 | 8 | 4 | 20 mM His, pH 6.0 | | 0.2 | | | | | |

TABLE 3.1-continued

| Formulation No. | Toxin U/mL | Tre % | P188 % | Buffer | NAC % | Met % | TRP % | GSH % | NaSul % | PrpGal % | EDTA % |
|---|---|---|---|---|---|---|---|---|---|---|---|
| Formulation 21 | 100 | 8 | 4 | 20 mM His, pH 6.0 | | | 0.2 | | | | |
| Formulation 22 | 100 | 8 | 4 | 20 mM His, pH 6.0 | | | | 0.2 | | | |
| Formulation 23 | 100 | 8 | 4 | 20 mM His, pH 6.0 | | | | | 0.2 | | |
| Formulation 24 | 100 | 8 | 4 | 20 mM His, pH 6.0 | | | | | | 0.2 | |
| Formulation 25 | 100 | 8 | 4 | 20 mM His, pH 6.0 | 0.2 | 0.2 | | | | | |
| Formulation 26 | 100 | 8 | 4 | 20 mM His, pH 6.0 | 0.2 | | | | | | 0.03 |
| Formulation 27 | 100 | 8 | 4 | 20 mM His, pH 6.0 | 0.2 | 0.2 | | | | | 0.03 |
| Formulation 28 | 100 | 8 | 4 | 20 mM His, pH 6.0 | | 0.2 | 0.2 | | | | |

Tre = trehalose;
P-188 = poloxamer P188;
His = L-histidine;
NAC = N-acetyl-L-cysteine;
Met = L-methionine;
TRP = L-tryptophan;
GSH = L-glutathione;
NaSul = sodium sulfite;
PrpGal = propyl gallate;
EDTA = ethylene diamine tetraacetic acid, sodium salt.

Example 4

Impact of Exemplary Disaccharides on the Stability of Exemplary Liquid Compositions Liquid compositions were prepared by mixing an appropriate aliquot of BoNT/A (100 U/mL) with solutions of one of 800 w/w trehalose or 80% w/w sucrose, and of 400 w/w poloxamer P188 and 0.2 w/w % L-methionine, in 20 mM histidine buffer at pH 6.0. The composition with trehalose was assigned Formulation No. 30 and the composition with sucrose was assigned Formulation No. 31. The compositions were stored at 25° C. and potency was tested by cell based potency assay prior to storage (time zero, t0) and at selected time points after storage. Potency test results are shown in Table 6.

Example 5

Impact of Exemplary Surfactants on the Stability of Exemplary Liquid Compositions Liquid compositions were prepared by mixing an appropriate aliquot of BoNT/A (100 U/mL) with solutions comprising poloxamer P188 (4 w/w %) or polysorbate (TWEEN® 20, 0.04 w/w %) and 8% w/w trehalose, 0.2 w/w % L-methionine, in 20 mM histidine buffer at pH 6.0. The composition with poloxamer P188 was identified as Formulation No. 30 and the composition with polysorbate was identified as Formulation No. 32. Potency was tested by cell based potency assay prior to storage (time zero, t0) and after 1 month of storage at 40° C. Potency test results are shown in Table 7.

Example 6

Stability of Toxin in Compositions with No Tonicity Agent

Five liquid compositions were prepared by mixing an appropriate aliquot of BoNT/A (100 U/mL or 150 U/mL) with solutions comprising or lacking poloxamer P188 (4 w/w %), 8% w/w trehalose, and 0.2 w/w % L-methionine, in 20 mM histidine buffer at pH 6.0. Details of the compositions are given in Table 6.1:

TABLE 6.1

| Formulation No. | Toxin U/mL | Trehalose % | Poloxamer P188 % | Methionine % | Buffer |
|---|---|---|---|---|---|
| Formulation 33 | 100 | 8 | 4 | 0 | 20 mM His, pH 6.0 |
| Formulation 34 | 150 | 0 | 0 | 0.2 | 20 mM His, pH 6.0 |
| Formulation 35 | 150 | 8 | 0 | 0.2 | 20 mM His, pH 6.0 |
| Formulation 36 | 100 | 0 | 4 | 0.2 | 20 mM His, pH 6.0 |
| Formulation 37 | 100 | 8 | 4 | 0.2 | 20 mM His, pH 6.0 |

Potency of Formulations 33-37 was tested by cell based potency assay prior to storage (time zero, t0) and after 1 month of storage at −70° C. and 40° C. for 1 month. Potency test results are shown in Table 8.

Example 7

Stability of Toxin in Liquid Compositions

Liquid compositions were prepared by mixing an appropriate aliquot of BoNT/A (100 U/mL) with solutions comprising poloxamer P188 (4 w/w %) or polysorbate (TWEEN®-20, 0.04 w/w %), sucrose or trehalose (8% w/w) or NaCl (0.9 w/w %), and 0.2 w/w % L-methionine, in water or 20 mM histidine buffer at pH 6.0. Details of the compositions are given in Table 7.1:

TABLE 7.1

| Formulation No. | Toxin U/mL | Treh % | Suc % | NaCl % | P188 % | Polysorbate (TWEEN® 20) % | Met % | Buffer* or water |
|---|---|---|---|---|---|---|---|---|
| Formulation 31 | 100 | | 8 | | 4 | | 0.2 | buffer |
| Formulation 38 | 100 | | 8 | | 4 | | 0.2 | water |
| Formulation 39 | 100 | | | 0.9 | 4 | | 0.2 | buffer |
| Formulation 40 | 100 | 8 | | | | 0.04 | 0.2 | buffer |

Tre = trehalose;
Suc = sucrose;
P-188 = poloxamer P188;
Met = L-methionine
*Buffer = 20 mM His, pH 6.0

Potency of Formulations 31 and 38-40 was tested by a cell based potency assay prior to storage (time zero, t0) and after 5.5 months, 7.5 months and 12 months of storage at 5° C. Potency test results are shown in Table 9.

Example 8

Stability of Toxin in Liquid Compositions with No Tonicity Agent

Liquid compositions were prepared by mixing an appropriate aliquot of BoNT/A (200 U/mL) with solutions comprising poloxamer P188 (4 w/w %) or polysorbate (TWEEN®-20, 0.04 w/w %) and 0.2 w/w % L-methionine, in 20 mM histidine buffer at pH 6.0. Details of the compositions are given in Table 8.1.

TABLE 8.1

| Formulation No. | Toxin U/mL | P188 % | Polysorbate (TWEEN ®20) % | methionine % | Buffer |
|---|---|---|---|---|---|
| Formulation 41 | 200 | 0 | 0.04 | 0.2 | 20 mM His, pH 6.0 |

TABLE 8.1-continued

| Formulation No. | Toxin U/mL | P188 % | Polysorbate (TWEEN ®20) % | methionine % | Buffer |
|---|---|---|---|---|---|
| Formulation 42 | 200 | 4 | 0 | 0.2 | 20 mM His, pH 6.0 |

P-188 = poloxamer P188;
Met = L-methionine

Potency of Formulations 41 and 42 was tested by a cell based potency assay prior to storage (time zero, t) and 2 weeks of storage at −70° C. and 40° C. Potency test results are shown in Table 10.

Example 9

Impact of Exemplary Lyoprotectors and Surfactants on the Stability of Exemplary Lyophilized Formulations Lyophilized compositions were prepared as follows. Bulk solutions of botulinum toxin were prepared by mixing an appropriate aliquot of a botulinum toxin type A (BoNT/A, 200 U/mL) with solutions comprising poloxamer P188 (4 w/w %) or polysorbate (TWEEN®20, 0.04 w/w %), with trehalose or sucrose (8 w/w %), and 0.2 w/w % L-methionine, in 20 mM histidine buffer at pH 6.0. Details of the compositions are given in Table 9.1. The solutions were filled into glass vials and lyophilized using conventional freeze-drying conditions.

TABLE 9.1

| Formulation No. | Toxin Target Potency U/vial | Trehalose % | Sucrose % | TWEEN® 20% | Poloxamer P188 % | Methionine % | Buffer |
|---|---|---|---|---|---|---|---|
| Formulation 43 | 200 | 8 | | 0 | 4 | 0.2 | 20 mM His, pH 6.0 |
| Formulation 44 | 200 | 8 | | 0.04 | 0 | 0.2 | 20 mM His, pH 6.0 |
| Formulation 45 | 200 | 0 | 8 | 0 | 4 | 0.2 | 20 mM His, pH 6.0 |
| Formulation 46 | 200 | 0 | 8 | 0.04 | 0 | 0.2 | 20 mM His, pH 6.0 |

Potency of the lyophilized compositions, designated as Formulations 43-46, was tested by a cell based potency assay after reconstitution of the lyophiles subsequent to storage for 2 weeks at −20° C. and 40° C. Potency test results are shown in Table 12.

Example 10

Method for Treating Depression

A lyophilized composition comprised of botulinum toxin type A (BoNT/A, 200 U), 8 wt % trehalose, 4 wt % poloxamer P188, 0.2 wt % methionine, in 20 mM histidine buffer, pH 6.0, is prepared as set forth in Example 9. The lyophilized composition is reconstituted in saline prior to administration.

A 50-year-old male reports a history of depression for two years. He is presently taking antidepressant medications (PAXIL® 20 mg orally per day and WELLBUTRIN 225 mg orally per day). The male subject reports continued depression. He is treated by injecting into the frown/glabellar lines 30 Unit equivalents of the reconstituted composition. Four months later he reports a much-improved mood with no feelings of depression. His frown/glabellar lines are re-treated with 30 Unit equivalents of the reconstituted composition.

Example 11

Method for Treating Cardia Arrhythmia

A formulation similar to Formulation 1 as described in Example 1 is prepared. The lyophilized composition is comprised of botulinum toxin type A (BoNT/A, 50 U), 2 wt % trehalose, 4 wt % poloxamer P188, 0.3 wt % NAC, in 20 mM histidine buffer, pH 5.5. The lyophilized composition is reconstituted in saline prior to administration.

A Caucasian male is undergoing cardiac surgery. As part of the surgical procedure, an amount of the reconstituted composition to provide a total dose of 75 U botulinum toxin is evenly divided for administration via injection into three epicardial fat pads of his heart. The medical staff reports no arrhythmia during or post-surgery.

Many alterations and modifications may be made by those having ordinary skill in the art, without departing from the spirit and scope of the disclosure. Therefore, it must be understood that the described embodiments have been set forth only for the purposes of examples, and that the embodiments should not be taken as limiting the scope of the following claims. The following claims are, therefore, to be read to include not only the combination of elements which are literally set forth, but all equivalent elements for performing substantially the same function in substantially the same way to obtain substantially the same result. The claims are thus to be understood to include those that have been described above, those that are conceptually equivalent, and those that incorporate the ideas of the disclosure.

What is claimed is:

1. A stable solid pharmaceutical composition which is free of animal protein excipients, the composition comprising:
   (i) a Clostridial botulinum toxin active ingredient;
   (ii) a poloxamer surfactant; and
   (iii) about 0.01 to 5 wt % methionine;
   wherein the composition is suitable for subcutaneous or intramuscular injection after reconstitution with an aqueous carrier; and wherein the solid composition is stable for at least one month at 40° C.

2. The composition of claim 1, wherein the Clostridial botulinum toxin active ingredient is botulinum toxin serotype E (BoNT/E).

3. The composition of claim 1, wherein the Clostridial botulinum toxin active ingredient comprises the approximately 150 kDa neurotoxin unassociated with complex proteins.

4. The composition of claim 1, wherein the composition further comprises a salt.

5. The composition of claim 4, wherein the salt comprises NaCl.

6. The composition of claim 1, wherein the poloxamer surfactant comprises poloxamer 188.

7. The composition of claim 1, wherein the composition further comprises a disaccharide.

8. The composition of claim 7, wherein the disaccharide is selected from sucrose or trehalose.

9. The composition of claim 7, where the disaccharide comprises trehalose.

10. The composition of claim 1, wherein the aqueous carrier comprises a buffer.

11. The composition of claim 10, wherein the buffer comprises histidine buffer.

12. The composition of claim 1, wherein the composition comprises:
   (i) botulinum toxin serotype E (BoNT/E);
   (ii) about 0.5 to 8 wt % of a poloxamer surfactant; and
   (iii) about 0.01 to 5 wt % methionine.

13. The composition of claim 1, wherein the composition comprises:
   (i) botulinum toxin serotype E (BoNT/E);
   (ii) histidine buffer;
   (iii) about 0.5 to 8 wt % of a poloxamer surfactant; and
   (iv) about 0.01 to 5 wt % methionine.

14. The composition of claim 1, wherein the composition comprises:
   (i) botulinum toxin serotype E (BoNT/E);
   (ii) histidine buffer;
   (iii) about 0.5 to 8 wt % Poloxamer 188; and
   (iv) about 0.01 to 5 wt % methionine.

15. The composition of claim 4, wherein the composition comprises:
   (i) botulinum toxin serotype E (BoNT/E);
   (ii) histidine buffer;
   (iii) about 0.5 to 8 wt % Poloxamer 188;
   (iv) about 0.01 to 5 wt % methionine; and
   (v) NaCl.

16. The composition of claim 7, wherein the composition comprises:
   (i) botulinum toxin serotype E (BoNT/E);
   (ii) histidine buffer;
   (iii) about 0.5 to 8 wt % Poloxamer 188;
   (iv) about 0.01 to 5 wt % methionine; and
   (v) trehalose.

17. The composition of claim 1, wherein the composition comprises:
   (i) botulinum toxin serotype E (BoNT/E);
   (ii) 20 mM histidine buffer;
   (iii) about 4 wt % Poloxamer 188;
   (iv) about 0.2 wt % methionine;
   (v) about 8 wt % trehalose; and
   (vi) about 0.2 wt % NaCl.

18. The composition of claim 1, wherein the composition comprises:
   (i) botulinum toxin serotype E (BoNT/E);
   (ii) 20 mM histidine buffer;
   (iii) about 4 wt % Poloxamer 188;
   (iv) about 0.2 wt % methionine;
   (v) about 2 wt % trehalose; and
   (vi) about 0.2 wt % NaCl.

19. The composition of claim 1, wherein the composition comprises:
   (i) botulinum toxin serotype E (BoNT/E);
   (ii) 20 mM histidine buffer;
   (iii) about 4 wt % Poloxamer 188;
   (iv) about 0.2 wt % methionine;
   (v) about 8 wt % trehalose; and
   (vi) about 0.6 wt % NaCl.

20. The composition of claim 1, wherein the composition is lyophilized.

21. The composition of claim 1, wherein the composition is vacuum dried.

22. The composition of claim 17, wherein the composition is lyophilized.

23. The composition of claim 18, wherein the composition is lyophilized.

24. The composition of claim 19, wherein the composition is lyophilized.

* * * * *